(12) United States Patent
Yen et al.

(10) Patent No.: US 11,524,967 B2
(45) Date of Patent: Dec. 13, 2022

(54) HETEROACENE AND ORGANIC ELECTROLUMINESCENCE DEVICE USING THE SAME

(71) Applicants: Feng-Wen Yen, Taipei (TW); Tsun-Yuan Huang, Chiayi (TW)

(72) Inventors: Feng-Wen Yen, Taipei (TW); Tsun-Yuan Huang, Chiayi (TW)

(73) Assignee: LUMINESCENCE TECHNOLOGY CORP., Hsin-Chu (TW)

( * ) Notice: Subject to any disclaimer, the term of this patent is extended or adjusted under 35 U.S.C. 154(b) by 436 days.

(21) Appl. No.: 16/532,512

(22) Filed: Aug. 6, 2019

(65) Prior Publication Data
US 2021/0040112 A1    Feb. 11, 2021

(51) Int. Cl.
| | | |
|---|---|---|
| C07D 495/14 | (2006.01) | |
| C07D 519/00 | (2006.01) | |
| C07D 491/153 | (2006.01) | |
| C07D 517/14 | (2006.01) | |
| C07D 495/04 | (2006.01) | |
| H01L 51/00 | (2006.01) | |
| H01L 51/50 | (2006.01) | |

(52) U.S. Cl.
CPC ....... *C07D 495/14* (2013.01); *C07D 491/153* (2013.01); *C07D 495/04* (2013.01); *C07D 517/14* (2013.01); *C07D 519/00* (2013.01); *H01L 51/0052* (2013.01); *H01L 51/0069* (2013.01); *H01L 51/0071* (2013.01); *H01L 51/5016* (2013.01); *H01L 51/5072* (2013.01)

(58) Field of Classification Search
None
See application file for complete search history.

(56) References Cited

U.S. PATENT DOCUMENTS

2006/0263635 A1* 11/2006 Ise .................. H01L 51/0087
                                                  428/917
2016/0322577 A1* 11/2016 Han .................. H01L 27/3248

FOREIGN PATENT DOCUMENTS

CN    106831798 A * 6/2017
JP    2007088016 A * 4/2007

OTHER PUBLICATIONS

Machine English translation of Huang et al. (CN-106831798-A). Oct. 13, 2021.*
Machine English translation of Katakura et al. (JP-2007088016-A). Mar. 21, 2022.*

* cited by examiner

*Primary Examiner* — Jay Yang

(57) ABSTRACT

A heteroacene having the following formula (F) is described. An organic electroluminescence device comprises the heteroacene as a phosphorescent host, a fluorescent host, a hole blocking layer, or an electron transport layer. The heteroacene lowers a driving voltage, or increases a current efficiency or a half-life of the organic electroluminescence device.

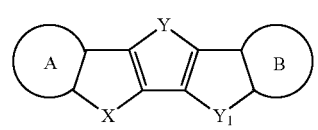

formula (F)

9 Claims, 4 Drawing Sheets

HETEROACENE AND ORGANIC ELECTROLUMINESCENCE DEVICE USING THE SAME

FIELD OF INVENTION

The present invention relates to a novel organic compound and, more particularly, to an organic electroluminescence device using the organic compound.

BACKGROUND OF THE INVENTION

Organic electroluminescence (organic EL) devices, i.e., organic light-emitting diodes (OLEDs) that make use of organic compounds, are becoming increasingly desirable than before. One of the organic compounds has the following formula:

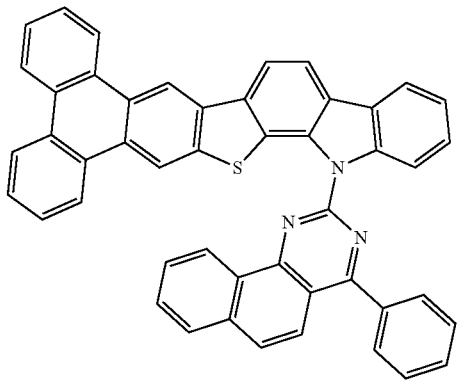

H11

For OLEDs, organic compounds may have performance advantages over conventional materials. For example, the wavelength at which an emissive layer emits light may generally be readily tuned with appropriate dopants. However, there is still a need for improvement of those organic compounds in an organic EL device, for example, in relation to the current efficiency, driving voltage or half-life of the organic EL device.

SUMMARY OF THE INVENTION

An object of the invention may be to provide an organic compound and an organic EL device using the same.

Another object of the present invention may be to improve an organic compound of an organic EL device, so that the organic EL device may have a higher current efficiency, a lower driving voltage, or a longer half-life.

According to the present invention, an organic compound which can be applied in an organic EL device is disclosed. The organic compound may have the following formula (F):

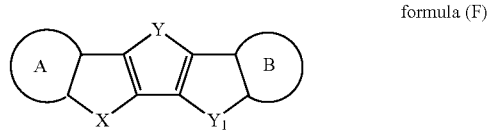

formula (F)

wherein X is a divalent bridge selected from the group consisting of O, S, Se and $CR_1R_2$. Y is a divalent bridge selected from the group consisting of O, S, Se and $CR_1R_2$ if $Y_1$ is N-L-Z. $Y_1$ is a divalent bridge selected from the group consisting of O, S, Se and $CR_1R_2$ if Y is N-L-Z. A and B independently represent a substituted or unsubstituted fused ring hydrocarbons unit having one or two rings. L represents a single bond or a substituted or unsubstituted divalent arylene group having 6 to 30 ring carbon atoms. Z represents a substituted or unsubstituted aryl group having 6 to 60 carbon atoms, and a substituted or unsubstituted hetroaryl group having 6 to 60 carbon atoms. $R_1$ and $R_2$ are independently selected from the group consisting of a hydrogen atom, a halide, a substituted or unsubstituted alkyl group having 1 to 30 carbon atoms, a substituted or unsubstituted aryl group having 6 to 30 carbon atoms.

The present invention further discloses an organic EL device. The organic EL device may comprise an anode, a cathode and one or more organic layers formed between the anode and the cathode. At least one of the organic layers comprises the organic compound of formula (F).

DESCRIPTION OF THE PREFERRED EMBODIMENTS

What probed into the invention is the organic compound and organic EL device using the organic compound. Detailed descriptions of the production, structure and elements will be provided as follows such that the invention can be fully understood. Obviously, the application of the invention is not confined to specific details familiar to those skilled in the art. On the other hand, the common elements and procedures that are known to everyone are not described in details to avoid unnecessary limits of the invention. Some preferred embodiments of the present invention will now be described in greater detail as follows. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, an organic compound, also a heteroacene, may have the following formula (F):

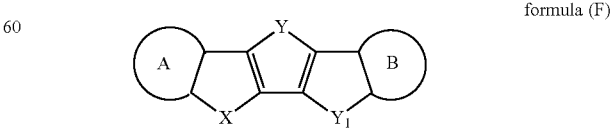

formula (F)

wherein X may be a divalent bridge selected from the group consisting of O, S, Se and $CR_1R_2$. Y may be a divalent bridge selected from the group consisting of O, S, Se and $CR_1R_2$ if $Y_1$ is N-L-Z. $Y_1$ may be a divalent bridge selected from the group consisting of O, S, Se and $CR_1R_2$ if Y is N-L-Z. A and B may independently represent a substituted or unsubstituted fused ring hydrocarbons unit having one or two rings. L may represent a single bond or a substituted or unsubstituted divalent arylene group having 6 to 30 ring carbon atoms. Z may represent a substituted or unsubstituted aryl group having 6 to 60 carbon atoms, and a substituted or unsubstituted hetroaryl group having 6 to 60 carbon atoms. $R_1$ and $R_2$ may independently be selected from the group consisting of a hydrogen atom, a halide, a substituted or unsubstituted alkyl group having 1 to 30 carbon atoms, a substituted or unsubstituted aryl group having 6 to 30 carbon atoms.

In an organic EL device, the organic compound of formula (F) may be a phosphorescent host or a fluorescent host of an emissive layer. The organic compound of formula (F) may also be an electron transport material (ETM) to form an electron transport layer (ETL), or a hole blocking material (HBM) to form a hole blocking layer (HBL) in an organic EL device.

Figure 1:
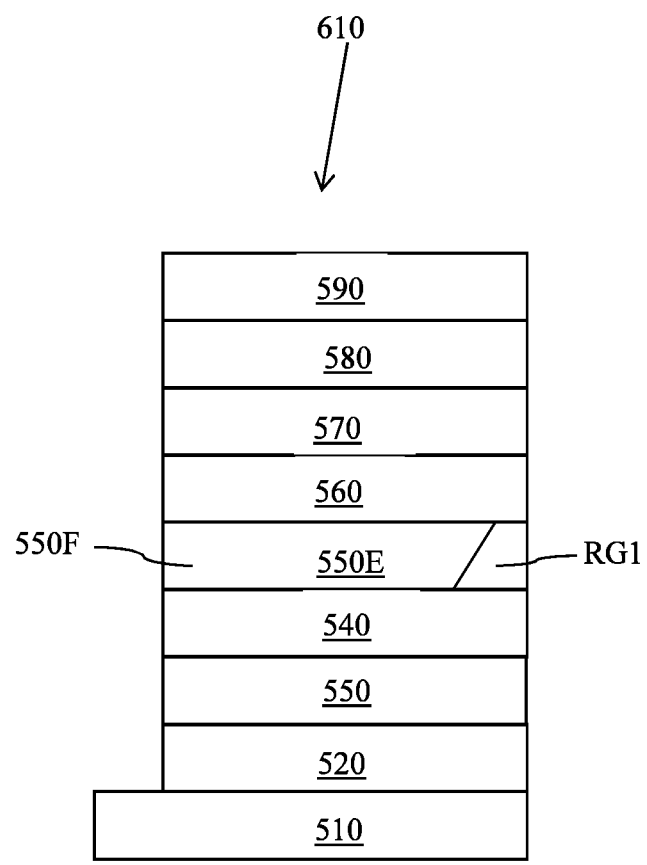
FIG. 1 is a cross-sectional view of a first organic EL device according to a second embodiment of the present invention.

In a second embodiment of the present invention, a first organic EL device using the organic compound of formula (F) is disclosed. FIG. 1 is a cross-sectional view of the first organic EL device. Referring to FIG. 1, the first organic EL device 610 may comprise the organic compound of formula (F) as a host 550F of an emissive layer 550E.

Figure 2:
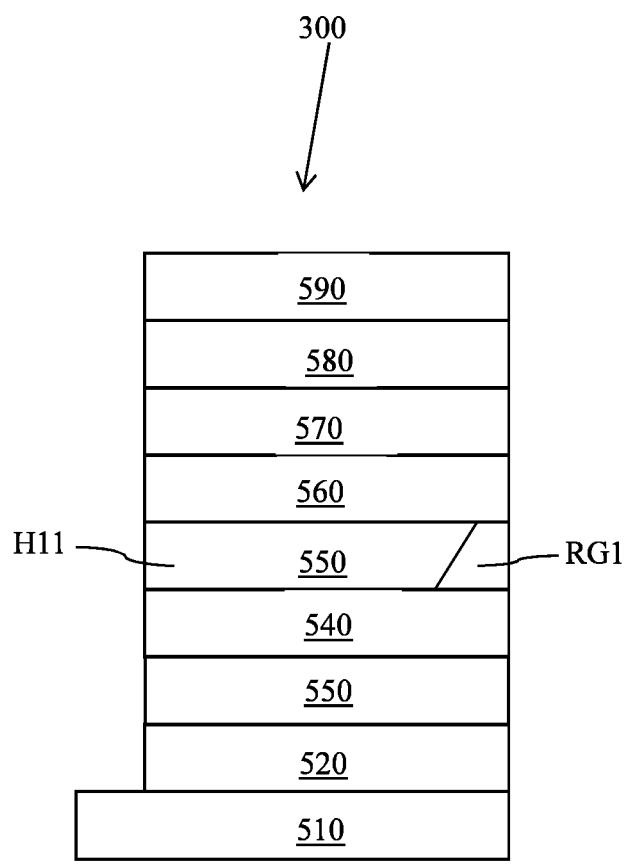
FIG. 2 is a cross-sectional view of an organic EL device without the host 340C of FIG. 1.

FIG. 2 is a cross-sectional view of an organic EL device without the organic compound of formula (F) (without 550F of FIG. 1). Referring to FIG. 2, the organic EL device 300 may have a driving voltage of about 4.3 V, a current efficiency of about 17.5 cd/A, or a half-life of about 800 hours.

Referring to FIG. 1, by comprising the organic compound of formula (F) as the host 550C, the first organic EL device 610 may have a driving voltage lower than that of the organic EL device 300 (FIG. 2). Moreover, by comprising the organic compound of formula (F) as the host 550C, the first organic EL device 610 of FIG. 1 may have a current efficiency higher than that of the organic EL device 300 (FIG. 2). Furthermore, by comprising the organic compound of formula (F) as the host 550C, the first organic EL device 610 of FIG. 1 may have a half-life longer than that of the organic EL device 300 (FIG. 2).

Still referring to FIG. 1, as the host 550C of the first organic EL device 610 of FIG. 1, the organic compound of formula (F) may lower the driving voltage to be about 3.5 V to about 4.7 V. Moreover, the organic compound of formula (F) may increase the current efficiency to be 19.0 cd/A to about 29.3 cd/A. Furthermore, the organic compound of formula (F) may increase the half-life to be about 700 hours to about 1350 hours.

Figure 3:
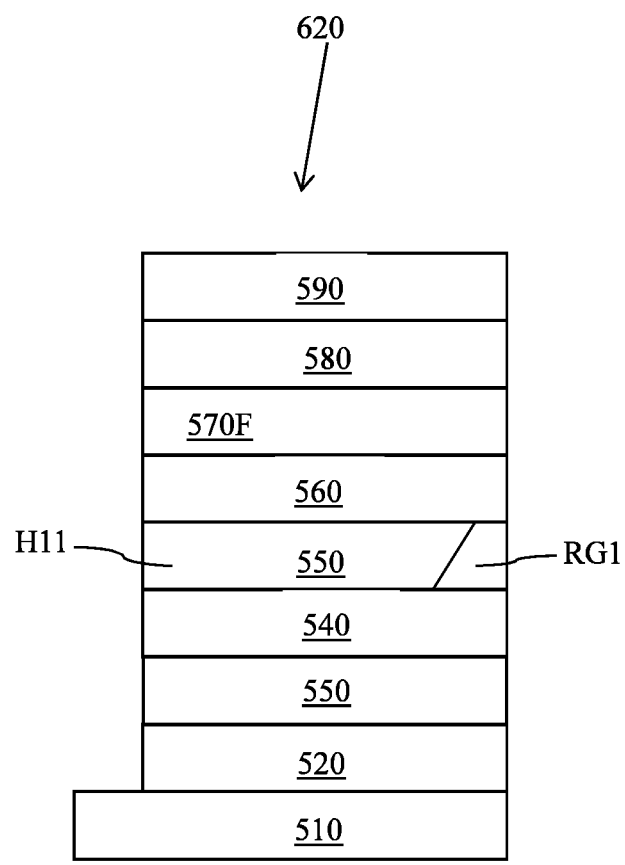
FIG. 3 is a cross-sectional view of a second organic EL device according to a third embodiment of the present invention.

FIG. 3 is a cross-sectional view of the second organic EL device in a third embodiment of the present invention. Referring to FIG. 3, a second organic EL device 620 using the organic compound of formula (F) is disclosed. The second organic EL device 620 may comprise the organic compound of formula (F) as an electron transport layer 570F.

FIG. 2 is a cross-sectional view of an organic EL device without the organic compound of formula (F) (without 570F of FIG. 3). Referring to FIG. 2, the organic EL device 300 may have a driving voltage of about 4.3 V, a current efficiency of about 17.5 cd/A, or a half-life of about 800 hours.

Referring to FIG. 3, by comprising the organic compound of formula (F) as the electron transport layer 570F, the second organic EL device 620 may have a driving voltage lower than that of the organic EL device 300 (FIG. 2). Moreover, by comprising the organic compound of formula (F) as electron transport layer 570F, the second organic EL device 620 of FIG. 3 may have a current efficiency higher than that of the organic EL device 300 (FIG. 2). Furthermore, by comprising the organic compound of formula (F) as the electron transport layer 570F, the second organic EL device 520 of FIG. 3 may have a half-life longer than that of the organic EL device 300 (FIG. 2).

Referring to FIG. 3, as the electron transport layer 570F of the second organic EL device 620, the organic compound of formula (F) may lower the driving voltage to be about 3.9 V to about 4.4 V. Moreover, the organic compound of formula (F) may increase the current efficiency to be about 17.3 cd/A to about 19.0 cd/A. Furthermore, the organic compound of formula (F) may increase the half-life to be about 780 hours to about 970 hours.

Figure 4:
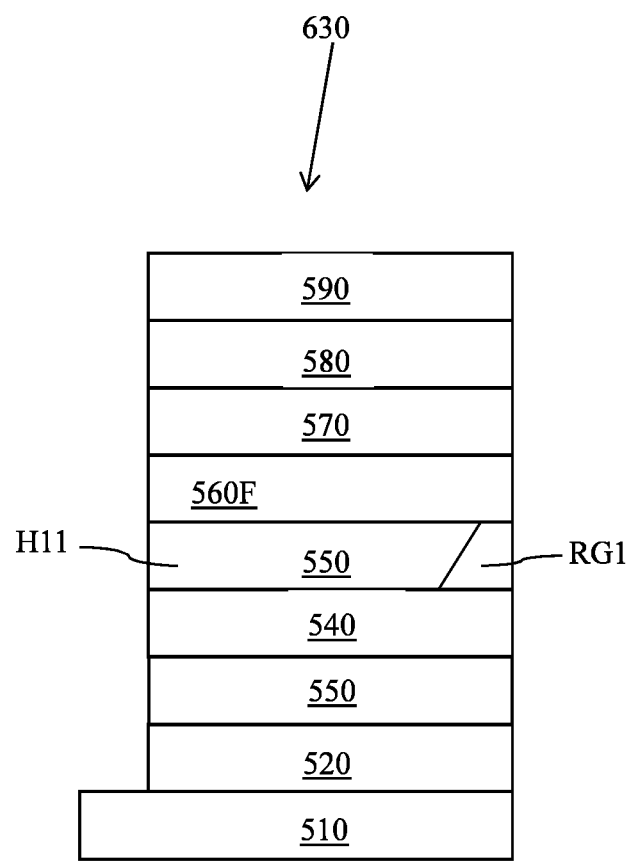
FIG. 4 is a cross-sectional view of a third organic EL device according to a fourth embodiment of the present invention.

FIG. 2 is a cross-sectional view of an organic EL device without the organic compound of formula (F) (without 560F of FIG. 4). Referring to FIG. 2, the organic EL device 300 may have a driving voltage of about 4.3 V, a current efficiency of about 17.5 cd/A, or a half-life of about 800 hours.

Referring to FIG. 4, by comprising the organic compound of formula (F) as the hole blocking layer 560F, the third organic EL device 630 may have a driving voltage lower than that of the organic EL device 300 (FIG. 2). Moreover, by comprising the organic compound of formula (F) as the hole blocking layer 560F, the second organic EL device 620 of FIG. 3 may have a current efficiency higher than that of the organic EL device 300 (FIG. 2). Furthermore, by comprising the organic compound of formula (F) as the e hole blocking layer 560F, the second organic EL device 520 of FIG. 3 may have a half-life longer than that of the organic EL device 300 (FIG. 2).

Referring to FIG. 3, as the hole blocking layer 560F of the third organic EL device 630, the organic compound of formula (F) may lower the driving voltage to be bout 4.0 V to about 4.5 V. Moreover, the organic compound of formula (F) may increase the current efficiency to be about 17.0 cd/A to about 18.5 cd/A. Furthermore, the organic compound of formula (F) may increase the half-life to be about 760 hours to about 910 hours.

In formula (F), L may be selected from the group consisting of:

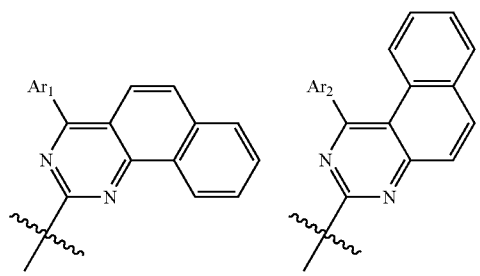

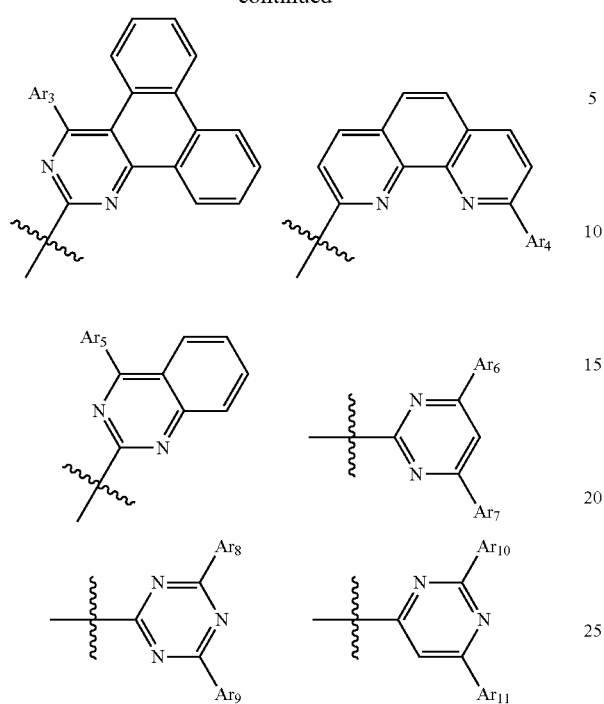
wherein $Ar_1$ to $Ar_{11}$ may independently represent a hydrogen atom, a substituted or unsubstituted aryl group having 6 to 30 carbon atoms, or a substituted or unsubstituted hetroaryl group having 6 to 30 carbon atoms.
In formula (F), Z may represent one of the following substituents:
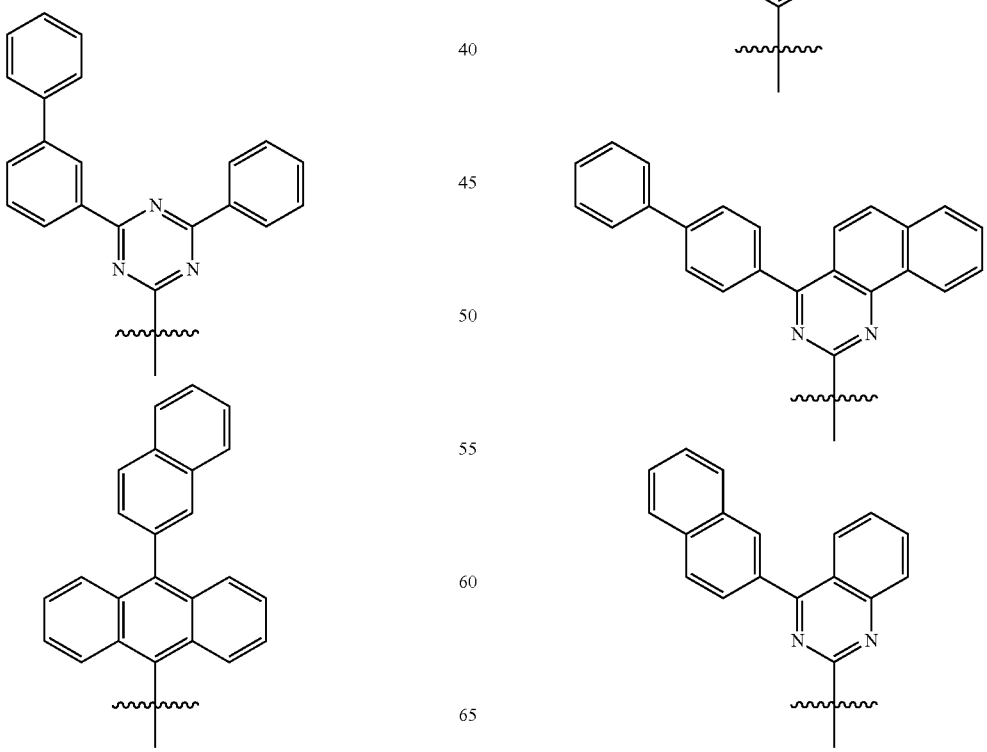
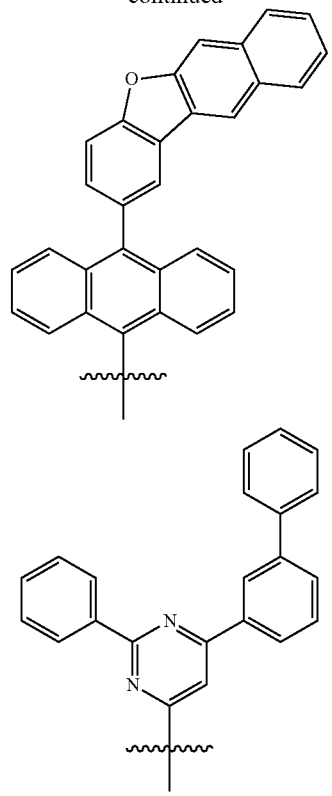
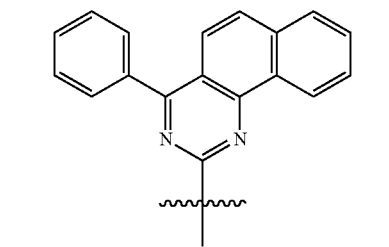
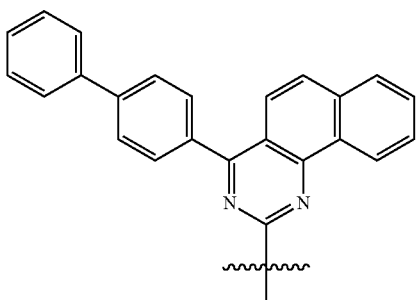

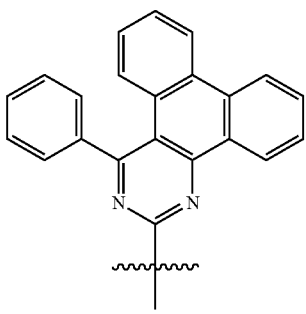
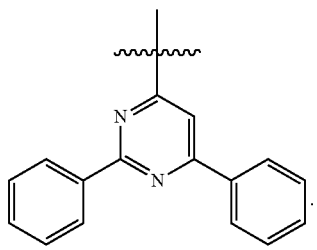
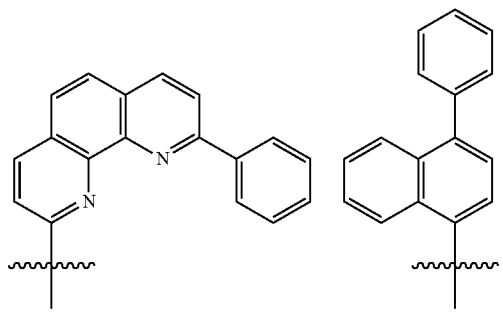
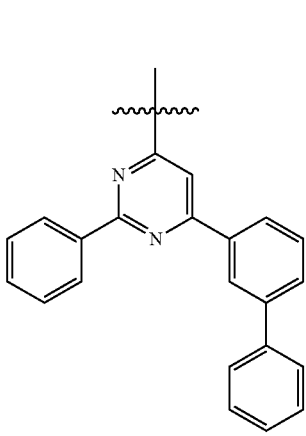
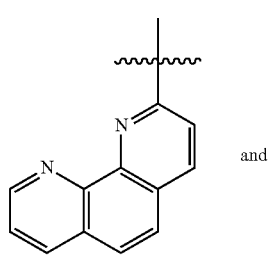
and
The organic compound of the present invention may have the following formula (1) or formula (2):
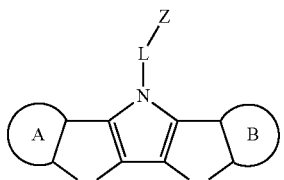
formula (1)
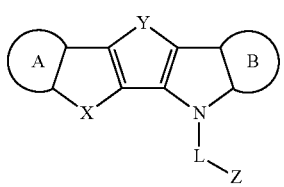
formula (2)
The organic compound of the present invention may also have one of formula (3) to formula (7):
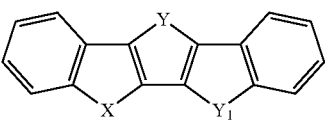
formula (3)
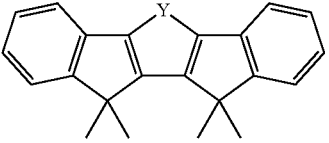
formula (4)
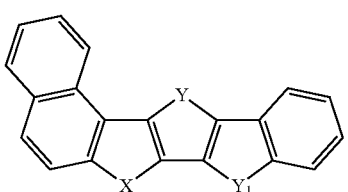
formula (5)
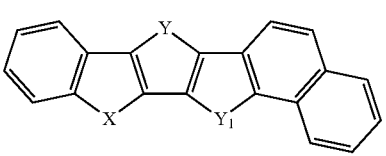
formula (6)
and -continued
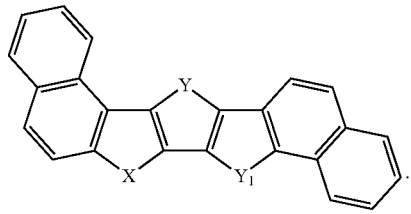
formula (7)
In formula (1) to formula (7), the same definition as described in paragraph [0013] to paragraph [0027].
The organic compound of the present invention may has one of the following formulas:
EX1
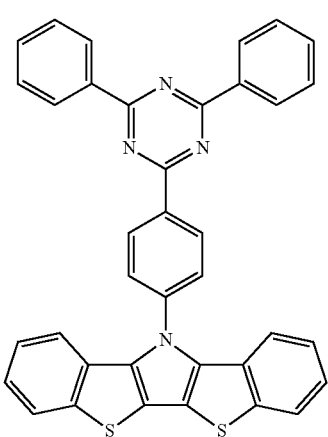
EX2
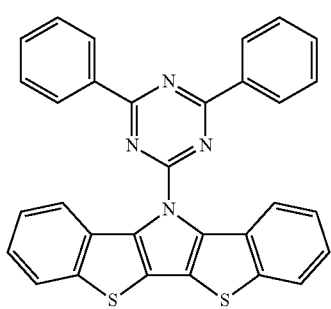
EX3
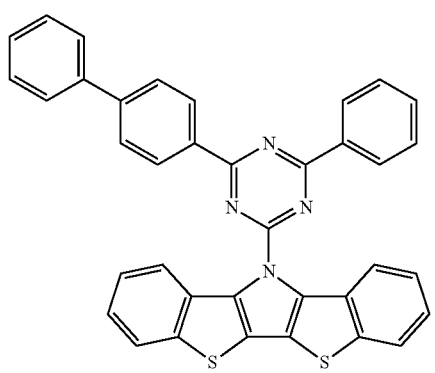
-continued
EX4
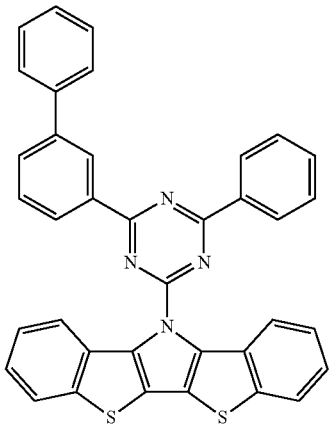
EX5
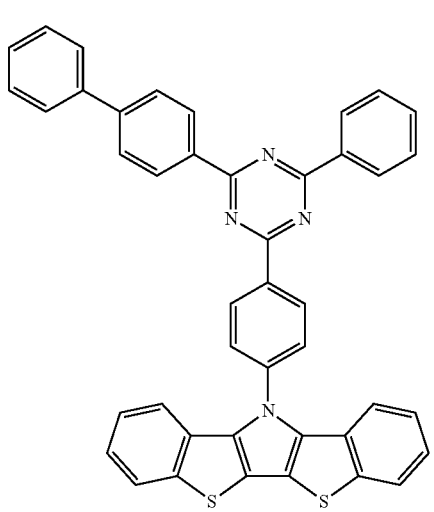
EX6
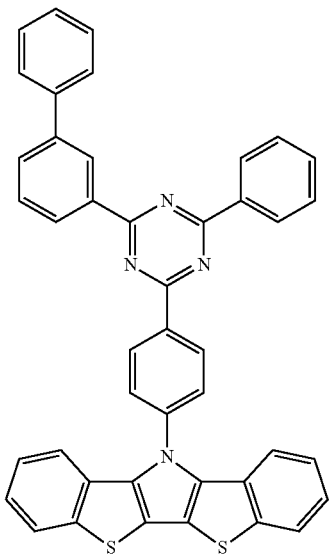

-continued
EX7
EX8
EX9
EX10
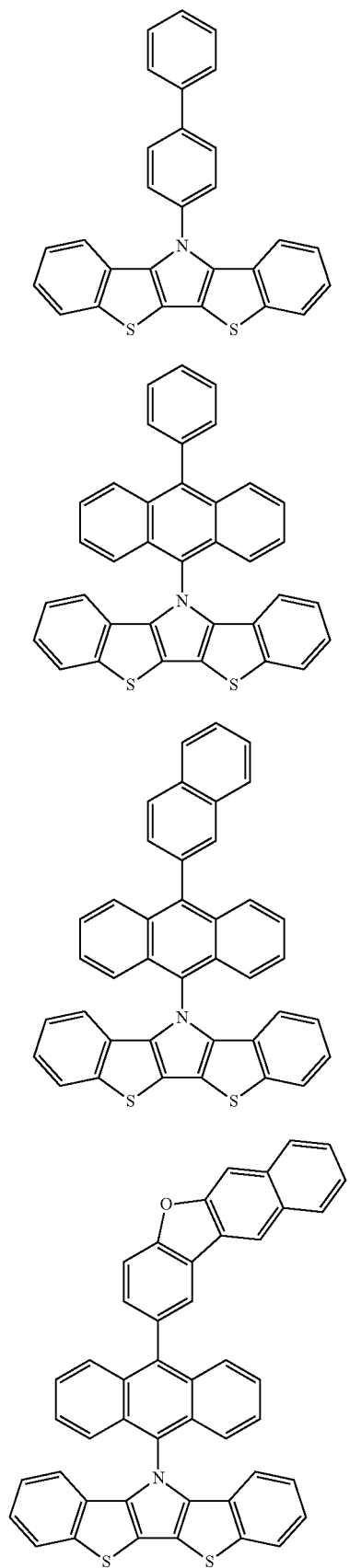
-continued
EX11
EX12
EX13
EX14
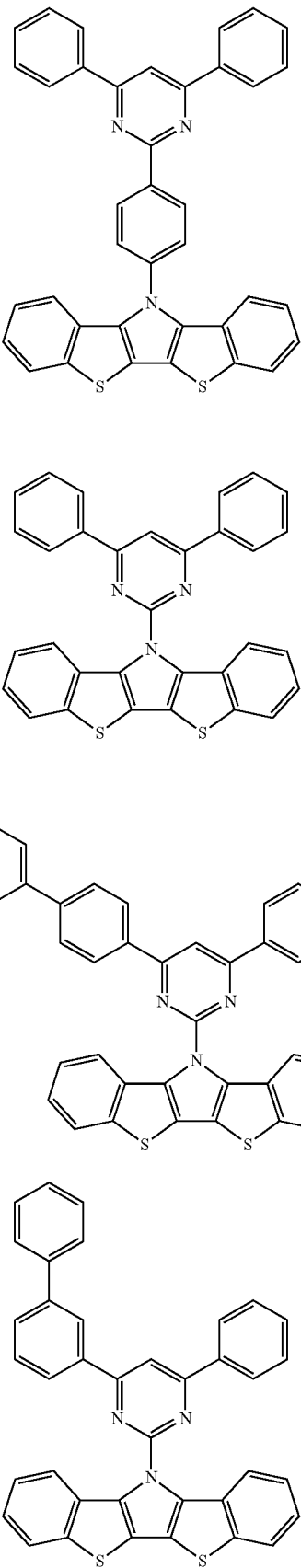

EX15
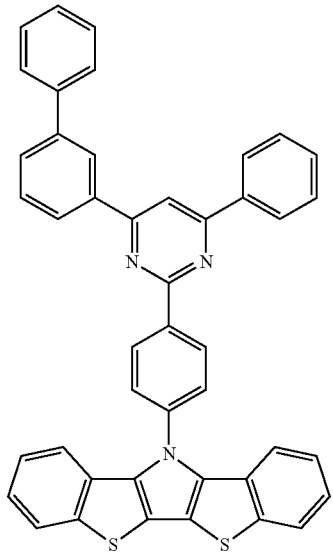
EX16
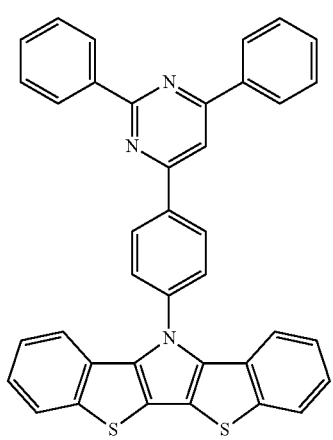
EX17
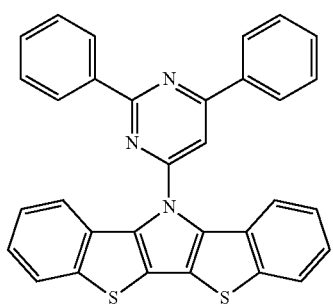
EX18
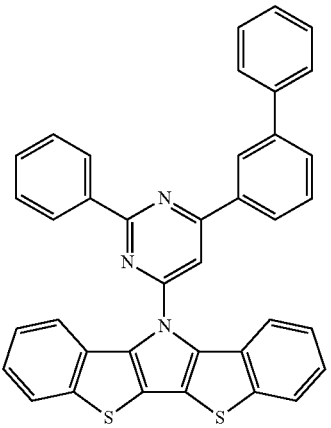
EX19
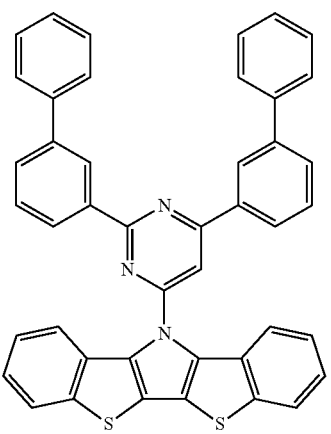
EX20
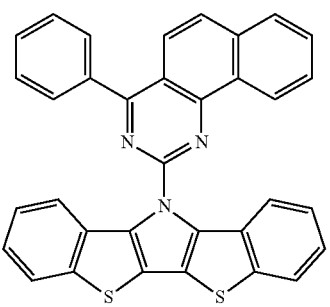
EX21
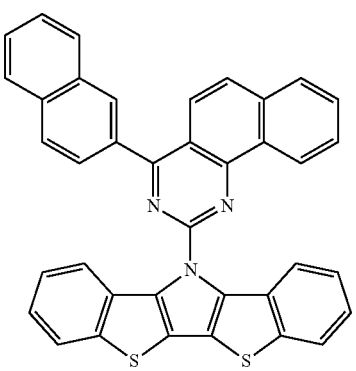

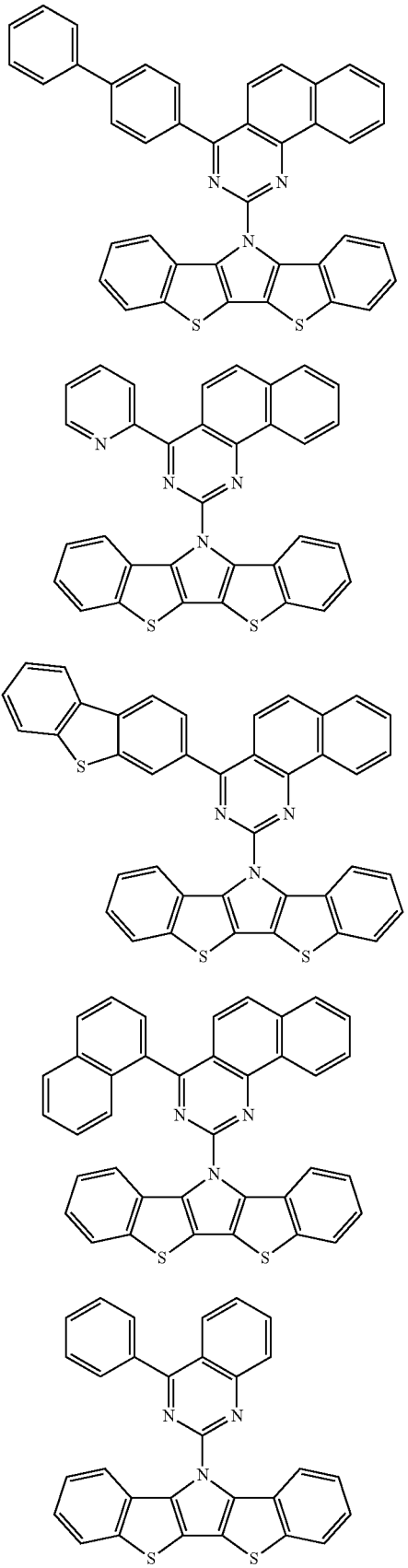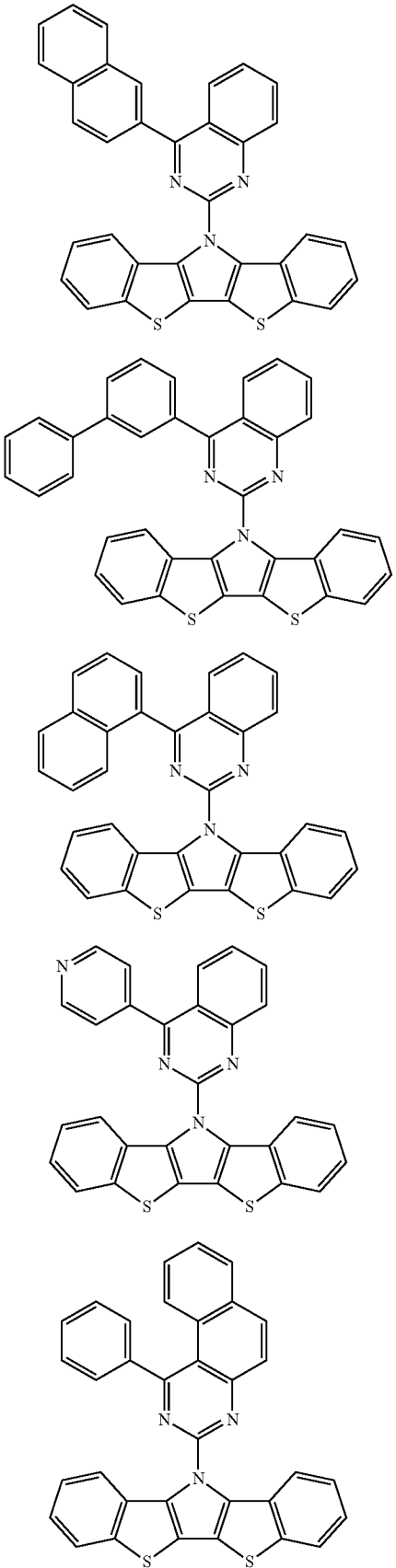

EX32
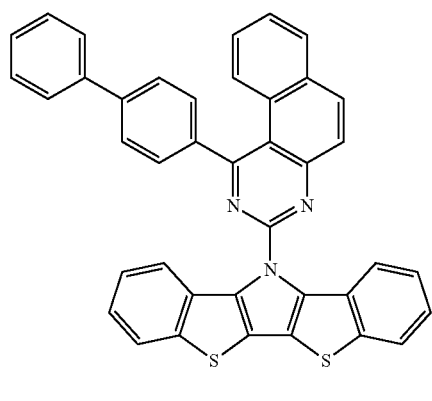
EX33
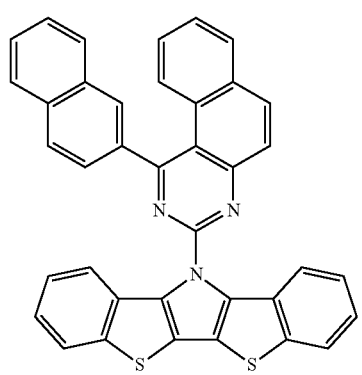
EX34
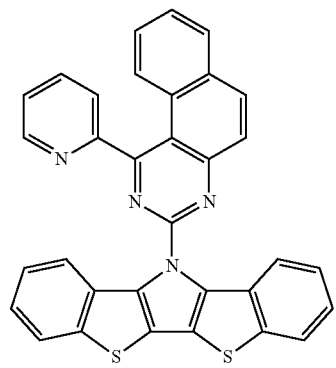
EX35
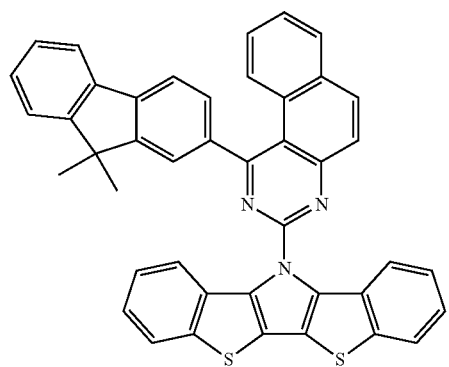
EX36
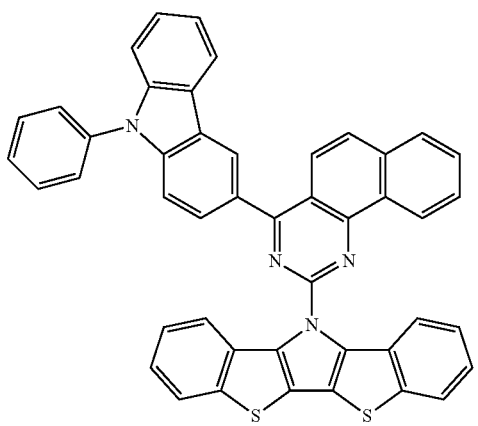
EX37
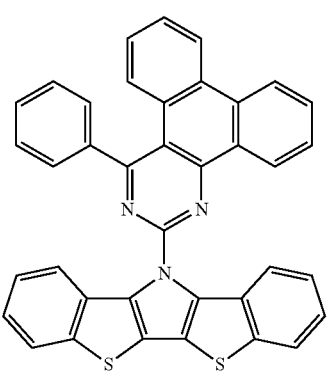
EX38
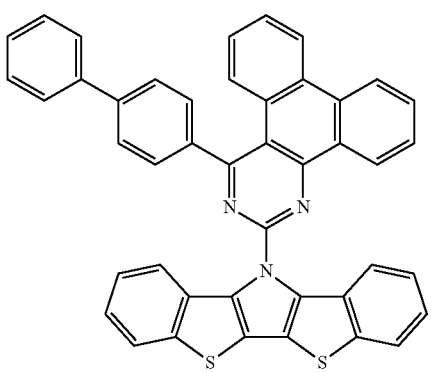
EX39
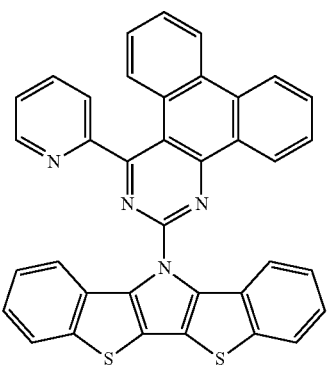

EX40
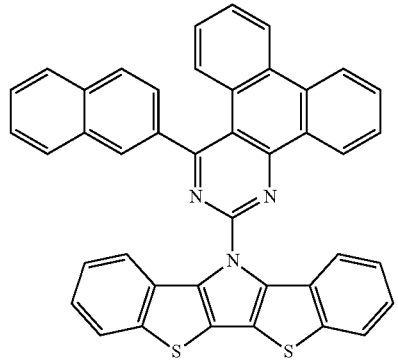
EX41
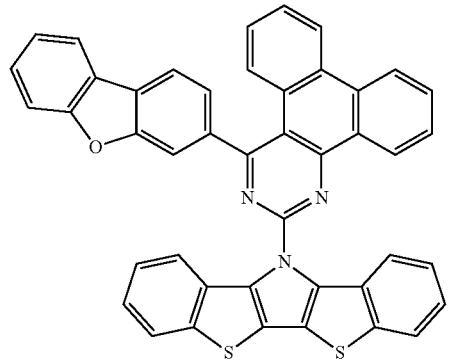
EX42
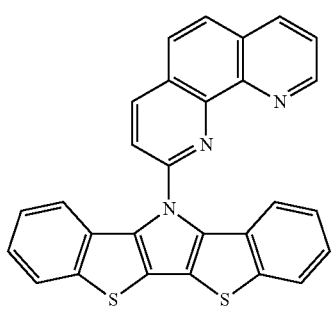
EX43
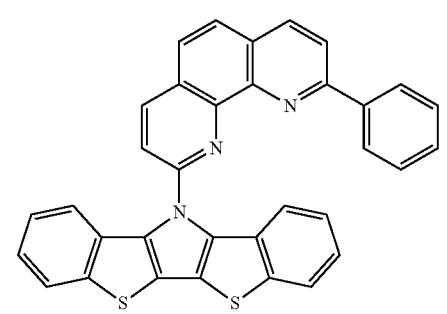
EX44
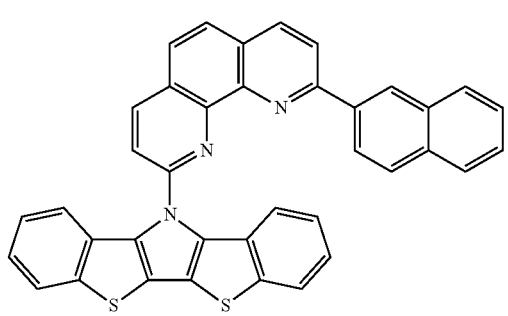
EX45
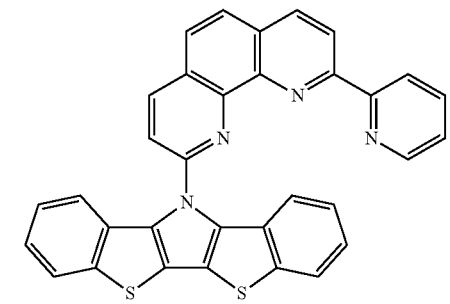
EX46
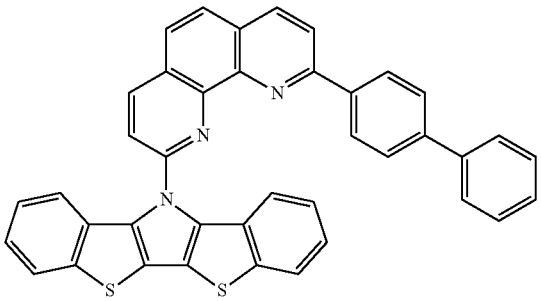
EX47
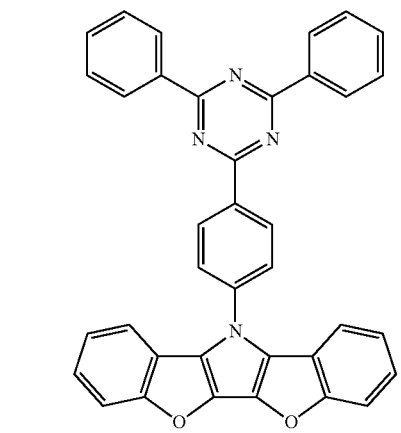

-continued
EX48
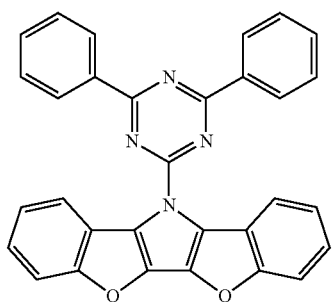
EX49
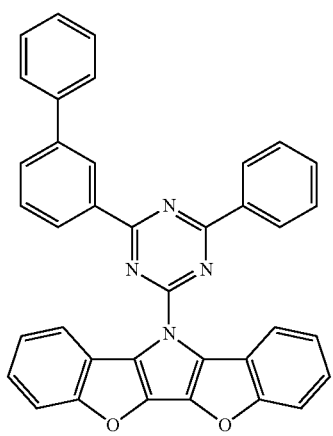
EX50
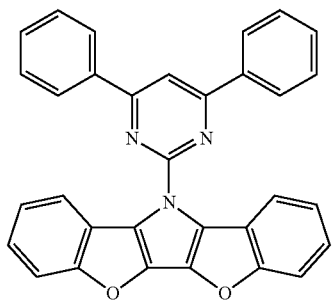
EX51
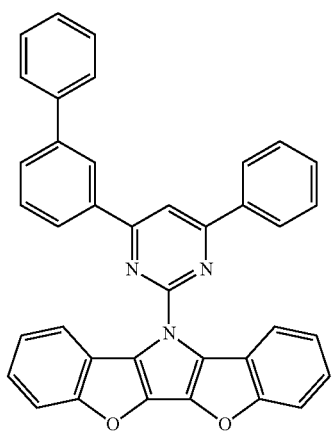
EX52
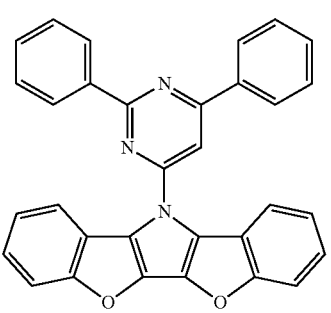
EX53
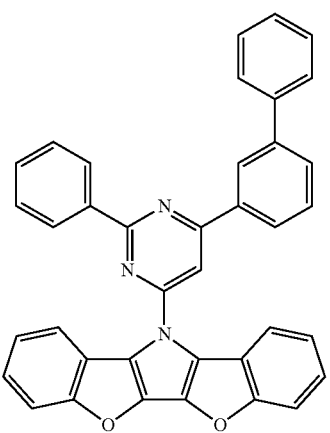
EX54
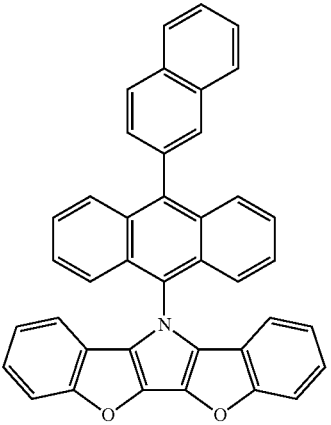
EX55
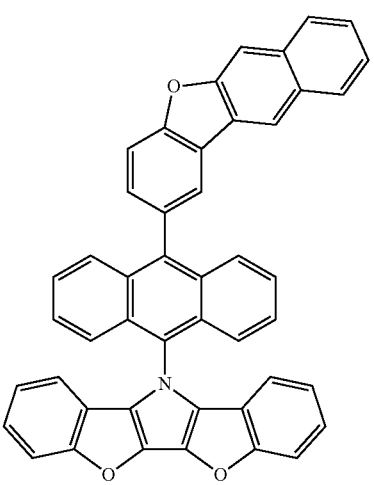

-continued
EX56
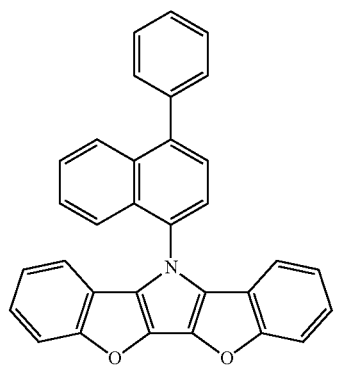
EX57
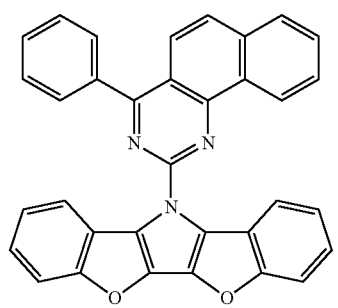
EX58
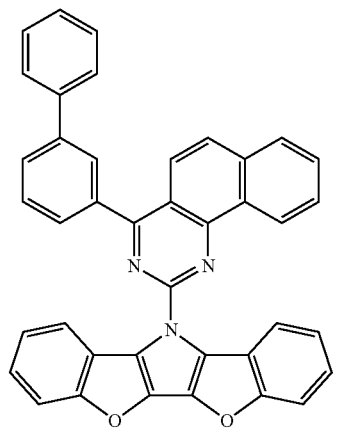
EX59
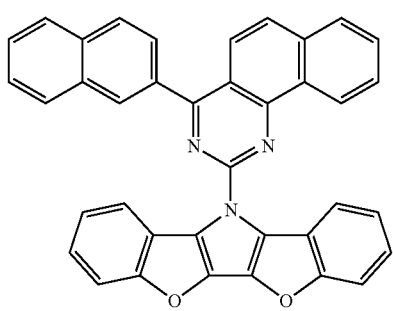
-continued
EX60
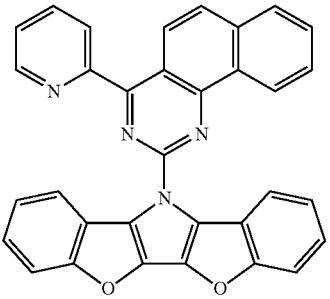
EX61
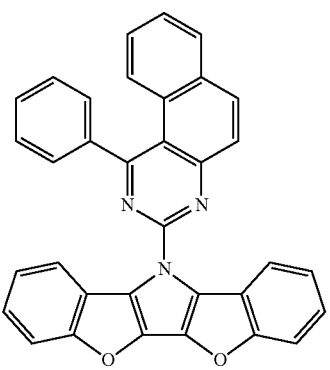
EX62
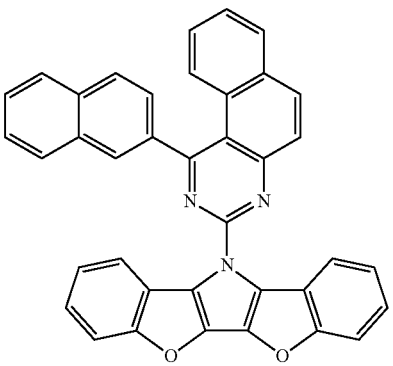
EX63
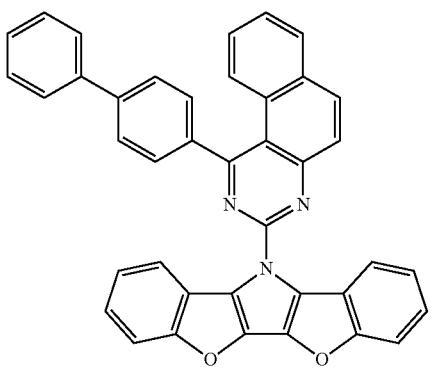

EX64
EX65
EX66
EX67
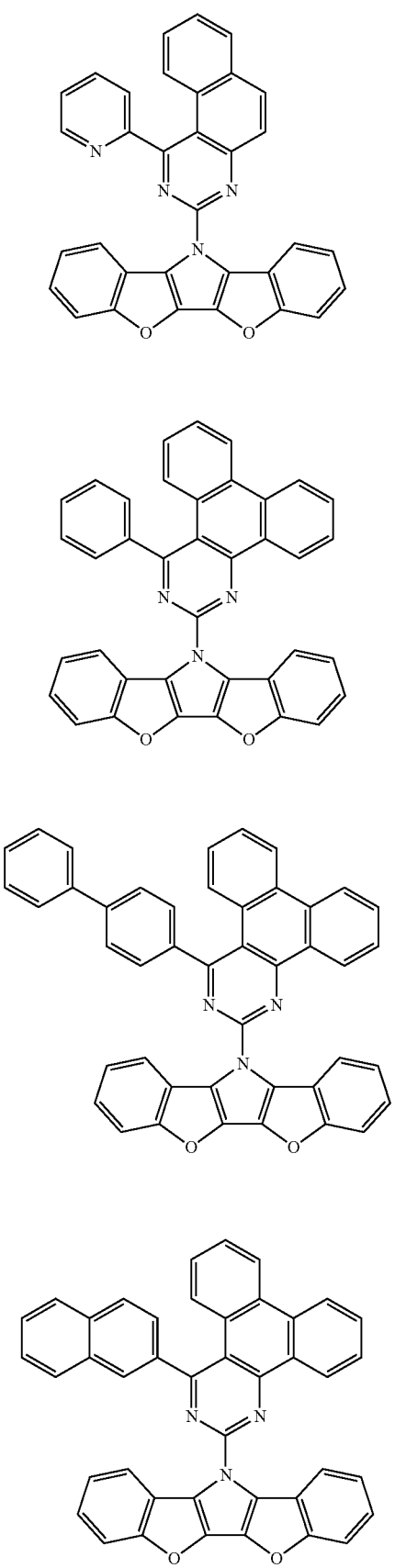
EX68
EX69
EX70
EX71
EX72
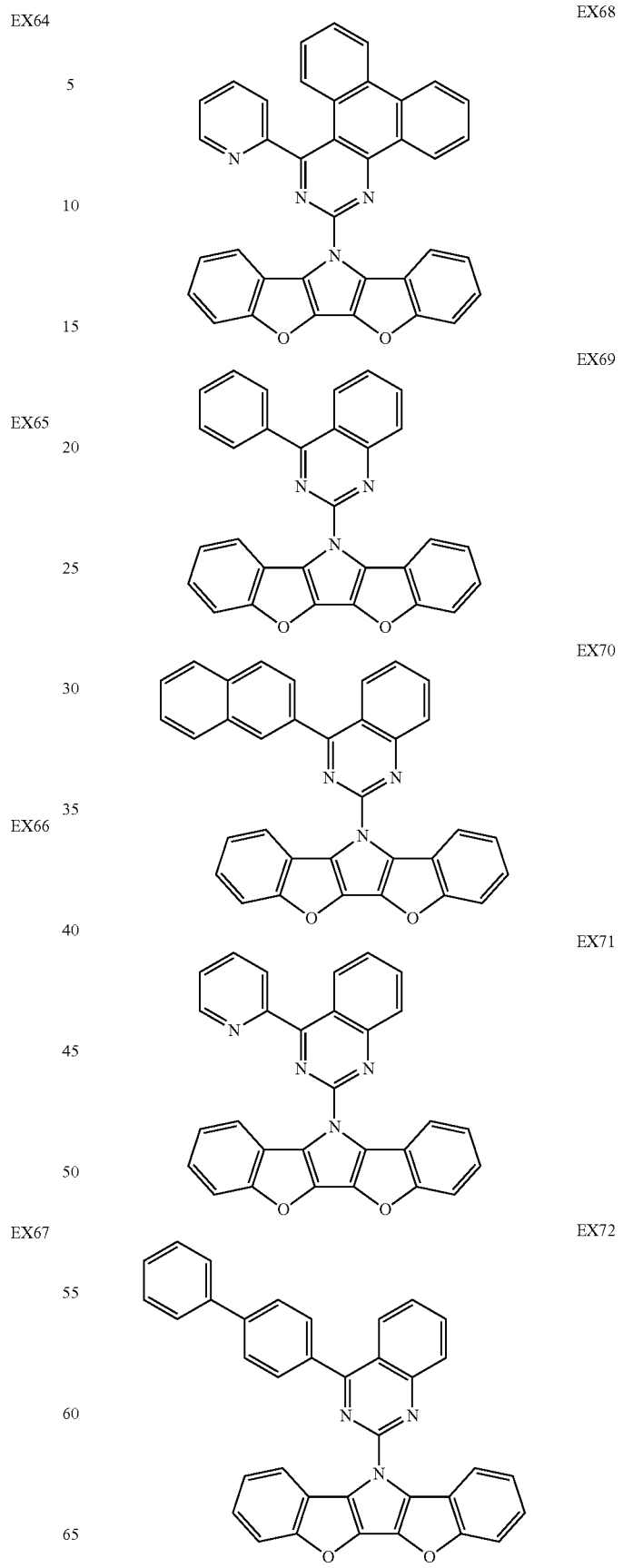

EX73
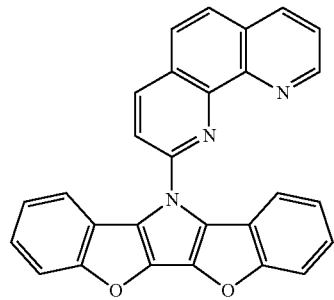
EX74
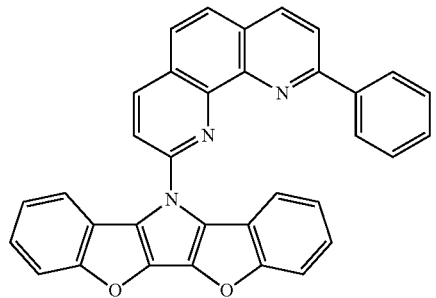
EX75
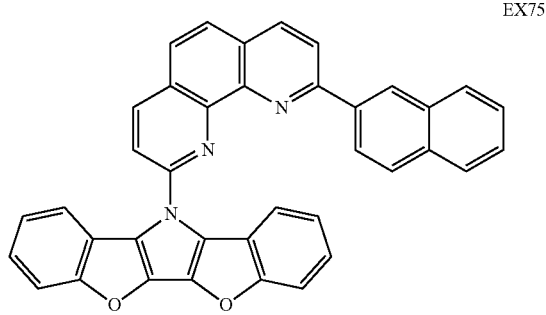
EX76
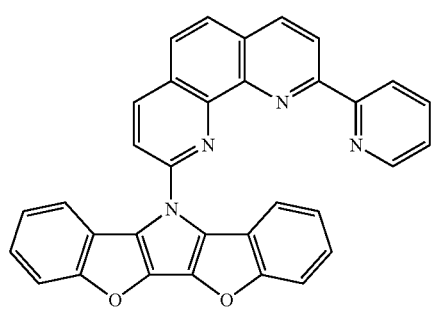
EX77
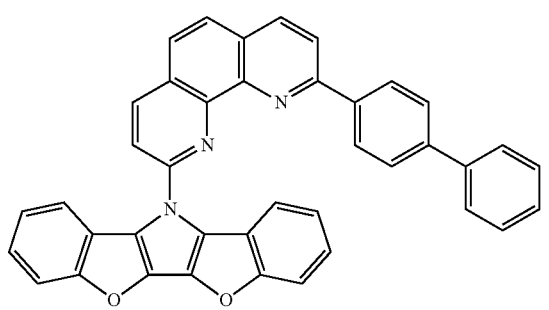
EX78
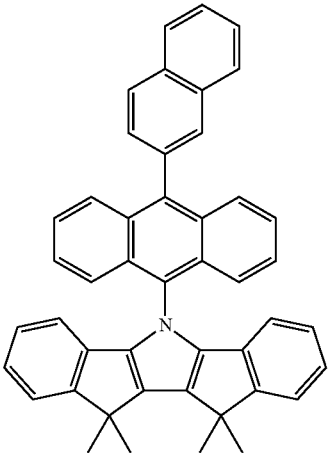
EX79
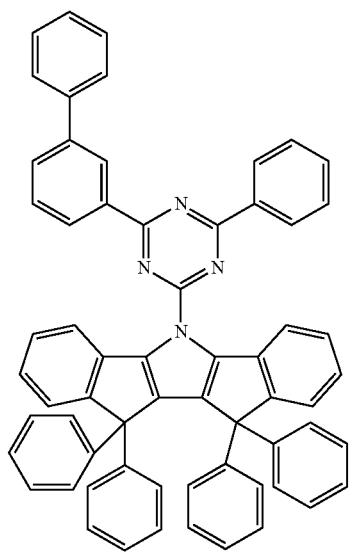
EX80
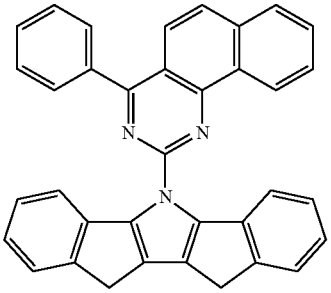

EX81
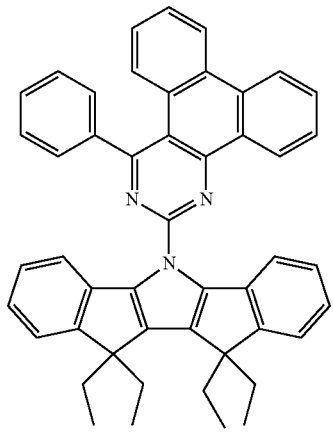
EX82
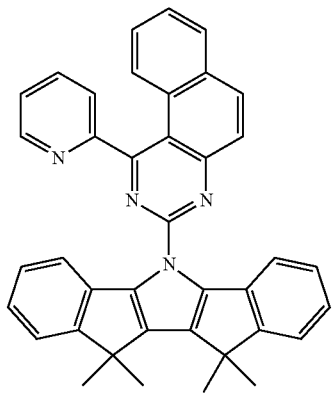
EX83
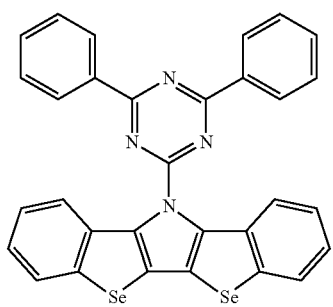
EX84
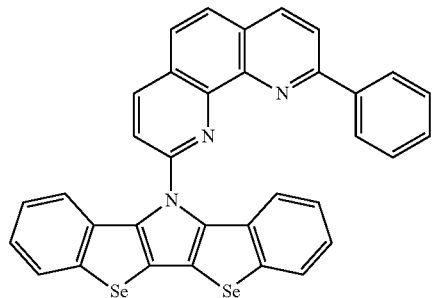
EX85
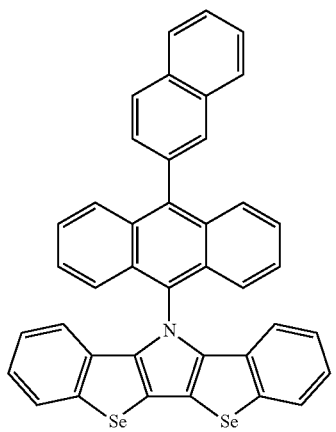
EX86
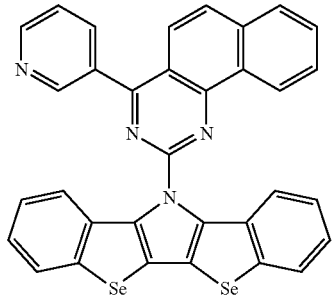
EX87
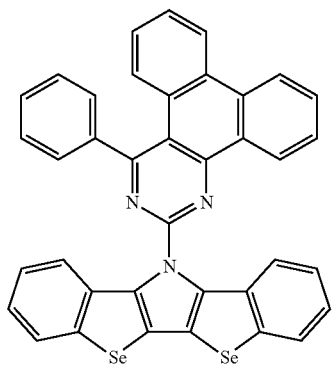
EX88
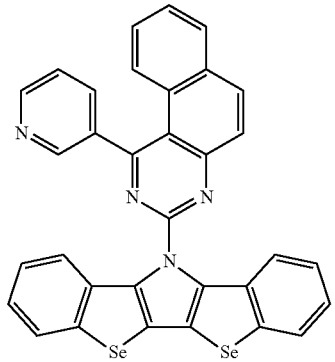

-continued
EX89
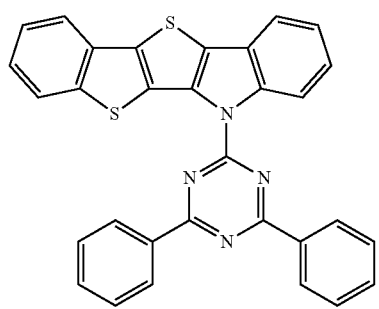
EX90
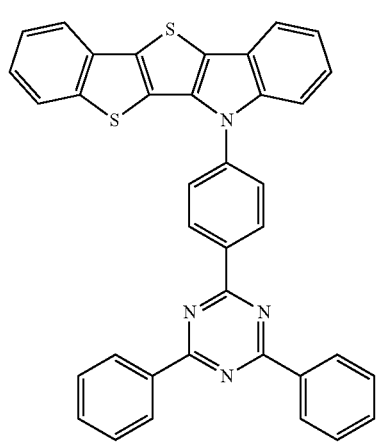
EX91
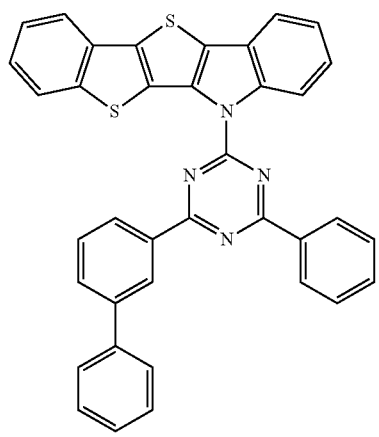
EX92
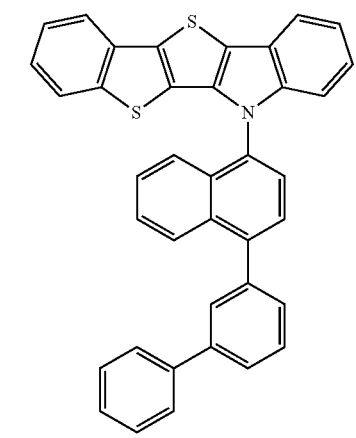
-continued
EX93
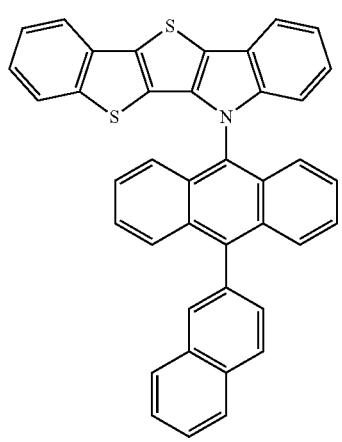
EX94
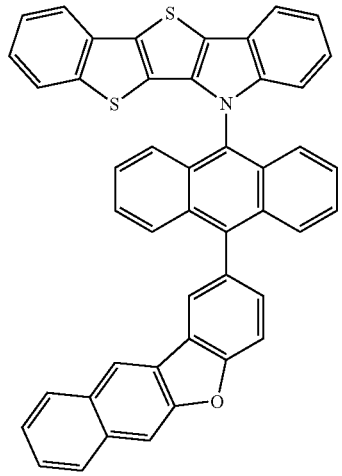
EX95
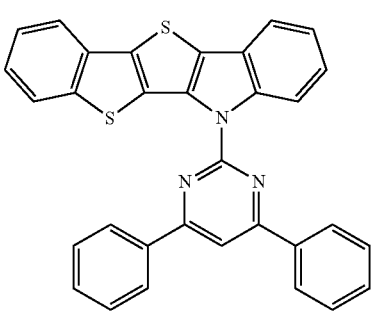
EX96
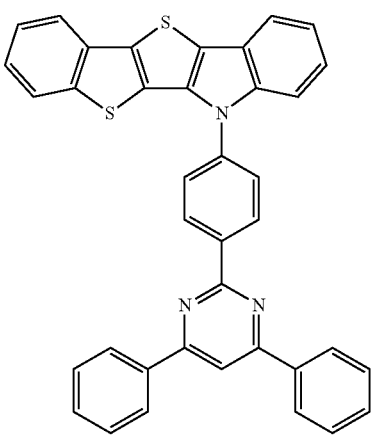

EX97
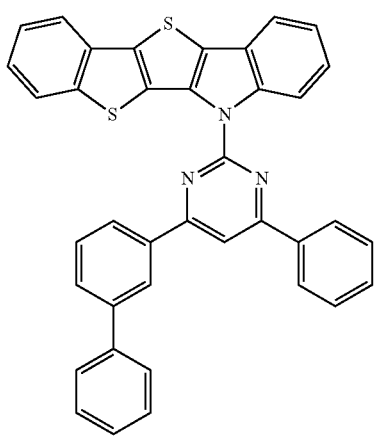
EX98
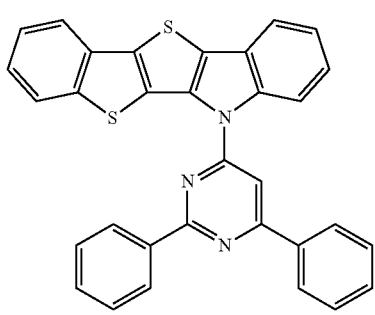
EX99
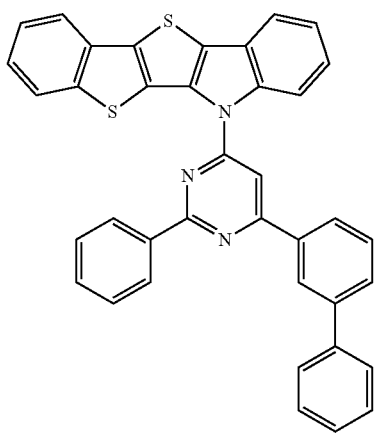
EX100
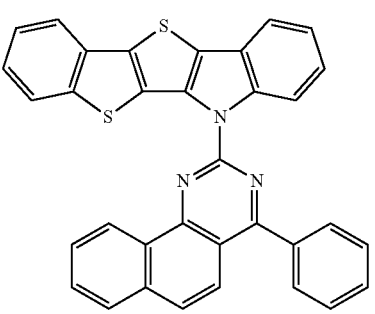
EX101
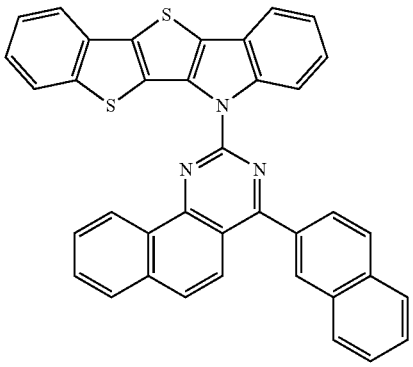
EX102
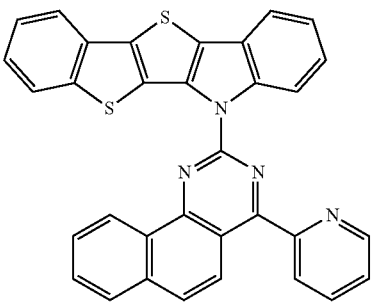
EX103
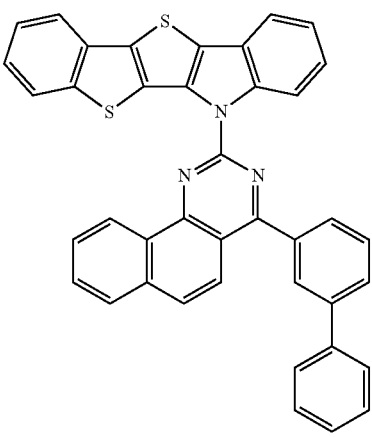
EX104
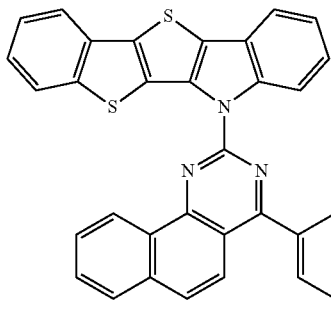

EX105
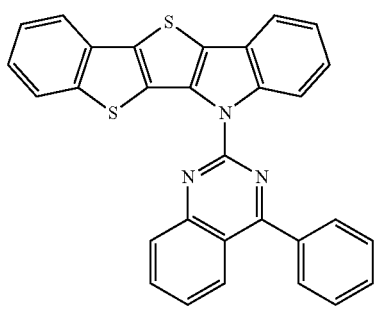
EX106
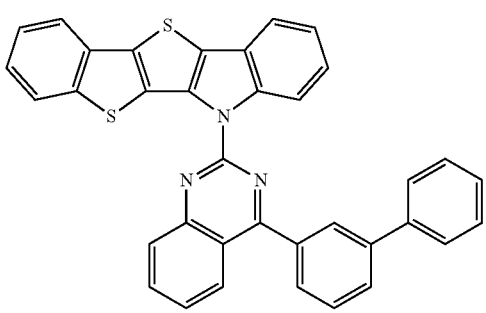
EX107
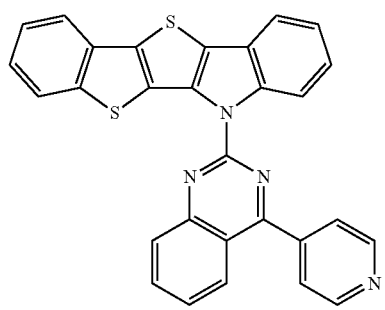
EX108
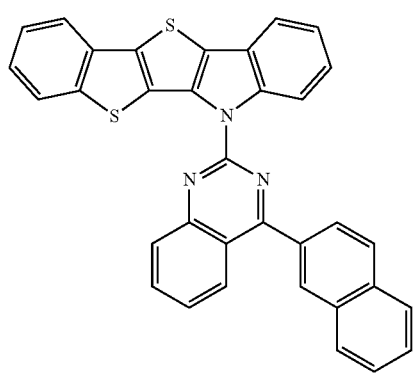
EX109
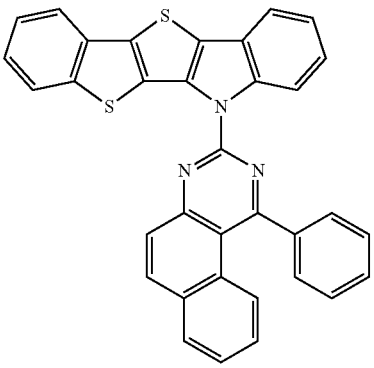
EX110
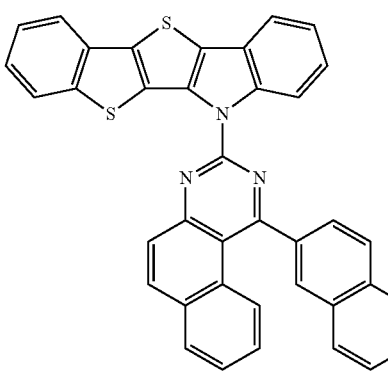
EX111
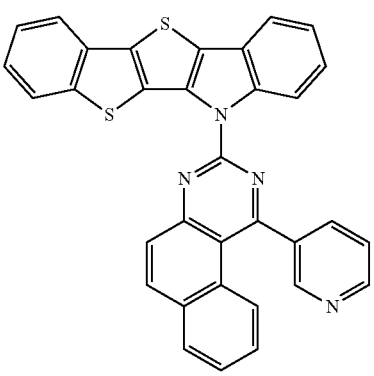
EX112
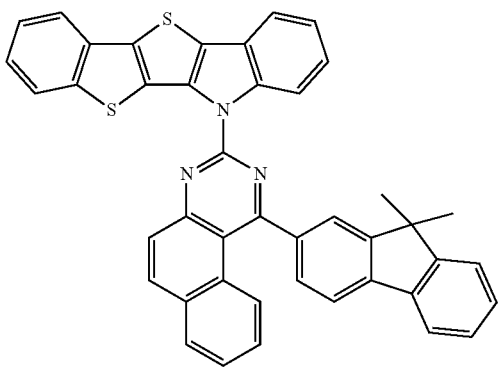

EX113
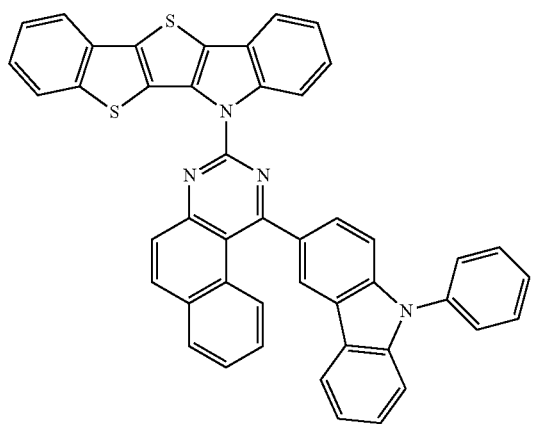
EX114
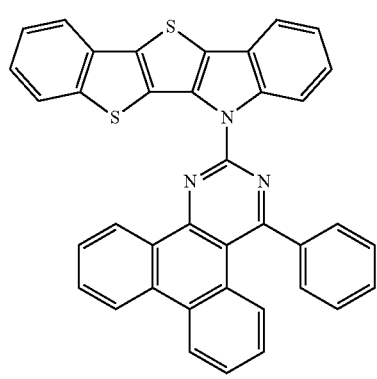
EX115
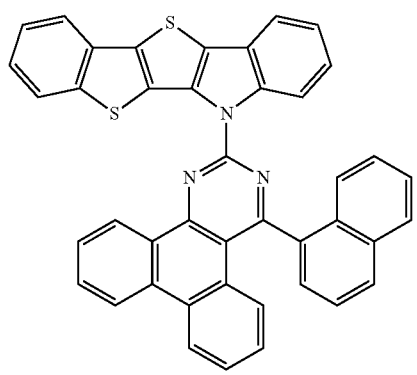
EX116
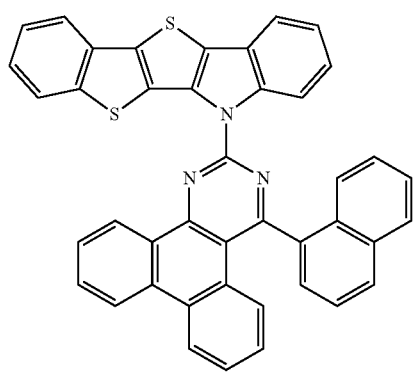
EX117
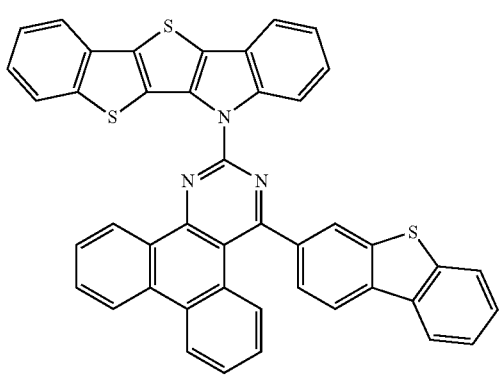
EX118
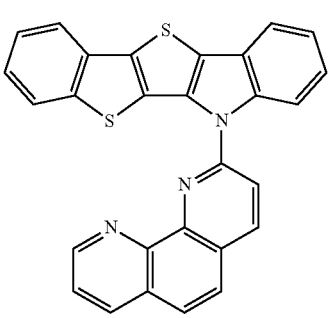
EX119
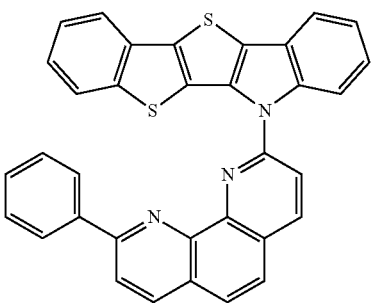
EX120
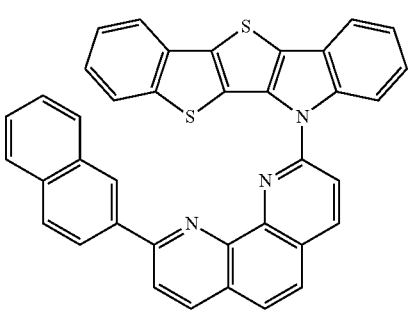
EX121
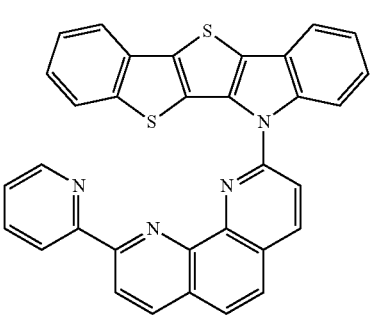

EX122
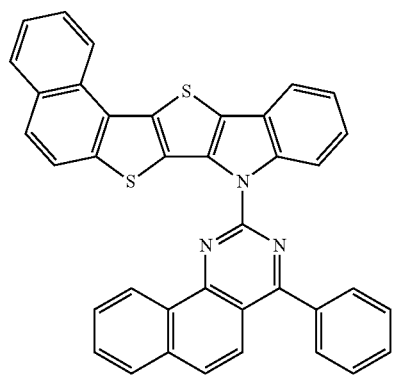
EX123
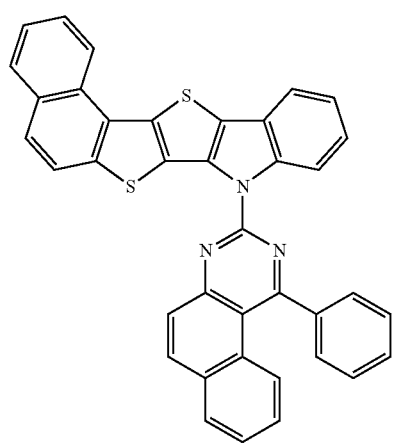
EX124
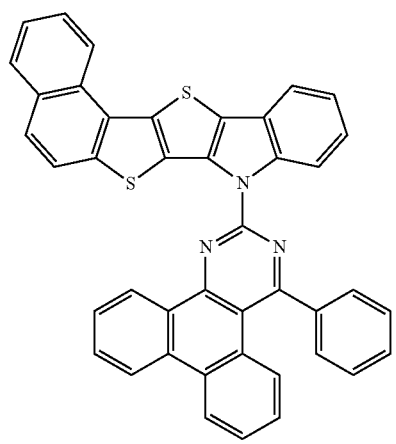
EX125
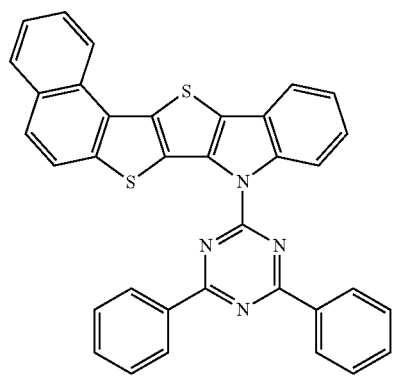
EX126
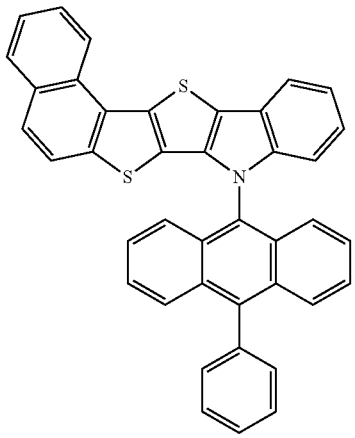
EX127
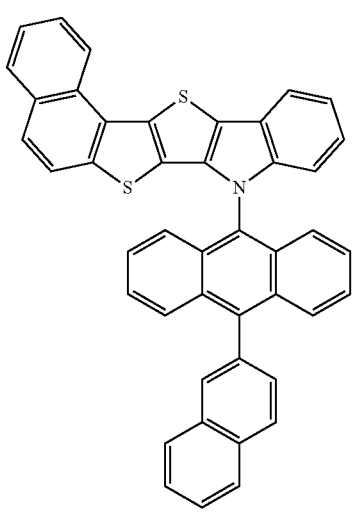
EX128
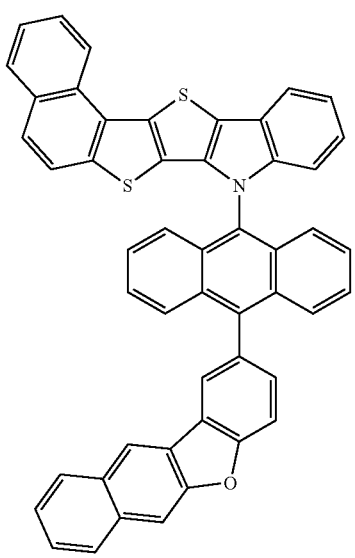

EX129
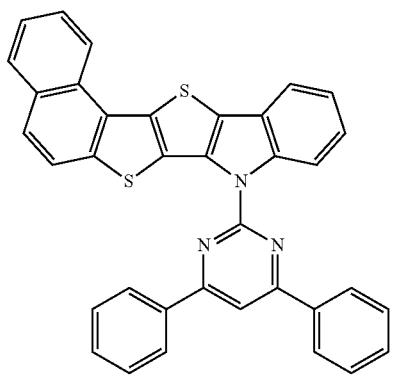
EX130
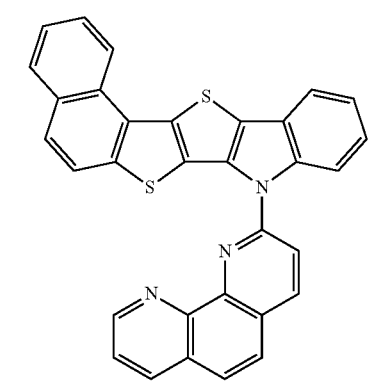
EX131
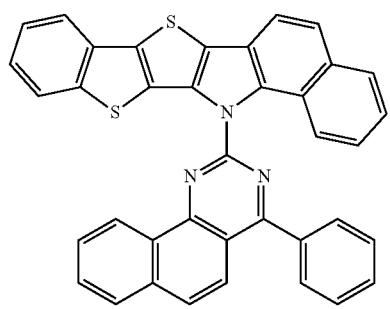
EX132
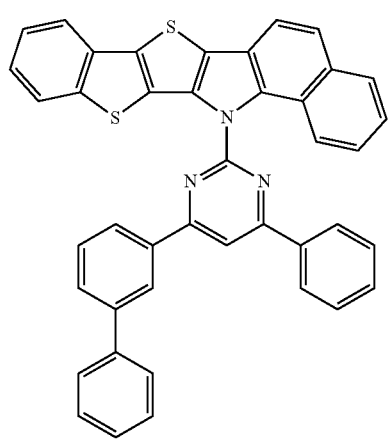
EX133
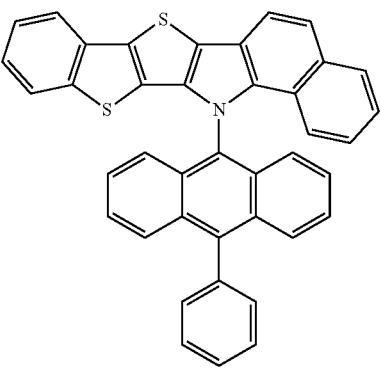
EX134
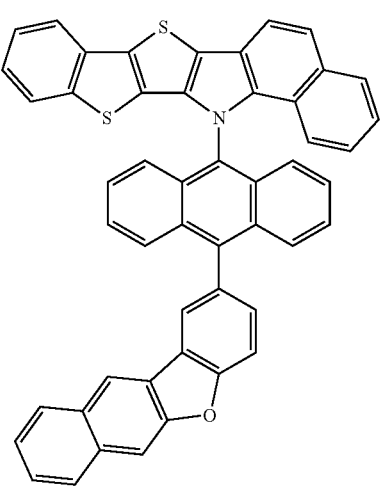
EX135
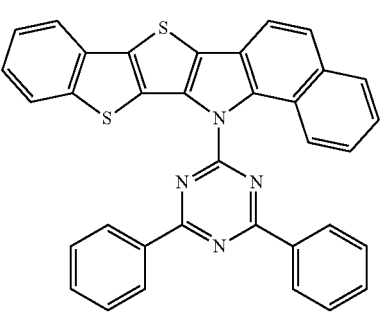
EX136
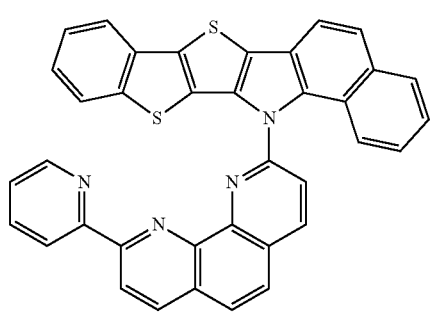

EX137
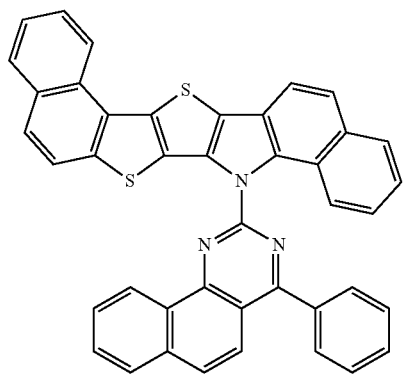
EX138
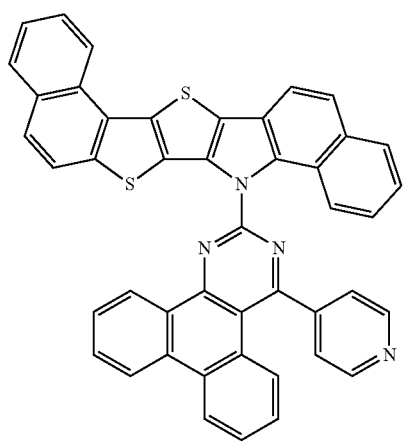
EX139
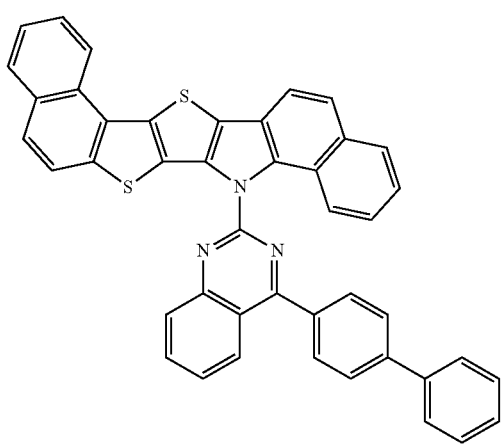
EX140
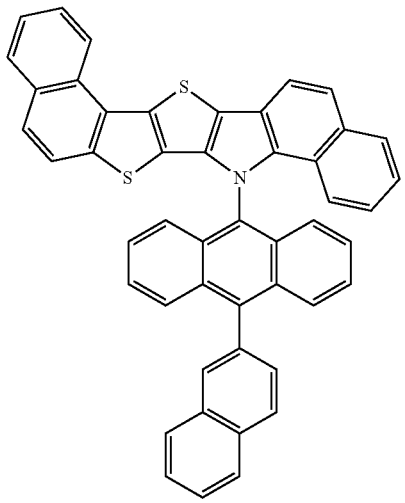
EX141
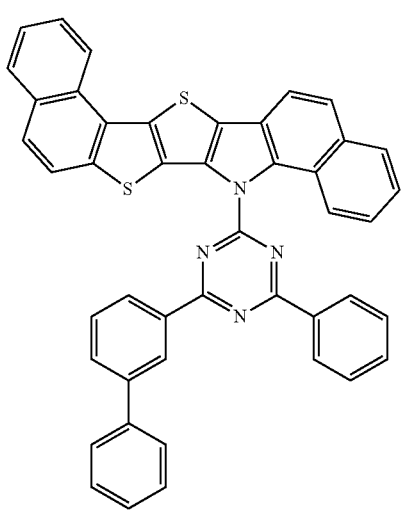
EX142
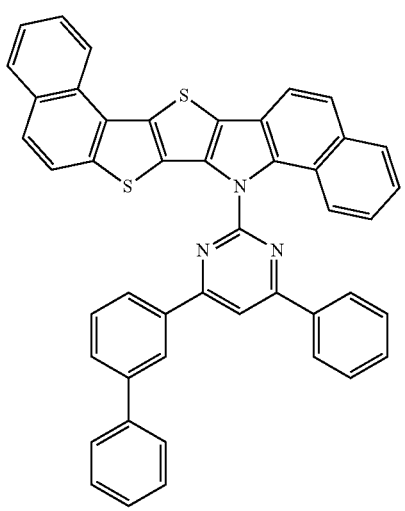

EX143
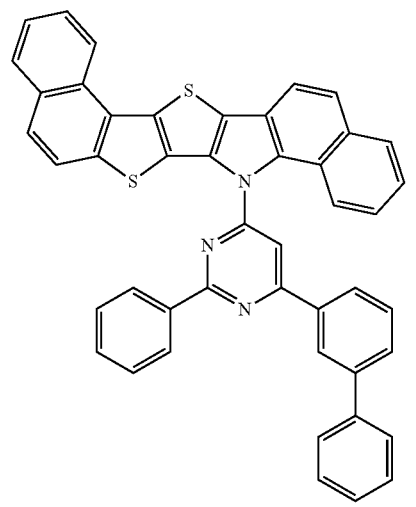
EX144
EX145
EX146
EX147
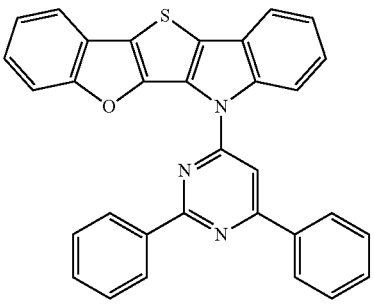
EX148
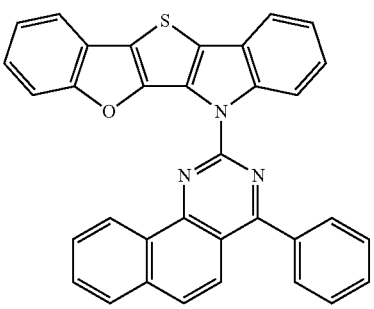
EX149
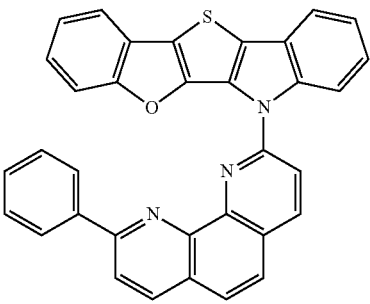
EX150
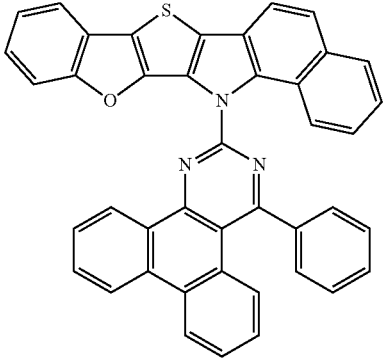

-continued
EX151
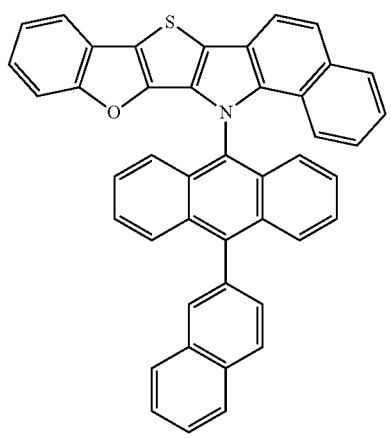
EX152
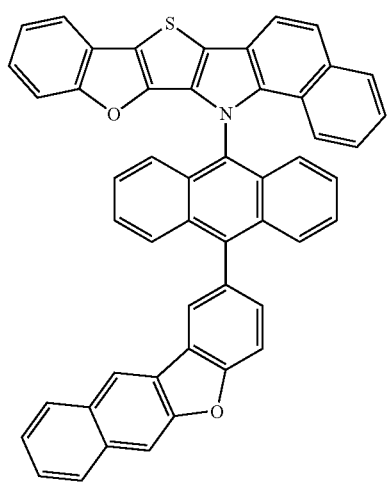
EX153
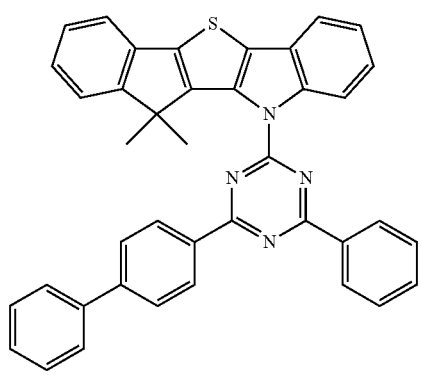
-continued
EX154
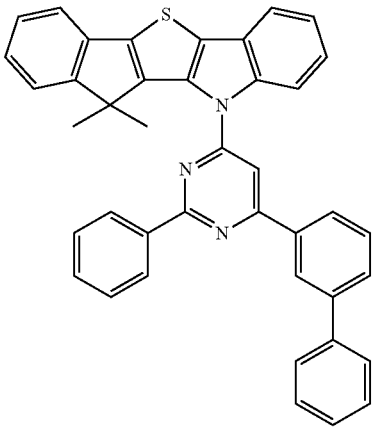
EX155
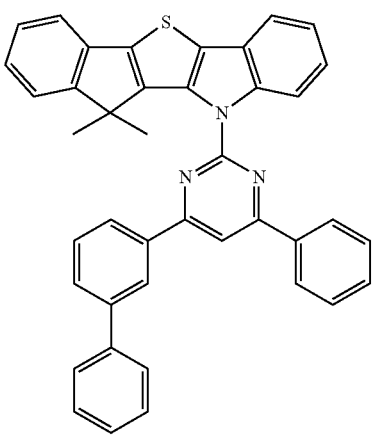
EX156
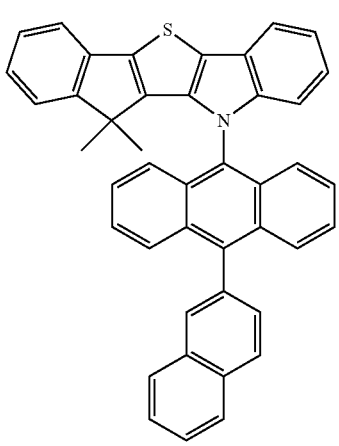
EX157
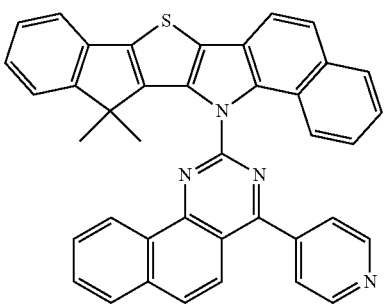

-continued
EX158
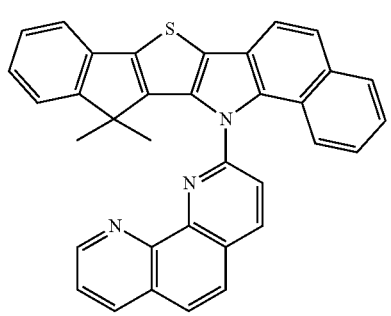
EX159
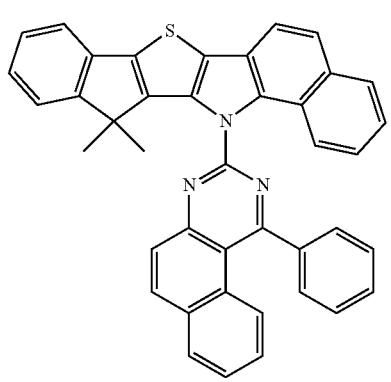
EX160
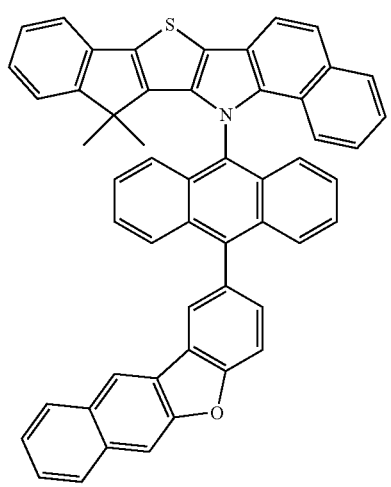
EX161
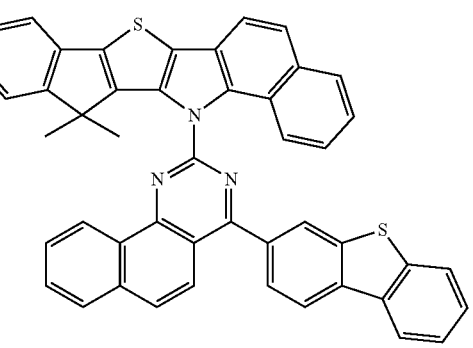
-continued
EX162
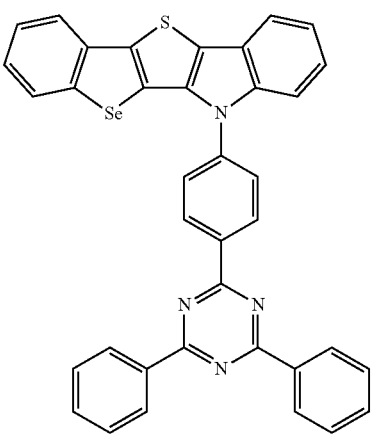
EX163
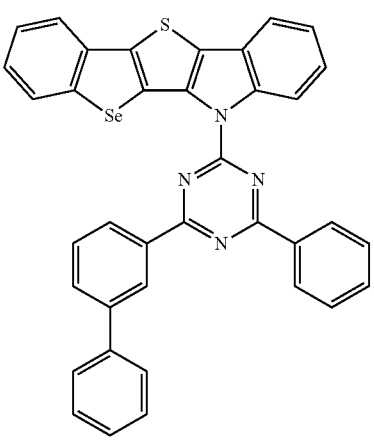
EX164
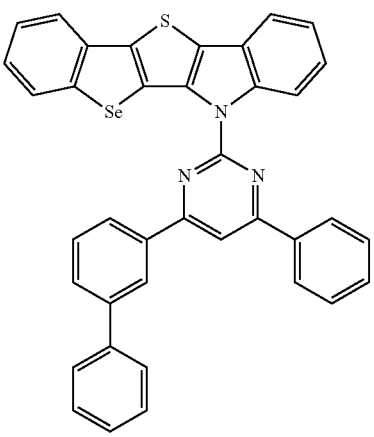

EX165
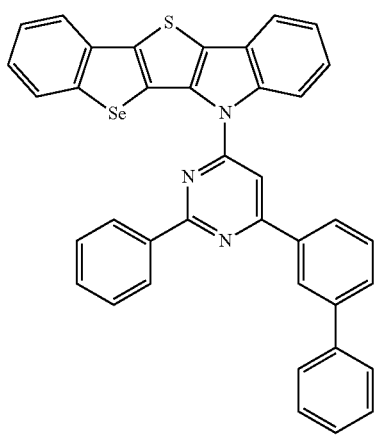

EX166
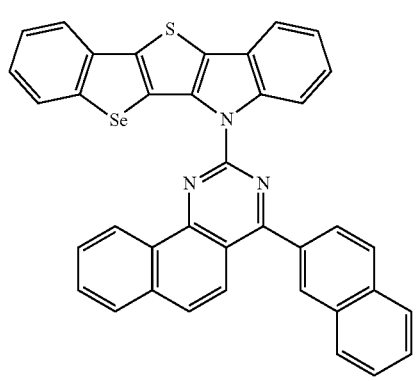

EX167
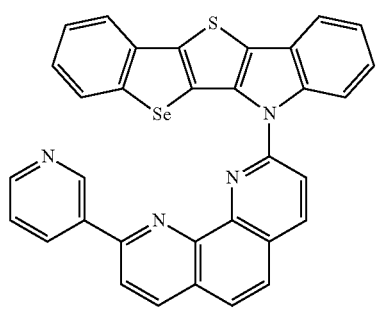

EX168
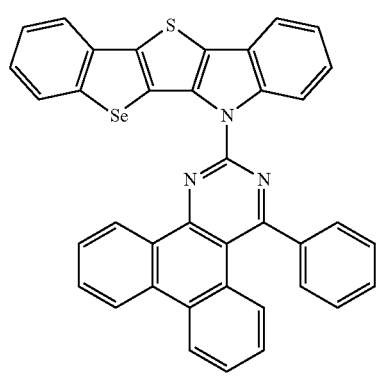

EX169
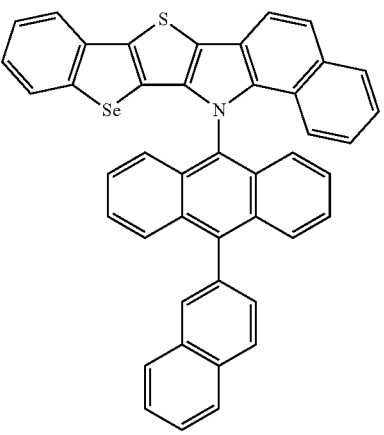

EX170
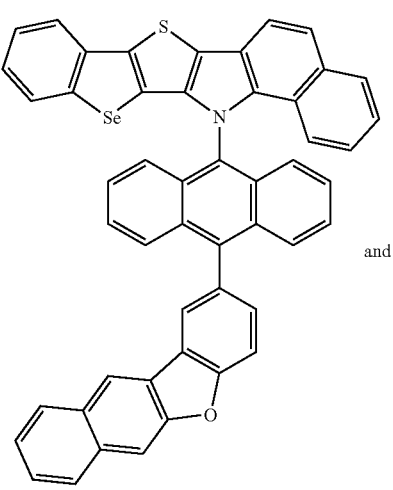

and

EX171
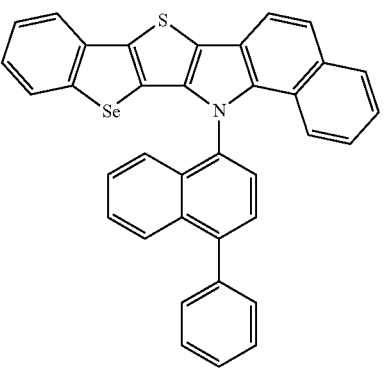

Referring to FIG. 1, the first organic EL device 610 may comprise an anode 510, a cathode 590 and one or more organic layers 520, 530, 540, 550E, 560, 570, 580 formed between the anode 510 and the cathode 589. From the bottom to the top, the one or more organic layers may comprise a hole injection layer 520, a hole transport layer 530, an electron blocking layer 540, an emissive layer 550E, a hole blocking layer 560, an electron transport layer 570 and an electron injection layer 580.

The emissive layer 550E may comprise a 15% dopant RG1 and the organic compound of formula (F) 550F doped with the dopant RG1. The dopant RG1 may be a red guest material for tuning the wavelength at which the emissive layer 550E emits light, so that the color of emitted light may be red. The organic compound of formula (F) may be a host 550F of the emissive layer 550E.

FIG. 2 is a cross-sectional view of an organic EL device without the organic compound of formula (F). Referring to FIG. 2, the organic EL device 300 may comprise an anode 510, a cathode 590 and one or more organic layers 520, 530, 540, 550, 560, 570, 580 formed between the anode 510 and the cathode 590. From the bottom to the top, the one or more organic layers may comprise a hole injection layer 320, a hole transport layer 330, an electron blocking layer 540, an emissive layer 550, a hole blocking layer 560, an electron transport layer 570 and an electron injection layer 580. The emissive layer 550 may comprise a 15% dopant RG1 and an organic compound H11 doped with the dopant RG1. The dopant RG1 may be a red guest material. The organic compound (H11 in paragraph [0002]) may be a host H11 of the emissive layer 550.

To those organic EL devices of FIG. 1 and FIG. 2, EL spectra and CIE coordination are measured by using a PR650 spectra scan spectrometer. Furthermore, the current/voltage, luminescence/voltage, and yield/voltage characteristics are taken with a Keithley 2400 programmable voltage-current source. The above-mentioned apparatuses are operated at room temperature (about 25° C.) and under atmospheric pressure.

The I-V-B (at 1000 nits) test reports of those organic EL devices of FIG. 1 and FIG. 2 may be summarized in Table 1 below. The half-life is defined as the time that the initial luminance of 1000 cd/m² has dropped to half.

TABLE 1

| Host (H11 or 550F) | Dopant | Driving Voltage (V) | Current Efficiency (cd/A) | Device Color | Half-life (hours) |
|---|---|---|---|---|---|
| H11 | RG1 | 4.3 | 17.5 | red | 800 |
| EX9 | RG1 | 4.1 | 22.7 | red | 980 |
| EX10 | RG1 | 4.0 | 23.6 | red | 1030 |
| EX18 | RG1 | 4.5 | 19.4 | red | 820 |
| EX20 | RG1 | 3.5 | 26.3 | red | 1350 |
| EX22 | RG1 | 3.6 | 25.5 | red | 1230 |
| EX27 | RG1 | 3.6 | 25.1 | red | 1190 |
| EX37 | RG1 | 3.7 | 24.7 | red | 1140 |
| EX43 | RG1 | 3.9 | 24.0 | red | 1060 |
| EX54 | RG1 | 4.3 | 21.0 | red | 870 |
| EX55 | RG1 | 4.2 | 21.7 | red | 920 |
| EX56 | RG1 | 4.7 | 17.0 | red | 700 |
| EX60 | RG1 | 3.8 | 24.4 | red | 1110 |
| EX78 | RG1 | 4.4 | 20.4 | red | 820 |
| EX85 | RG1 | 4.4 | 20.7 | red | 840 |
| EX93 | RG1 | 4.2 | 22.0 | red | 950 |
| EX94 | RG1 | 4.0 | 23.5 | red | 1020 |
| EX99 | RG1 | 4.5 | 19.5 | red | 800 |
| EX100 | RG1 | 3.5 | 25.9 | red | 1270 |
| EX130 | RG1 | 3.9 | 23.6 | red | 1040 |
| EX134 | RG1 | 4.1 | 23.1 | red | 1000 |
| EX137 | RG1 | 3.8 | 24.8 | red | 1160 |
| EX140 | RG1 | 4.2 | 21.3 | red | 900 |
| EX147 | RG1 | 4.6 | 19.0 | red | 770 |

According to Table 1, in the first organic EL device 610, the organic compound of formula (F) comprised as a host 550F of FIG. 1 exhibits performance better than a prior art organic EL material (H11).

A method of producing the first organic EL device 610 of FIG. 1 and the organic EL device 300 of FIG. 2 is described. ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water).

Before vapor deposition of the organic layers, cleaned ITO substrates may be further treated by UV and ozone. All pre-treatment processes for ITO substrate are under clean room (class 100), so that an anode 510 may be formed.

One or more organic layers 320, 330, 340 (FIG. 1), 340E (FIG. 1), 350, 360, 370 are applied onto the anode 310 in order by vapor deposition in a high-vacuum unit ($10^{-7}$ Torr), such as resistively heated quartz boats. The thickness of the respective layer and the vapor deposition rate (0.1~0.3 nm/sec) are precisely monitored or set with the aid of a quartz-crystal monitor. It is also possible, as described above, each of the organic layers may comprise more than one organic compound. For example, an emissive layer 550E or 550 may be formed of a dopant and a host doped with the dopant. An emissive layer 550E or 550 may also be formed of a co-host and a host co-deposited with the co-host. This may be successfully achieved by co-vaporization from two or more sources. Accordingly, the compounds for the organic layers of the present invention are thermally stable.

Referring to FIG. 1 and FIG. 2, onto the anode 510, Dipyrazino[2,3-f:2,3-]quinoxaline-2,3,6,7,10,11-hexacarbonitrile (HAT-CN) may be applied to form a hole injection layer 520 having a thickness of about 20 nm in the organic EL device 510 or 400. N4,N4,N4',N4'-tetra([1,1'-biphenyl]-4-yl)-[1,1'-biphenyl]-4,4'-diamine (HT1) may be applied to form a hole transport layer 530 having a thickness of about 170 nm. N-(9,9'-spirobi[fluoren]-4-yl)-N-([1,1'-biphenyl]-2-yl)-14,14-dimethyl-14H-indeno[1,2-b]triphenylen-12-amine(EB3) may be applied to form an electron blocking layer 540.

Referring to FIG. 1 and FIG. 2, in the organic EL device 610 (FIG. 1) or 300 (FIG. 2), an emissive layer 550E or 550 may be formed to have a thickness of about 30 nm.

Referring to FIG. 2, in the organic EL device 300, a compound H11 of paragraph [0002] may be applied to form a host H11 of an emissive layer 550 of FIG. 2. The emissive layer 550 may further comprise a dopant RG1 as a red guest of the emissive layer 550.

On the emissive layer 550, a compound HB3 may be used as a hole blocking material (HBM) to form a hole blocking layer 560 having a thickness of about 5 nm. 2-ethyl-1-(4-(10-(naphthalen-2-yl)anthracen-9-yl)phenyl)-1H-benzo[d]imidazole (ET2) may be applied as an electron transport material to co-deposit with 8-hydroxyquinolato-lithium (LiQ) at a ratio of about, for example, 1:1, thereby forming an electron transport layer (ETL) 570 of the organic EL device 610 or 300. The electron transport layer may have a thickness of about 25 nm.

Referring to FIG. 1 and FIG. 2, the organic EL device 610 or 300 may further comprise a low work function metal, such as Al, Mg, Ca, Li or K, as a cathode 590 by thermal evaporation. A low work function metal may help electrons injecting the electron transport layer 570 from cathode 590. The comprised metal of Al may have a thickness of about 160 nm. Between the cathode 590 and the electron transport layer 570, a thin electron injecting layer 580 of LiQ having a thickness of about 1 nm may be introduced, to reduce the electron injection barrier and to improve the performance of the organic EL device 610 or 300. The material of the electron injecting layer 580 may alternatively be metal halide or metal oxide with low work function, such as LiF, MgO, or $Li_2O$.

The organic compounds ET2, LiQ, RG1, HB3, EB3, H11, HAT-CN and HT1 for producing the organic EL device 300 or 610 in this invention may receptively have the following formulas:

ET2
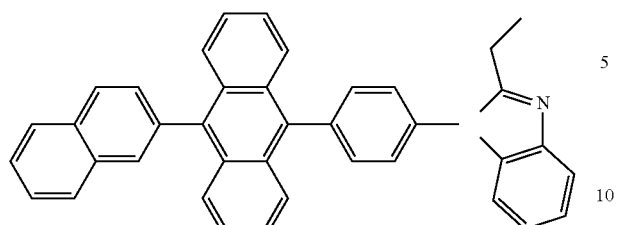

LiQ
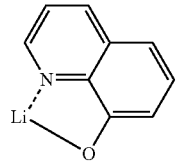

RG1
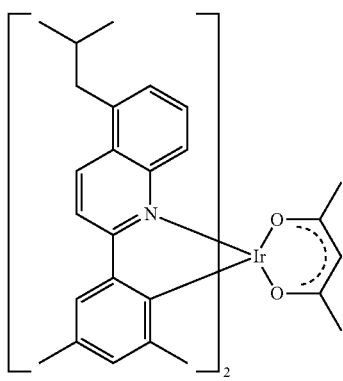

HB3
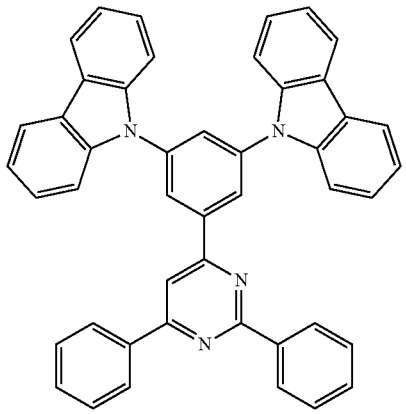

EB3
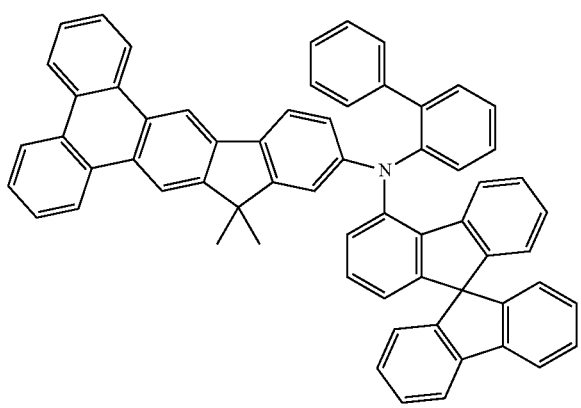

H11
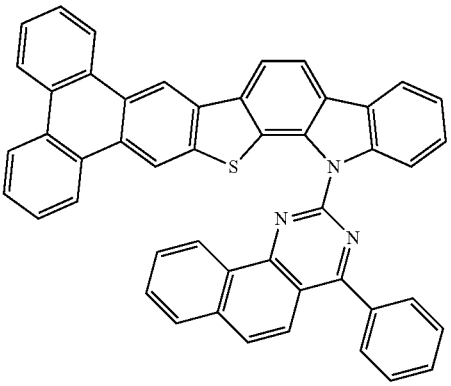

HAT-CN
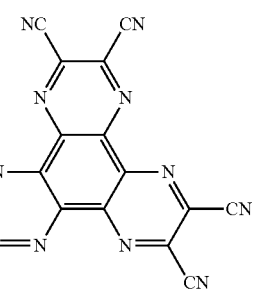

HT1
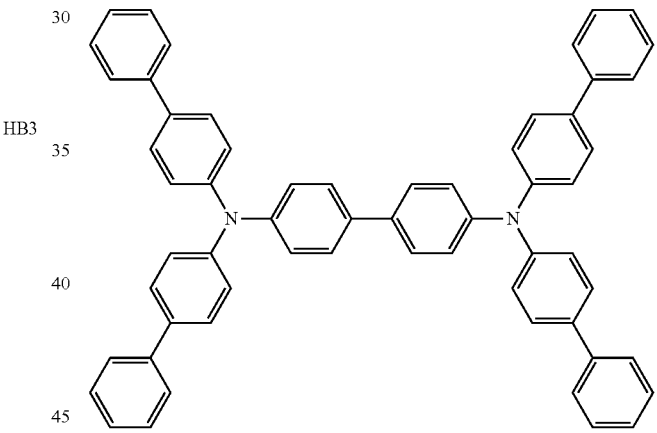

FIG. 3 is a cross-sectional view of the second organic EL device in a third embodiment of the present invention. Referring to FIG. 3, a second organic EL device 620 using the organic compound of formula (F) is disclosed. The method of producing the second organic EL device 620 of FIG. 3 is substantially the same as the method of producing the organic EL device 300 of FIG. 2. The difference is that the electron transport layer 570F of FIG. 3 is made by using the organic compound of formula (F) as an electron transport material (ETM), rather than by using ET2 as an ETM.

To those organic EL devices of FIG. 3 and FIG. 2, EL spectra and CIE coordination are measured by using a PR650 spectra scan spectrometer. Furthermore, the current/voltage, luminescence/voltage, and yield/voltage characteristics are taken with a Keithley 2400 programmable voltage-current source. The above-mentioned apparatuses are operated at room temperature (about 25° C.) and under atmospheric pressure.

The I-V-B (at 1000 nits) test reports of those organic EL devices of FIG. 3 and FIG. 2 may be summarized in Table 2 below. The half-life of the red-emitting organic EL device 620 or 300 is defined as the time that the initial luminance of 1000 cd/m² has dropped to half.

TABLE 2

| Material for ETL 570 or 570F | Driving Voltage (V) | Current Efficiency (cd/A) | Device Color | Half-life (hours) |
|---|---|---|---|---|
| ET2 | 4.3 | 17.5 | red | 800 |
| EX4 | 4.0 | 18.5 | red | 930 |
| EX18 | 3.9 | 19.0 | red | 970 |
| EX43 | 4.1 | 18.1 | red | 890 |
| EX99 | 3.9 | 18.8 | red | 950 |
| EX130 | 4.3 | 17.6 | red | 840 |
| EX147 | 4.4 | 17.3 | red | 780 |

According to Table 2, in the second organic EL device 620, the organic compound of formula (F) comprised as an electron transport layer 570F of FIG. 3 exhibits performance better than a prior art electron transport material (ET2 as an ETL 570 of FIG. 2).

FIG. 4 is a cross-sectional view of the third organic EL device in a fourth embodiment of the present invention. Referring to FIG. 4, a third organic EL device 630 using the organic compound of formula (F) is disclosed. The method of producing the second organic EL device 630 of FIG. 4 is substantially the same as the method of producing the organic EL device 300 of FIG. 2. The difference is that the hole blocking layer 560F of FIG. 3 is made by using the organic compound of formula (F) as a hole blocking material (HBM), rather than by using HB3 as a HBM.

To those organic EL devices of FIG. 4 and FIG. 2, EL spectra and CIE coordination are measured by using a PR650 spectra scan spectrometer. Furthermore, the current/voltage, luminescence/voltage, and yield/voltage characteristics are taken with a Keithley 2400 programmable voltage-current source. The above-mentioned apparatuses are operated at room temperature (about 25° C.) and under atmospheric pressure.

The I-V-B (at 1000 nits) test reports of those organic EL devices of FIG. 4 and FIG. 2 may be summarized in Table 3 below. The half-life of the red-emitting organic EL device 630 or 300 is defined as the time that the initial luminance of 1000 cd/m² has dropped to half.

TABLE 2

| Material for HBL 560 or 560F | Driving Voltage (V) | Current Efficiency (cd/A) | Device Color | Half-life (hours) |
|---|---|---|---|---|
| HB3 | 4.3 | 17.5 | red | 800 |
| EX4 | 4.3 | 17.6 | red | 820 |
| EX43 | 4.1 | 18.1 | red | 870 |
| EX130 | 4.5 | 17.0 | red | 760 |
| EX147 | 4.0 | 18.5 | red | 910 |

According to Table 3, in the third organic EL device 630, the organic compound of formula (F) comprised as a hole blocking layer 560F of FIG. 4 exhibits performance better than a prior art hole blocking material (HB3 as an HBL 560 of FIG. 2).

Referring to FIGS. 1, 3 and 4, the organic EL device 610, 620 or 630 of the present invention may alternatively be a lighting panel or a backlight panel.

Detailed preparation of the organic compounds of the present invention will be clarified by exemplary embodiments below, but the present invention is not limited thereto.

EXAMPLES 1 to 18 show the preparation of the organic compounds of the present invention.

Example 1

Synthesis of EX4
 Synthesis of Intermediate A

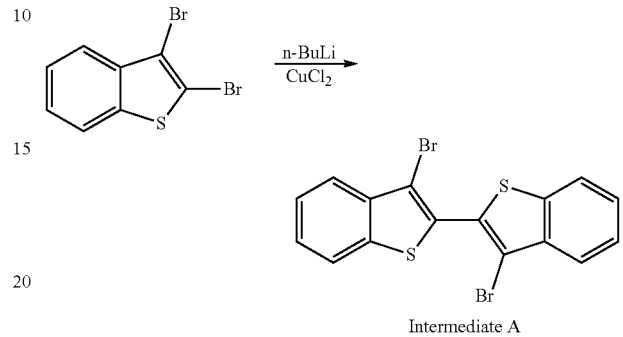

Intermediate A

The compound 2,3-dibromobenzo[b]thiophene (50.0 g, 171.1 mmole) was mixed with 1000 ml of dry THF. To the mixture, 82.0 ml of N-butyllithium (205.0 mmol) was added at −78° C. and the mixture was stirred for 1 h. After the reaction finished, 32.0 g (240.0 mmol) of Copper(II) Chloride was added and the mixture was stirred 16 h. The solution was extracted with ethyl acetate and water. The organic layer was dried with anhydrous magnesium sulfate and then the solvent was evaporated under reduced pressure. The residue was purified by column chromatography on silica to give product (32.6 g, 90%) as a purple brown solid.
 Synthesis of Intermediate B

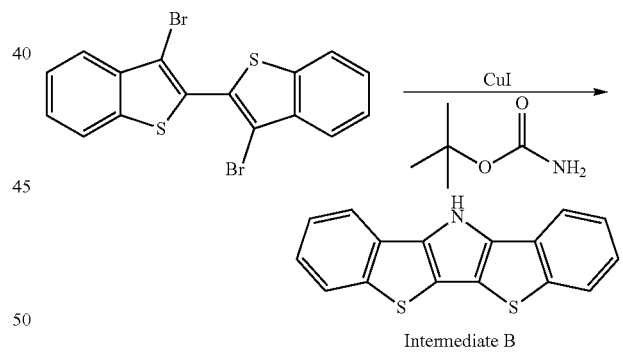

Intermediate B

A mixture of 60.0 g (142.0 mmole) of Intermediate A, 59.0 g (426.0 mmole) of Potassium carbonate, 20.0 g (170.0 mmole) of Tertiary butyl carbamate, 4.0 g (43.0 mmole) of N,N'dimethylethylenediamine, 27.0 g (142.0 mmole) of Copper iodide, and 600 ml of Toluene was placed under nitrogen, and then heated at 125° C. while stirring for 12 h. After the reaction finished, the mixture was allowed to cool to room temperature. The solution was extracted with 200 ml of Ethyl acetate (3 times) and then 300 ml of Water. The organic layer was dried with anhydrous magnesium sulfate, and then the solvent was evaporated under reduced pressure. The residue was purified by column chromatography on silica to give product (10.0 g, 25%) as a white solid. MS(m/z, EI⁺):278.3

Synthesis of EX4

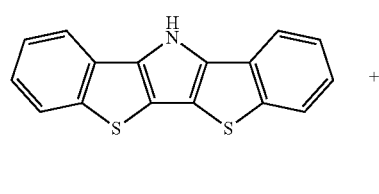
+

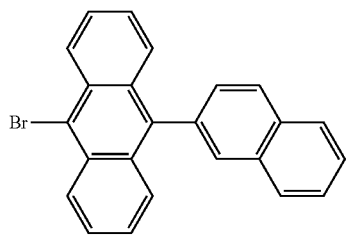

-continued

Pd$_2$(dba)$_3$/
NaO$^t$Bu
o-Xylene
→

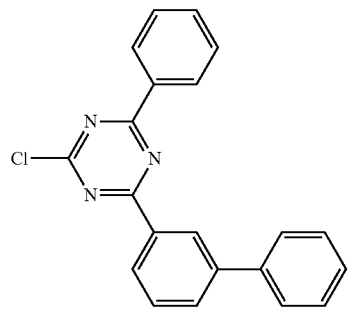

Pd$_2$(dba)$_3$/
NaO$^t$Bu
o-Xylene
→

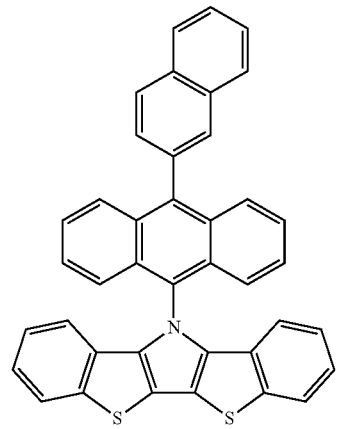

A mixture of 3 g (10.7 mmole) of Intermediate B, 4.9 g (12.8 mmol) of 9-Bromo-10-(2-naphthyl)anthracene, 0.49 g (0.54 mmol) of Pd$_2$(dba)$_3$, 2.0 g (21.4 mmol) of Sodium tert-butoxide, and 30 ml of o-Xylene was degassed and placed under nitrogen, and then heated at 150° C. for 16 h. After the reaction finished, the mixture was allowed to cool to room temperature. Then 300 ml of MeOH was added while stirring and the precipitated product was filtered off with suction to give (3.5 g, 57%) of light yellow product, which was recrystallized from EtOH. MS(m/z, EI$^+$): 580.7

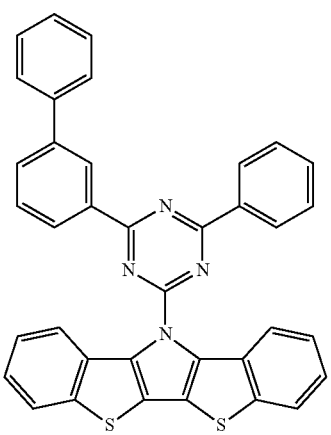

A mixture of 3 g (10.7 mmole) of Intermediate B, 4.0 g (11.8 mmol) of 2-Chloro-4-(biphenyl-3-yl)-6-phenyl-1,3,5-triazine, 0.49 g (0.54 mmol) of Pd$_2$(dba)$_3$, 2.0 g (21.4 mmol) of Sodium tert-butoxide, and 30 ml of o-Xylene was degassed and placed under nitrogen, and then heated at 150° C. for 16 h. After the reaction finished, the mixture was allowed to cool to room temperature. Then 300 ml of MeOH was added while stirring and the precipitated product was filtered off with suction to give (3.0 g, 49%) of light yellow product, which was recrystallized from EtOH. MS(m/z, EI$^+$): 585.7

Example 2

Synthesis of EX9

Synthesis of EX9

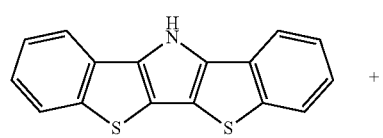
+

Example 3

Synthesis of EX18

Synthesis of EX18

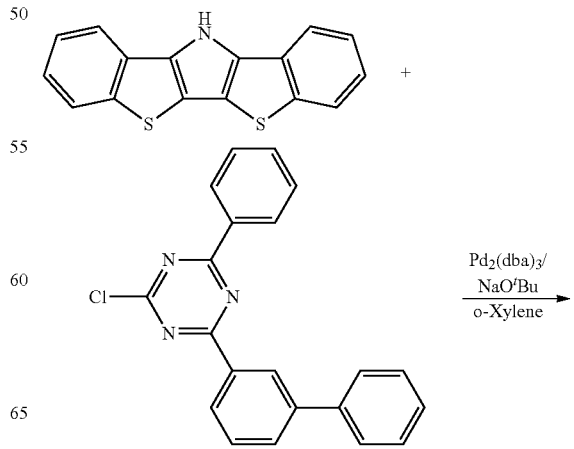

Pd$_2$(dba)$_3$/
NaO$^t$Bu
o-Xylene
→

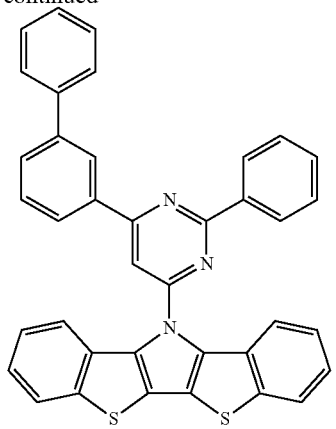

A mixture of 3 g (10.7 mmole) of Intermediate B, 4.4 g (12.8 mmol) of 4-([1,1'-Biphenyl]-3-yl)-6-chloro-2-phenylpyrimidine, 0.49 g (0.54 mmol) of Pd$_2$(dba)$_3$, 2.0 g (21.4 mmol) of Sodium tert-butoxide, and 30 ml of o-Xylene was degassed and placed under nitrogen, and then heated at 150° C. for 16 h. After the reaction finished, the mixture was allowed to cool to room temperature. Then 300 ml of MeOH was added while stirring and the precipitated product was filtered off with suction to give (2.9 g, 47%) of light yellow product, which was recrystallized from EtOH. MS(m/z, EI$^+$): 584.7

Example 4

Synthesis of EX20
Synthesis of EX20

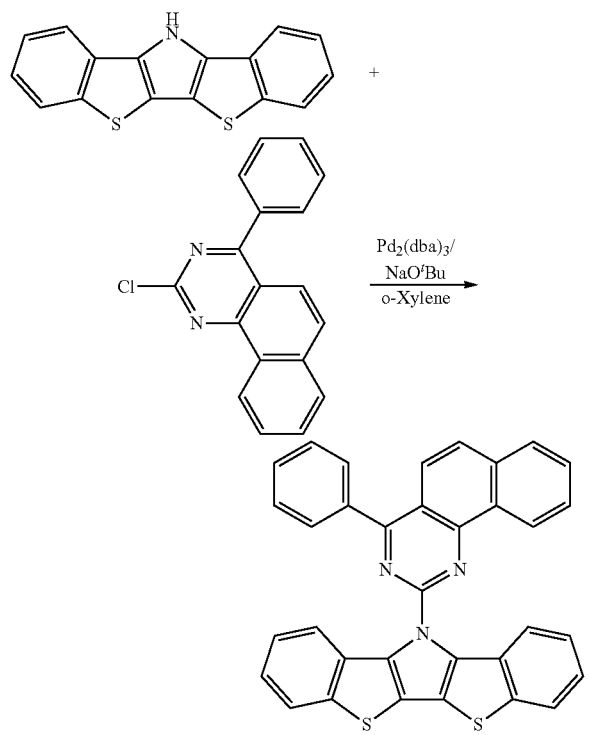

A mixture of 3 g (10.7 mmole) of Intermediate B, 3.7 g (12.8 mmol) of 2-Chloro-4-phenylbenzoquinazoline, 0.49 g (0.54 mmol) of Pd$_2$(dba)$_3$, 2.0 g (21.4 mmol) of Sodium tert-butoxide, and 30 ml of o-Xylene was degassed and placed under nitrogen, and then heated at 150° C. for 16 h. After the reaction finished, the mixture was allowed to cool to room temperature. Then 300 ml of MeOH was added while stirring and the precipitated product was filtered off with suction to give (3.2 g, 56%) of yellow product, which was recrystallized from EtOH. MS(m/z, EI$^+$): 532.6

Example 5

Synthesis of EX22
Synthesis of EX22

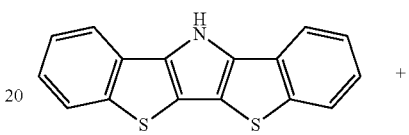

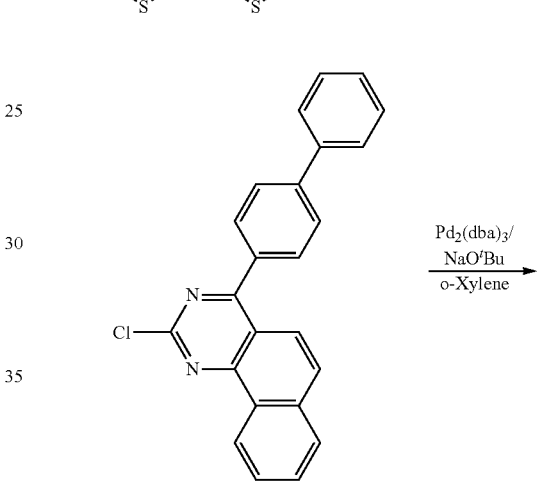

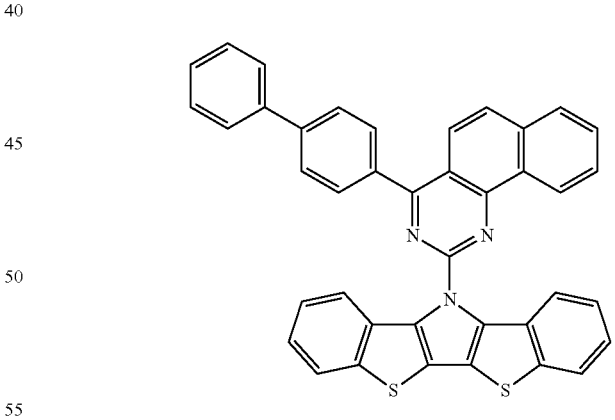

A mixture of 3 g (10.7 mmole) of Intermediate B, 5.1 g (13.9 mmol) of 4-([1,1'-Biphenyl]-4-yl)-2-chlorobenzo[h]quinazoline, 0.49 g (0.54 mmol) of Pd$_2$(dba)$_3$, 2.0 g (21.4 mmol) of Sodium tert-butoxide, and 30 ml of o-Xylene was degassed and placed under nitrogen, and then heated at 150° C. for 16 h. After the reaction finished, the mixture was allowed to cool to room temperature. Then 300 ml of MeOH was added while stirring and the precipitated product was filtered off with suction to give (2.7 g, 41%) of yellow product, which was recrystallized from EtOH. MS(m/z, EI$^+$): 608.7

Example 6

Synthesis of EX27

Synthesis of EX27

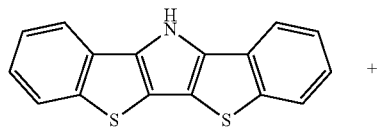

+

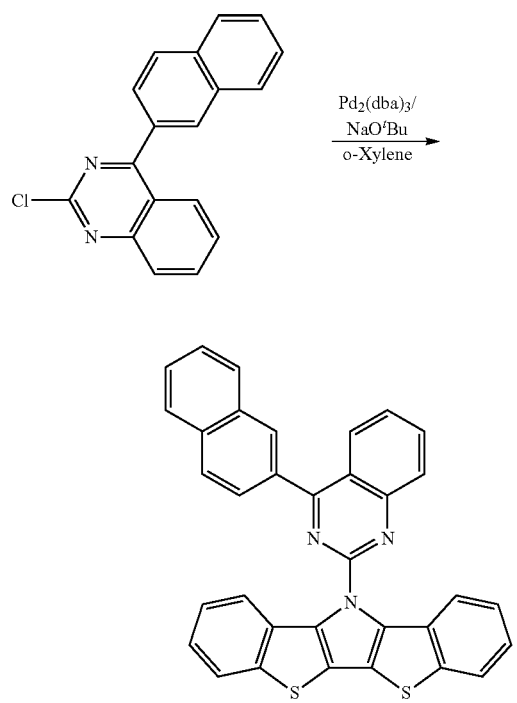

A mixture of 3 g (10.7 mmole) of Intermediate B, 3.7 g (12.8 mmol) of 2-Chloro-4-(naphthalen-2-yl)quinazoline, 0.49 g (0.54 mmol) of Pd$_2$(dba)$_3$, 2.0 g (21.4 mmol) of Sodium tert-butoxide, and 30 ml of o-Xylene was degassed and placed under nitrogen, and then heated at 150° C. for 16 h. After the reaction finished, the mixture was allowed to cool to room temperature. Then 300 ml of MeOH was added while stirring and the precipitated product was filtered off with suction to give (3.1 g, 54%) of yellow product, which was recrystallized from EtOH. MS(m/z, EI$^+$): 532.7

Example 7

Synthesis of EX37

Synthesis of EX37

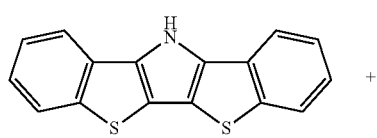

+

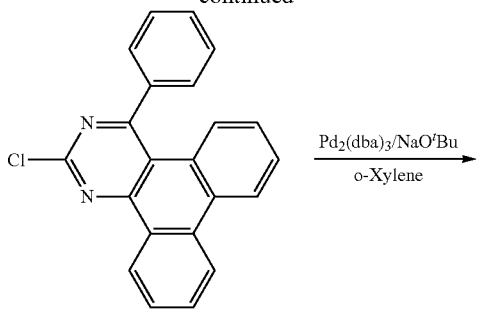

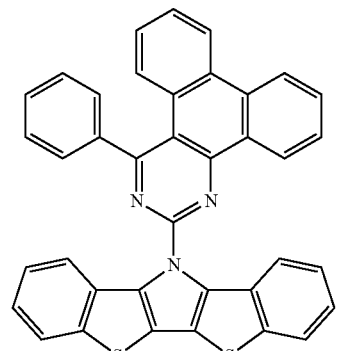

A mixture of 3 g (10.7 mmole) of Intermediate B, 4.7 g (13.9 mmol) of 2-Chloro-4-phenyldibenzo[f,h]quinazoline, 0.49 g (0.54 mmol) of Pd$_2$(dba)$_3$, 2.0 g (21.4 mmol) of Sodium tert-butoxide, and 30 ml of o-Xylene was degassed and placed under nitrogen, and then heated at 150° C. for 16 h. After the reaction finished, the mixture was allowed to cool to room temperature. Then 300 ml of MeOH was added while stirring and the precipitated product was filtered off with suction to give (2.7 g, 44%) of yellow product, which was recrystallized from EtOH. MS(m/z, EI$^+$): 582.7

Example 8

Synthesis of EX43

Synthesis of EX43

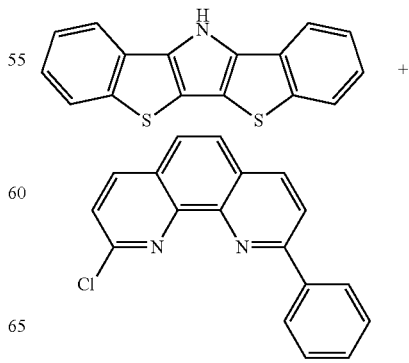

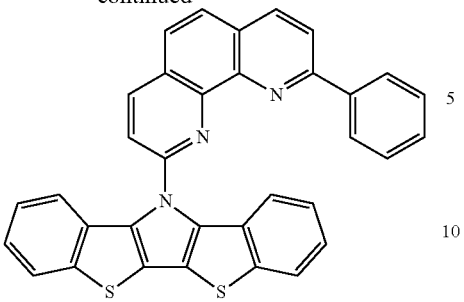

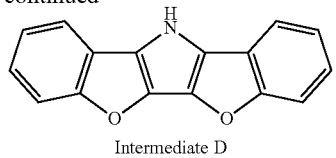

Intermediate D

A mixture of 50.0 g (127.5 mmole) of Intermediate C, 52.9 g (382.5 mmole) of Potassium carbonate, 17.9 g (153 mmole) of Tertiary butyl carbamate, 3.6 g (38.2 mmole) of N,N'dimethylethylenediamine, 24.3 g (127.5 mmole) of Copper iodide, and 500 ml of Toluene was placed under nitrogen, and then heated at 125° C. while stirring for 12 h. After the reaction finished, the mixture was allowed to cool to room temperature. The solution was extracted with 200 ml of Ethyl acetate (3 times) and then 300 ml of Water. The organic layer was dried with anhydrous magnesium sulfate, and then the solvent was evaporated under reduced pressure. The residue was purified by column chromatography on silica to give product (9.8 g, 31%) as a white solid. MS(m/z, EI$^+$): 246.2

Synthesis of EX55

A mixture of 3 g (10.7 mmole) of Intermediate B, 3.7 g (12.8 mmol) of 2-Chloro-9-phenyl-1,10-phenanthroline, 0.49 g (0.54 mmol) of Pd$_2$(dba)$_3$, 2.0 g (21.4 mmol) of Sodium tert-butoxide, and 30 ml of o-Xylene was degassed and placed under nitrogen, and then heated at 150° C. for 16 h. After the reaction finished, the mixture was allowed to cool to room temperature. Then 300 ml of MeOH was added while stirring and the precipitated product was filtered off with suction to give (3.5 g, 61%) of yellow product, which was recrystallized from EtOH. MS(m/z, EI$^+$): 532.6

Example 9

Synthesis of EX55

Synthesis of Intermediate C

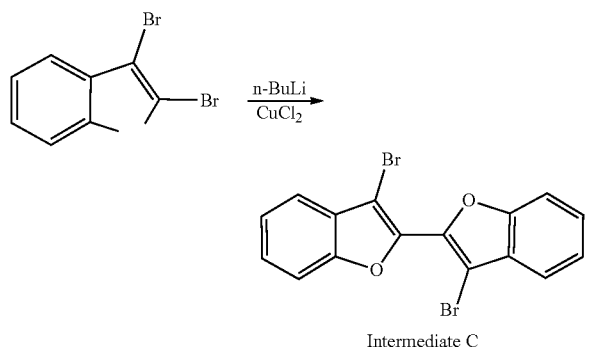

Intermediate C

The compound 2,3-Dibromobenzofuran (50.0 g, 181.2 mmole) was mixed with 1000 ml of dry THF. To the mixture, 87.0 ml of N-butyllithium (217.4 mmol) was added at −78° C. and the mixture was stirred for 1 h. After the reaction finished, 34.1 g (253.7 mmol) of Copper(II) Chloride was added and the mixture was stirred 16 h. The solution was extracted with ethyl acetate and water. The organic layer was dried with anhydrous magnesium sulfate and then the solvent was evaporated under reduced pressure. The residue was purified by column chromatography on silica to give product (61.8 g, 87%) as a brown solid.

Synthesis of Intermediate D

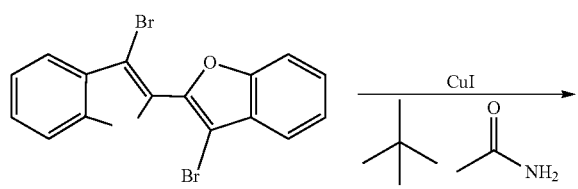

A mixture of 3 g (12.1 mmole) of Intermediate D, 6.9 g (14.5 mmol) of 2-(10-Bromoanthracen-9-yl)naphtho[2,3-b]benzofuran, 0.55 g (0.60 mmol) of Pd$_2$(dba)$_3$, 2.3 g (24.2 mmol) of Sodium tert-butoxide, and 30 ml of o-Xylene was degassed and placed under nitrogen, and then heated at 150° C. for 16 h. After the reaction finished, the mixture was allowed to cool to room temperature. Then 300 ml of MeOH was added while stirring and the precipitated product was filtered off with suction to give (3.7 g, 48%) of light yellow product, which was recrystallized from EtOH. MS(m/z, EI⁺): 638.7

Example 9

Synthesis of EX60

Synthesis of EX60

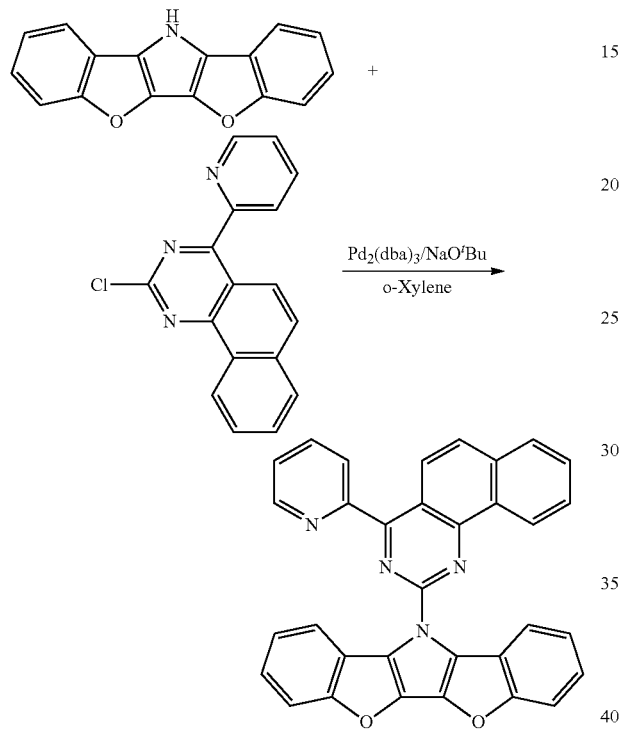

A mixture of 3 g (12.1 mmole) of Intermediate D, 4.2 g (14.5 mmol) of 2-Chloro-4-pyridinylbenzo[h]quinazoline, 0.55 g (0.60 mmol) of Pd₂(dba)₃, 2.3 g (24.2 mmol) of Sodium tert-butoxide, and 30 ml of o-Xylene was degassed and placed under nitrogen, and then heated at 150° C. for 16 h. After the reaction finished, the mixture was allowed to cool to room temperature. Then 300 ml of MeOH was added while stirring and the precipitated product was filtered off with suction to give (3.5 g, 57%) of light yellow product, which was recrystallized from EtOH. MS(m/z, EI⁺): 501.5

Example 10

Synthesis of EX78

Synthesis of Intermediate E

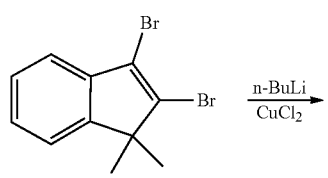

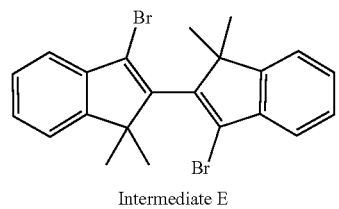

The compound 2,3-Dibromo-1,1-dimethylindene (50.0 g, 165.6 mmole) was mixed with 1000 ml of dry THF. To the mixture, 79.5 ml of N-butyllithium (198.7 mmol) was added at −78° C. and the mixture was stirred for 1 h. After the reaction finished, 31.2 g (231.8 mmol) of Copper(II) Chloride was added and the mixture was stirred 16 h. The solution was extracted with ethyl acetate and water. The organic layer was dried with anhydrous magnesium sulfate and then the solvent was evaporated under reduced pressure. The residue was purified by column chromatography on silica to give product (68.4 g, 93%) as a brown solid.

Synthesis of Intermediate F

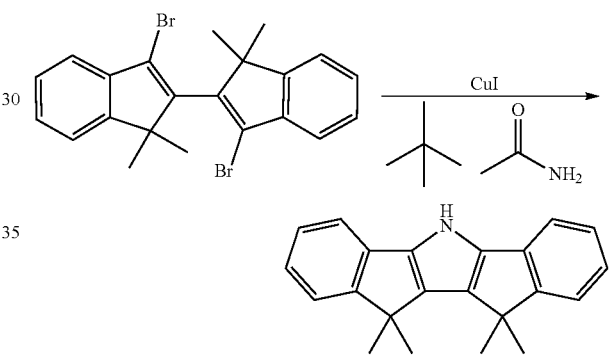

A mixture of 60.0 g (135.0 mmole) of Intermediate E, 56.0 g (405.0 mmole) of Potassium carbonate, 19.0 g (162.0 mmole) of Tertiary butyl carbamate, 3.8 g (40.5 mmole) of N,N'dimethylethylenediamine, 25.7 g (135.0 mmole) of Copper iodide, and 600 ml of Toluene was placed under nitrogen, and then heated at 125° C. while stirring for 12 h. After the reaction finished, the mixture was allowed to cool to room temperature. The solution was extracted with 200 ml of Ethyl acetate (3 times) and then 300 ml of Water. The organic layer was dried with anhydrous magnesium sulfate, and then the solvent was evaporated under reduced pressure. The residue was purified by column chromatography on silica to give product (13.7 g, 34%) as a white solid. MS(m/z, EI⁺): 298.4

Synthesis of EX78

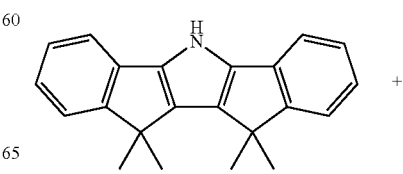

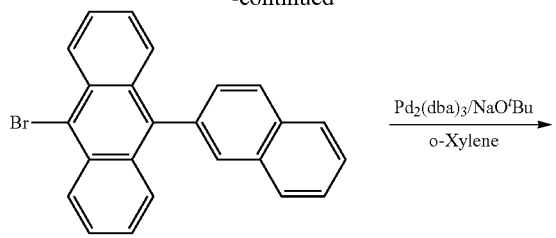

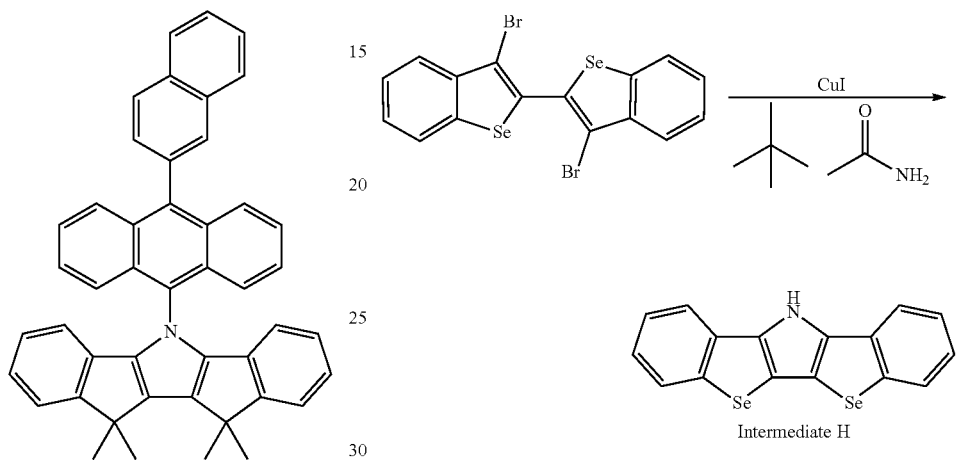

Intermediate H

A mixture of 3.0 g (10.0 mmole) of Intermediate F, 4.6 g (12.0 mmol) of 9-Bromo-10-(2-naphthyl)anthracene, 0.46 g (0.5 mmol) of Pd$_2$(dba)$_3$, 2.8 g (20.0 mmol) of Sodium tert-butoxide, and 30 ml of o-Xylene was degassed and placed under nitrogen, and then heated at 150° C. for 16 h. After the reaction finished, the mixture was allowed to cool to room temperature. Then 300 ml of MeOH was added while stirring and the precipitated product was filtered off with suction to give (3.0 g, 50%) of light yellow product, which was recrystallized from EtOH. MS(m/z, EI$^+$): 600.8

Example 11

Synthesis of EX85
Synthesis of Intermediate G

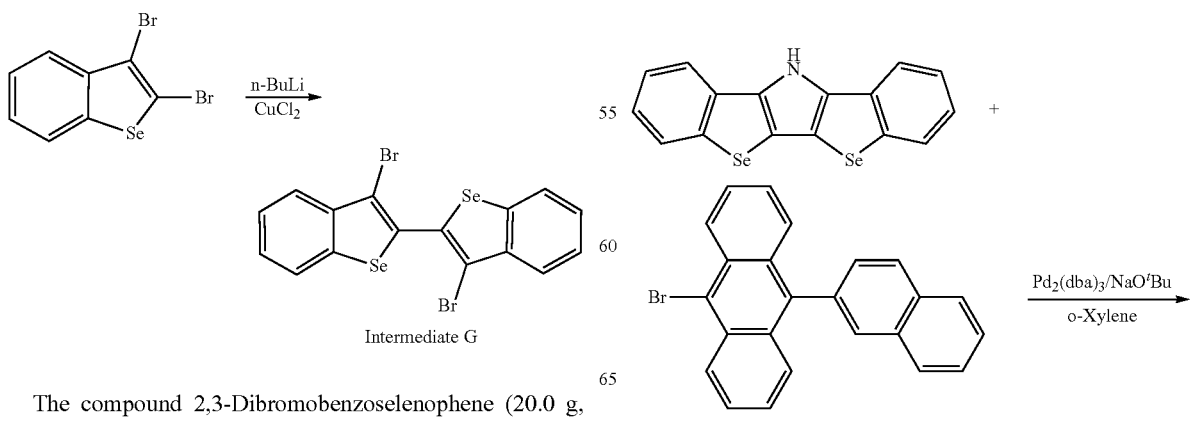

Intermediate G

The compound 2,3-Dibromobenzoselenophene (20.0 g, 59.0 mmole) was mixed with 400 ml of dry THF. To the mixture, 28.3 ml of N-butyllithium (70.8 mmol) was added at −78° C. and the mixture was stirred for 1 h. After the reaction finished, 11.1 g (82.6 mmol) of Copper(II) Chloride was added and the mixture was stirred 16 h. The solution was extracted with ethyl acetate and water. The organic layer was dried with anhydrous magnesium sulfate and then the solvent was evaporated under reduced pressure. The residue was purified by column chromatography on silica to give product (27.8 g, 91%) as a brown solid.

Synthesis of Intermediate H

A mixture of 27.0 g (52.1 mmole) of Intermediate G, 21.6 g (156.3 mmole) of Potassium carbonate, 7.3 g (62.5 mmole) of Tertiary butyl carbamate, 1.5 g (15.6 mmol) of N,N'dimethylethylenediamine, 9.9 g (52.1 mmole) of Copper iodide, and 270 ml of Toluene was placed under nitrogen, and then heated at 125° C. while stirring for 12 h. After the reaction finished, the mixture was allowed to cool to room temperature. The solution was extracted with 100 ml of Ethyl acetate (3 times) and then 150 ml of Water. The organic layer was dried with anhydrous magnesium sulfate, and then the solvent was evaporated under reduced pressure. The residue was purified by column chromatography on silica to give product (6.2 g, 32%) as a white solid. MS(m/z, EI$^+$): 372.2

Synthesis of EX85

-continued

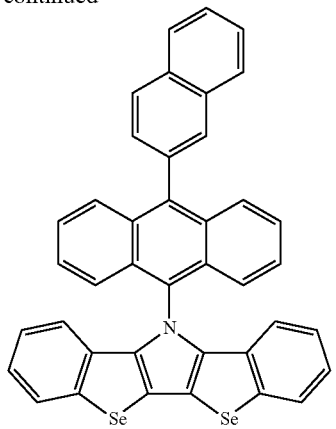

A mixture of 3.0 g (8.0 mmole) of Intermediate H, 3.7 g (9.6 mmol) of 9-Bromo-10-(2-naphthyl)anthracene, 0.37 g (0.4 mmol) of Pd$_2$(dba)$_3$, 1.5 g (16.0 mmol) of Sodium tert-butoxide, and 30 ml of o-Xylene was degassed and placed under nitrogen, and then heated at 150° C. for 16 h. After the reaction finished, the mixture was allowed to cool to room temperature. Then 300 ml of MeOH was added while stirring and the precipitated product was filtered off with suction to give (2.6 g, 48%) of light yellow product, which was recrystallized from EtOH. MS(m/z, EI$^+$): 674.5

Example 12

Synthesis of EX93

Synthesis of Intermediate I

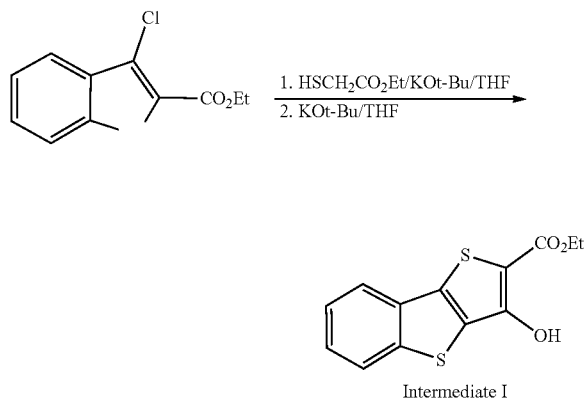

A mixture of 12.0 g (50.0 mmole) of Ethyl 3-chlorobenzo[b]thiophene-2-carboxylate, 11.2 g (100.0 mmole) of potassium tert-butoxide, 12.2 g (100.0 mmole) of Ethyl mercaptoacetate, and 300 ml of Dry THF was placed under nitrogen, and then at room temperature while stirring for 1 h. Then 11.2 g (100.0 mmole) of potassium tert-butoxide was added and heated at 80° C. while stirring for 3 h. After the reaction finished, the mixture was allowed to cool to room temperature. Then 300 ml of H$_2$O and 50 ml concentrated HCl was added while stirring and the precipitated product was filtered off with suction to give (11.2 g, 80%) of white product, which was recrystallized from EtOH.

Synthesis of Intermediate J

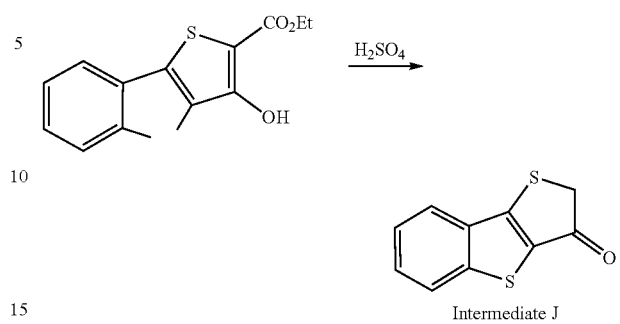

Intermediate J

A mixture of 11.2 g (40.0 mmole) of Intermediate I, and 200 ml of 90% sulfuric acid was placed under nitrogen, and then heated at 80° C. while stirring for 2 h. After the reaction finished, the mixture was allowed to cool to room temperature. The solution was extracted with 150 ml of Dichloromethane (3 times) and then 300 ml of water. The organic layer was dried with anhydrous magnesium sulfate, and then the solvent was evaporated under reduced pressure. The residue was purified by column chromatography on silica to give product (5.8 g, 70%) as a light yellow solid.

Synthesis of Intermediate K

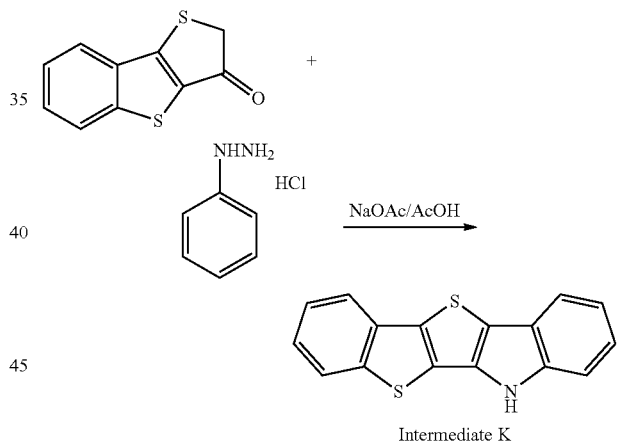

Intermediate K

A mixture of 5.8 g (28.1 mmole) of Intermediate J, 4.9 g (33.7 mmole) of Phenylhydrazine hydrochloride, 4.6 g (56.2 mmole) of Sodium acetate, and 140 ml of Acetic acid was placed under nitrogen, and then heated at 120° C. for 1 h. After the reaction finished, the mixture was allowed to cool to room temperature. The precipitated product was filtered off with suction to give (6.3 g, 80%) of white product, which was washed from Toluene and EtOH. MS(m/z, EI$^+$): 278.4

Synthesis of EX93

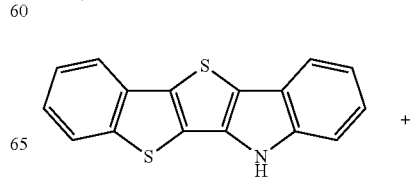 +

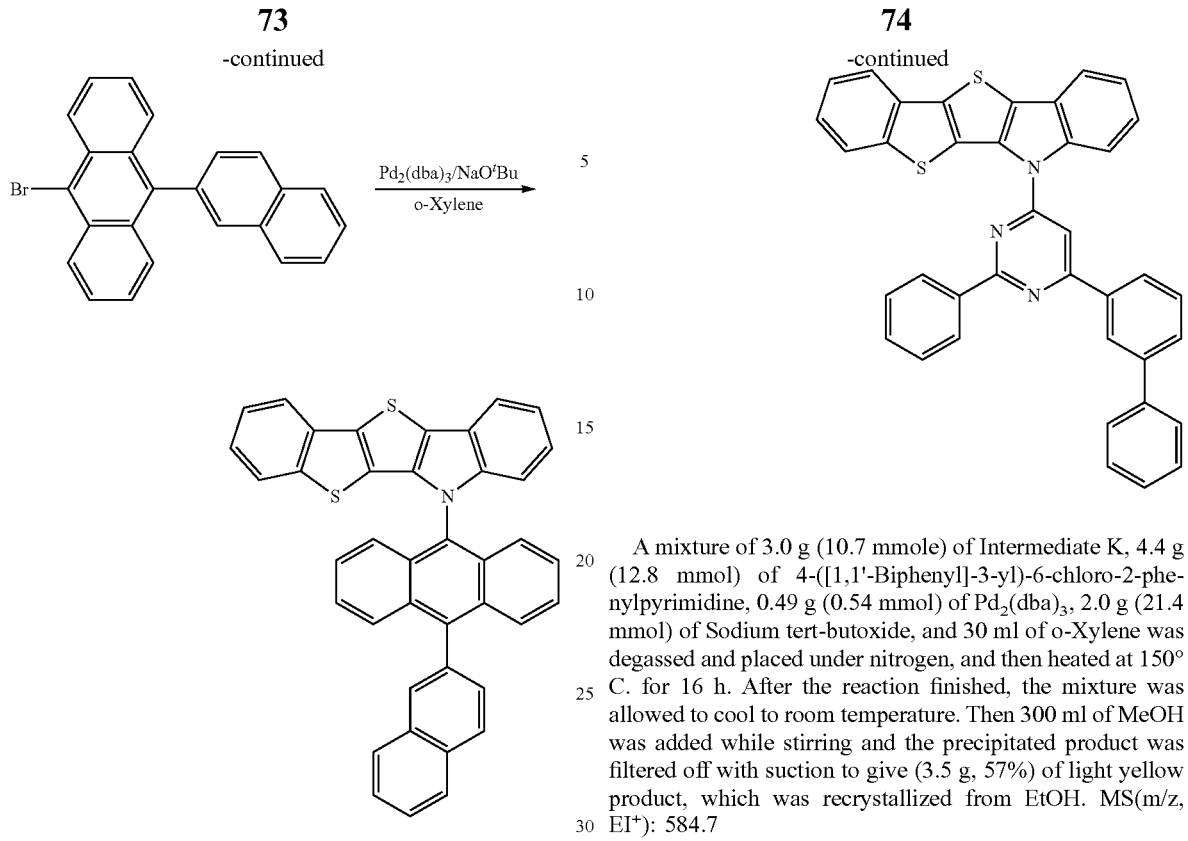

A mixture of 3.0 g (10.7 mmole) of Intermediate K, 4.9 g (12.8 mmol) of 9-Bromo-10-(2-naphthyl)anthracene, 0.49 g (0.54 mmol) of Pd$_2$(dba)$_3$, 2.0 g (21.4 mmol) of Sodium tert-butoxide, and 30 ml of o-Xylene was degassed and placed under nitrogen, and then heated at 150° C. for 16 h. After the reaction finished, the mixture was allowed to cool to room temperature. Then 300 ml of MeOH was added while stirring and the precipitated product was filtered off with suction to give (2.4 g, 39%) of light yellow product, which was recrystallized from EtOH. MS(m/z, EI$^+$): 580.7

Example 13

Synthesis of EX99
Synthesis of EX99

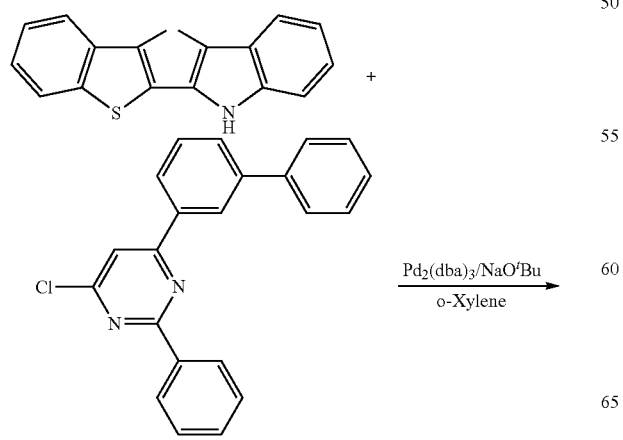

A mixture of 3.0 g (10.7 mmole) of Intermediate K, 4.4 g (12.8 mmol) of 4-([1,1'-Biphenyl]-3-yl)-6-chloro-2-phenylpyrimidine, 0.49 g (0.54 mmol) of Pd$_2$(dba)$_3$, 2.0 g (21.4 mmol) of Sodium tert-butoxide, and 30 ml of o-Xylene was degassed and placed under nitrogen, and then heated at 150° C. for 16 h. After the reaction finished, the mixture was allowed to cool to room temperature. Then 300 ml of MeOH was added while stirring and the precipitated product was filtered off with suction to give (3.5 g, 57%) of light yellow product, which was recrystallized from EtOH. MS(m/z, EI$^+$): 584.7

Example 14

Synthesis of EX100
Synthesis of EX100

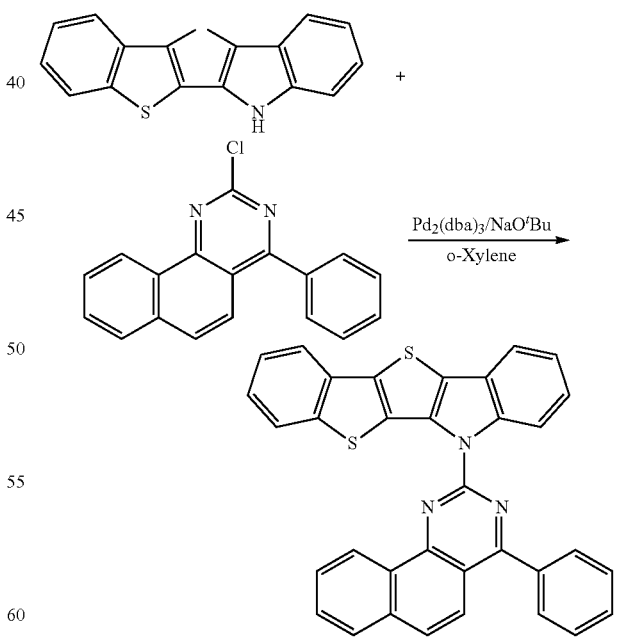

A mixture of 3.0 g (10.7 mmole) of Intermediate K, 3.7 g (12.8 mmol) of 2-Chloro-4-phenylbenzoquinazoline, 0.49 g (0.54 mmol) of Pd$_2$(dba)$_3$, 2.0 g (21.4 mmol) of Sodium tert-butoxide, and 30 ml of o-Xylene was degassed and placed under nitrogen, and then heated at 150° C. for 16 h.

After the reaction finished, the mixture was allowed to cool to room temperature. Then 300 ml of MeOH was added while stirring and the precipitated product was filtered off with suction to give (3.0 g, 54%) of yellow product, which was recrystallized from EtOH. MS(m/z, EI⁺): 532.6

Example 15

Synthesis of EX130
Synthesis of Intermediate L

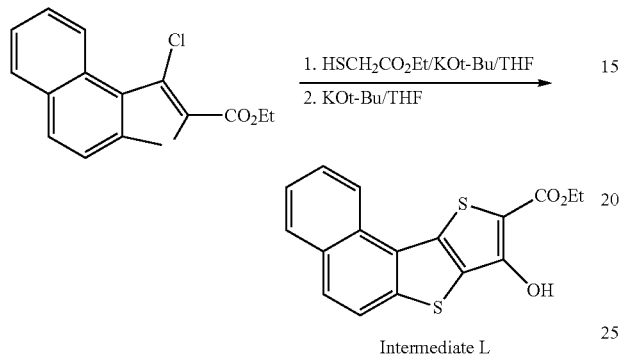

Intermediate L

A mixture of 14.5 g (50.0 mmole) of Ethyl 1-chloronaphtho[2,1-b]thiophene-2-carboxylate, 11.2 g (100.0 mmole) of potassium tert-butoxide, 12.2 g (100.0 mmole) of Ethyl mercaptoacetate, and 300 ml of Dry THF was placed under nitrogen, and then at room temperature while stirring for 1 h. Then 11.2 g (100.0 mmole) of potassium tert-butoxide was added and heated at 80° C. while stirring for 3 h. After the reaction finished, the mixture was allowed to cool to room temperature. Then 300 ml of H₂O and 50 ml concentrated HCl was added while stirring and the precipitated product was filtered off with suction to give (11.5 g, 70%) of pale yellow product, which was recrystallized from EtOH.

Synthesis of Intermediate M

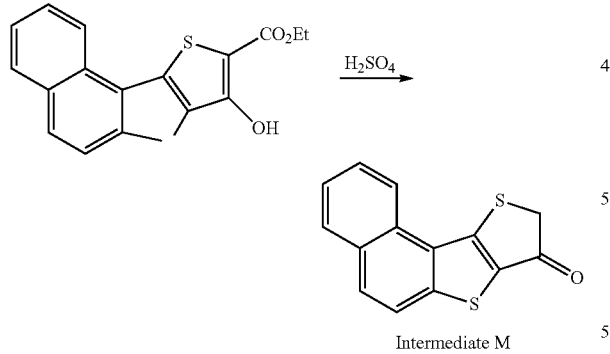

Intermediate M

A mixture of 11.5 g (35.0 mmole) of Intermediate L, and 175 ml of 90% sulfuric acid was placed under nitrogen, and then heated at 80° C. while stirring for 2 h. After the reaction finished, the mixture was allowed to cool to room temperature. The solution was extracted with 150 ml of Dichloromethane (3 times) and then 300 ml of water. The organic layer was dried with anhydrous magnesium sulfate, and then the solvent was evaporated under reduced pressure. The residue was purified by column chromatography on silica to give product (7.7 g, 86%) as a light yellow solid.

Synthesis of Intermediate N

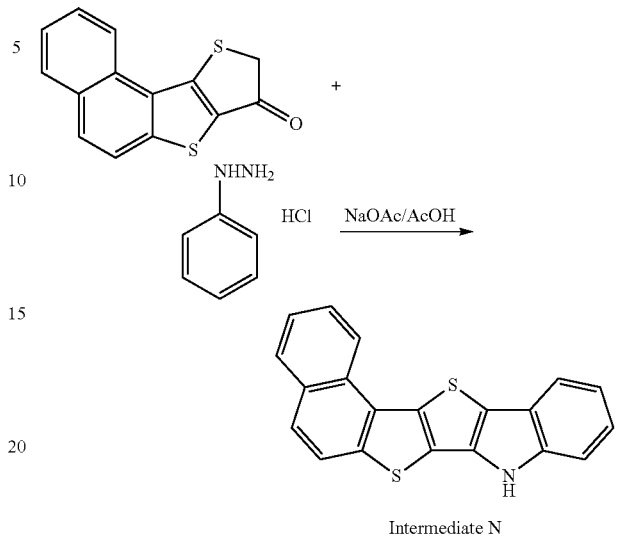

Intermediate N

A mixture of 7.7 g (30.1 mmole) of Intermediate M, 5.2 g (36.1 mmole) of Phenylhydrazine hydrochloride, 4.9 g (60.2 mmole) of Sodium acetate, and 150 ml of Acetic acid was placed under nitrogen, and then heated at 120° C. for 1 h. After the reaction finished, the mixture was allowed to cool to room temperature. The precipitated product was filtered off with suction to give (5.4 g, 55%) of light yellow product, which was washed from Toluene and EtOH. MS(m/z, EI⁺): 328.4

Synthesis of EX130

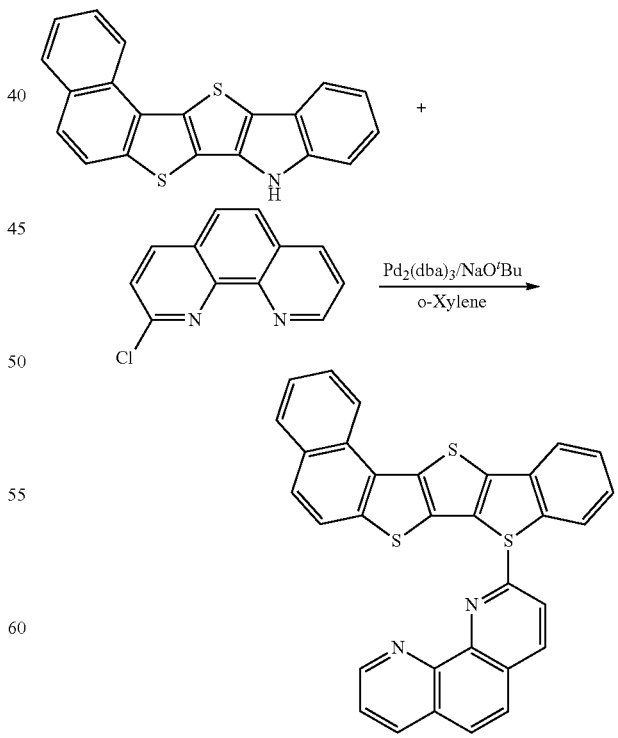

A mixture of 3.0 g (9.1 mmole) of Intermediate K, 2.3 g (10.9 mmol) of 2-Chloro-1,10-phenanthroline, 0.42 g (0.45 mmol) of Pd₂(dba)₃, 1.7 g (18.2 mmol) of Sodium tert-butoxide, and 30 ml of o-Xylene was degassed and placed under nitrogen, and then heated at 150° C. for 16 h. After the reaction finished, the mixture was allowed to cool to room temperature. Then 300 ml of MeOH was added while stirring and the precipitated product was filtered off with suction to give (2.0 g, 43%) of yellow product, which was recrystallized from EtOH. MS(m/z, EI⁺): 506.6

Example 16

Synthesis of EX137
Synthesis of Intermediate O

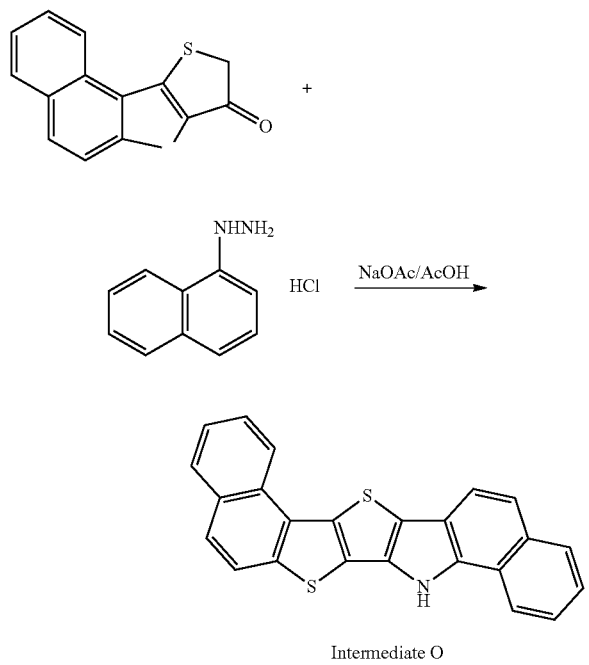

Intermediate O

A mixture of 10.0 g (39.0 mmole) of Intermediate M, 9.1 g (46.8 mmole) of 1-Naphthalenylhydrazine hydrochloride, 6.4 g (78.0 mmole) of Sodium acetate, and 195 ml of Acetic acid was placed under nitrogen, and then heated at 120° C. for 1 h. After the reaction finished, the mixture was allowed to cool to room temperature. The precipitated product was filtered off with suction to give (11.1 g, 75%) of light yellow product, which was washed from Toluene and EtOH. MS(m/z, EI⁺): 378.5

Synthesis of EX137

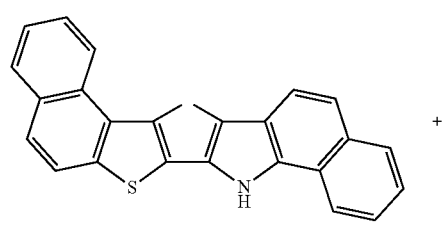

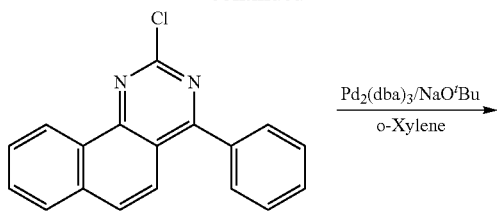

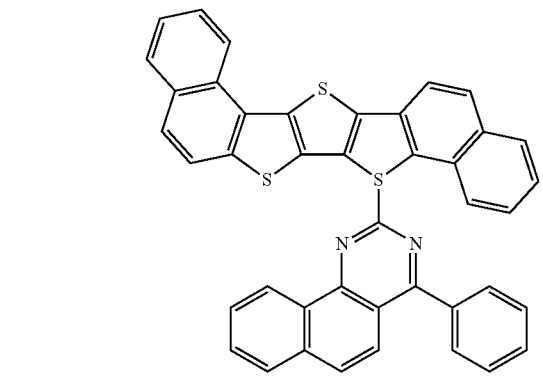

A mixture of 3.0 g (7.9 mmole) of Intermediate O, 2.7 g (9.5 mmol) of 2-Chloro-4-phenylbenzoquinazoline, 0.36 g (0.40 mmol) of Pd₂(dba)₃, 1.5 g (15.8 mmol) of Sodium tert-butoxide, and 30 ml of o-Xylene was degassed and placed under nitrogen, and then heated at 150° C. for 16 h. After the reaction finished, the mixture was allowed to cool to room temperature. Then 300 ml of MeOH was added while stirring and the precipitated product was filtered off with suction to give (1.6 g, 31%) of yellow product, which was recrystallized from EtOH. MS(m/z, EI⁺): 632.8

Example 17

Synthesis of EX140
Synthesis of EX140

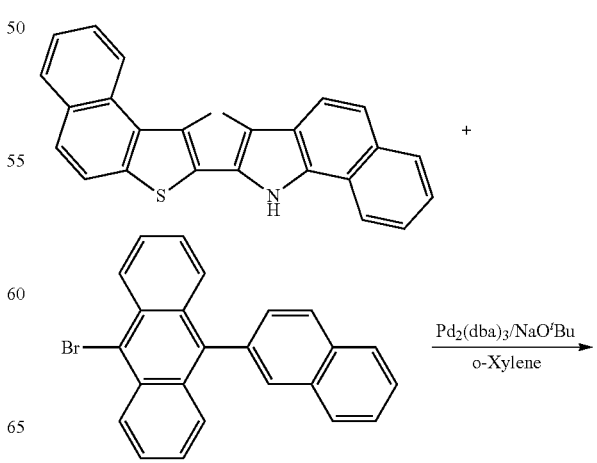

-continued

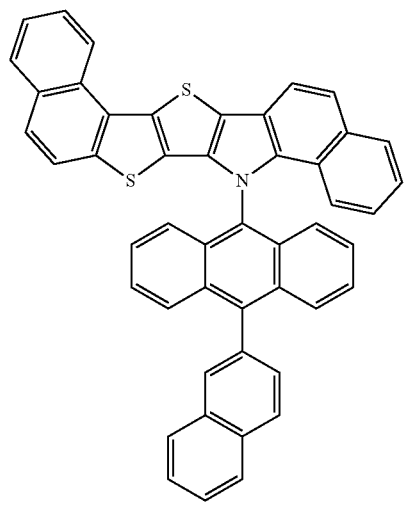

A mixture of 3.0 g (7.9 mmole) of Intermediate O, 3.6 g (9.5 mmol) of 9-Bromo-10-(2-naphthyl)anthracene, 0.36 g (0.40 mmol) of $Pd_2(dba)_3$, 1.5 g (15.8 mmol) of Sodium tert-butoxide, and 30 ml of o-Xylene was degassed and placed under nitrogen, and then heated at 150° C. for 16 h. After the reaction finished, the mixture was allowed to cool to room temperature. Then 300 ml of MeOH was added while stirring and the precipitated product was filtered off with suction to give (2.4 g, 44%) of light yellow product, which was recrystallized from EtOH. MS(m/z, EI$^+$): 680.9

Example 18

Synthesis of EX147

Synthesis of Intermediate P

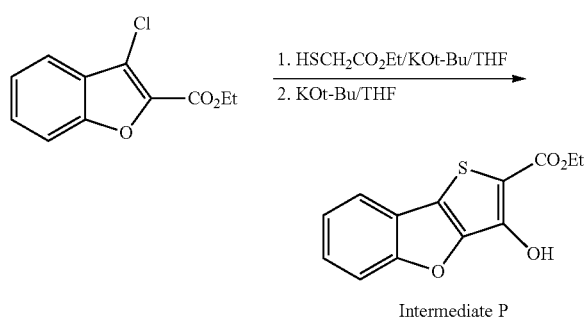

Intermediate P

A mixture of 11.2 g (50.0 mmole) of Ethyl 3-chlorobenzofuran-2-carboxylate, 11.2 g (100.0 mmole) of potassium tert-butoxide, 12.2 g (100.0 mmole) of Ethyl mercaptoacetate, and 300 ml of Dry THF was placed under nitrogen, and then at room temperature while stirring for 1 h. Then 11.2 g (100.0 mmole) of potassium tert-butoxide was added and heated at 80° C. while stirring for 3 h. After the reaction finished, the mixture was allowed to cool to room temperature. Then 300 ml of $H_2O$ and 50 ml concentrated HCl was added while stirring and the precipitated product was filtered off with suction to give (9.6 g, 73%) of white product, which was recrystallized from EtOH.

Synthesis of Intermediate Q

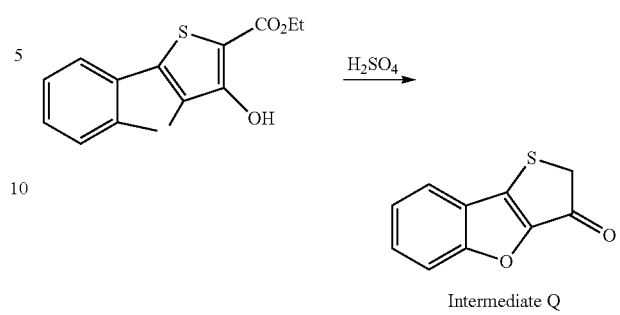

Intermediate Q

A mixture of 9.6 g (36.5 mmole) of Intermediate P, and 190 ml of 90% sulfuric acid was placed under nitrogen, and then heated at 80° C. while stirring for 2 h. After the reaction finished, the mixture was allowed to cool to room temperature. The solution was extracted with 150 ml of Dichloromethane (3 times) and then 300 ml of water. The organic layer was dried with anhydrous magnesium sulfate, and then the solvent was evaporated under reduced pressure. The residue was purified by column chromatography on silica to give product (5.2 g, 75%) as a light yellow solid.

Synthesis of Intermediate R

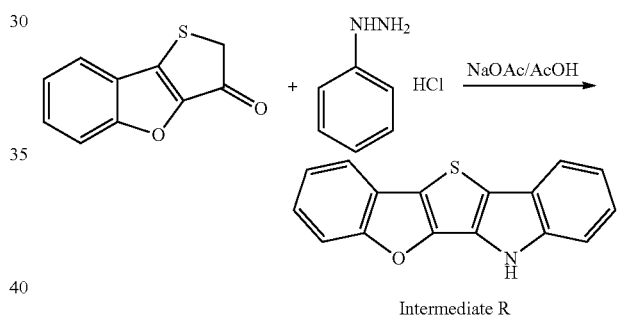

Intermediate R

A mixture of 5.2 g (27.4 mmole) of Intermediate Q, 4.7 g (32.9 mmole) of Phenylhydrazine hydrochloride, 4.5 g (54.8 mmole) of Sodium acetate, and 137 ml of Acetic acid was placed under nitrogen, and then heated at 120° C. for 1 h. After the reaction finished, the mixture was allowed to cool to room temperature. The precipitated product was filtered off with suction to give (5.1 g, 71%) of white product, which was washed from Toluene and EtOH. MS(m/z, EI$^+$): 262.3

Synthesis of EX147

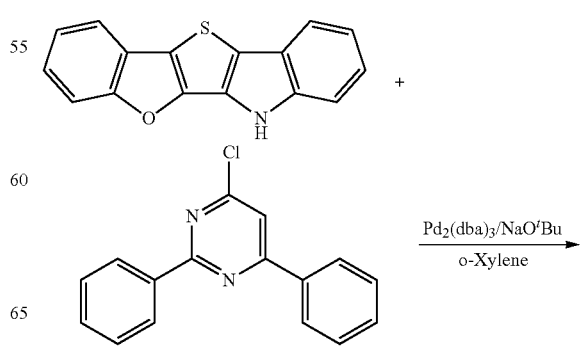

-continued

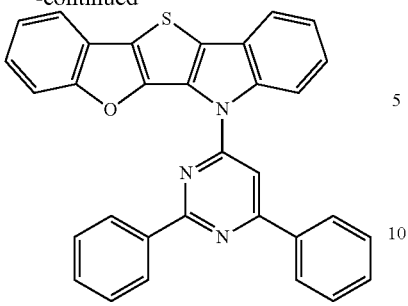

A mixture of 3.0 g (11.4 mmole) of Intermediate R, 3.6 g (13.7 mmol) of 4-Chloro-2,6-diphenylpyrimidine, 0.52 g (0.57 mmol) of Pd$_2$(dba)$_3$, 2.2 g (22.8 mmol) of Sodium tert-butoxide, and 30 ml of o-Xylene was degassed and placed under nitrogen, and then heated at 150° C. for 16 h. After the reaction finished, the mixture was allowed to cool to room temperature. Then 300 ml of MeOH was added while stirring and the precipitated product was filtered off with suction to give (2.4 g, 43%) of light yellow product, which was recrystallized from EtOH. MS(m/z, EI$^+$): 492.6

Obviously, many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A heteroacene having one of the following formulas:

EX1

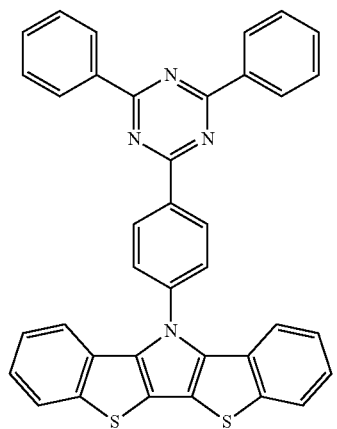

EX2

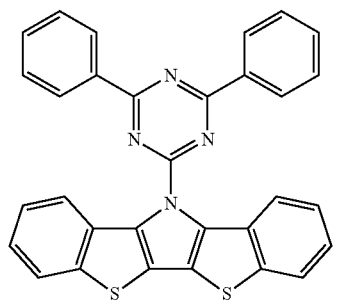

EX3

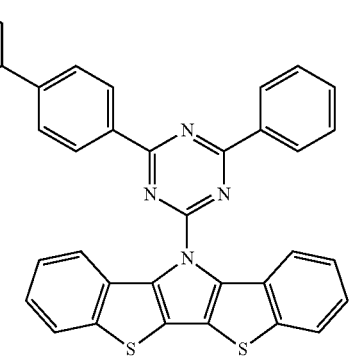

EX4

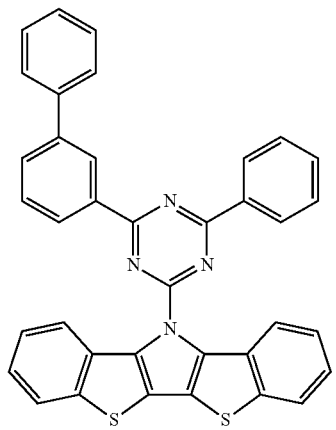

EX5

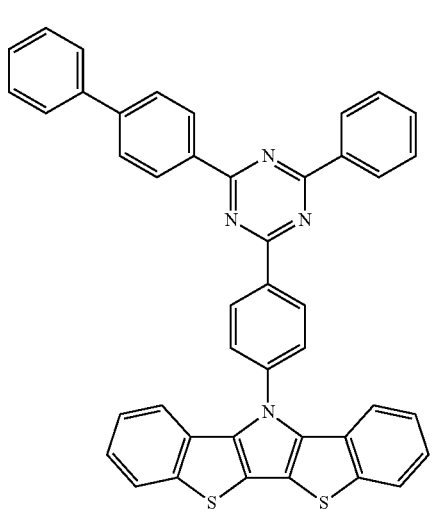

EX6
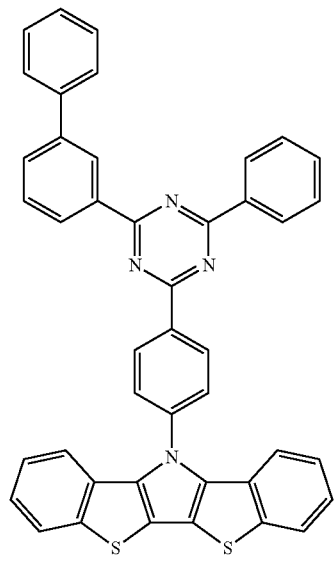
EX7
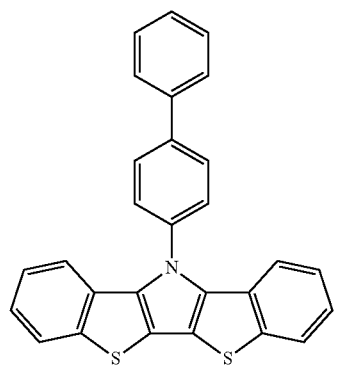
EX8
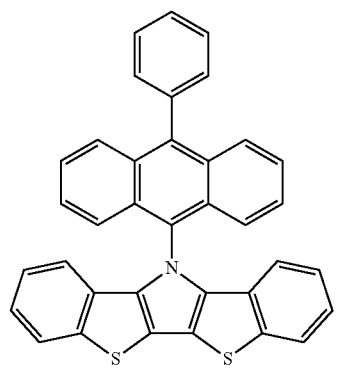
EX9
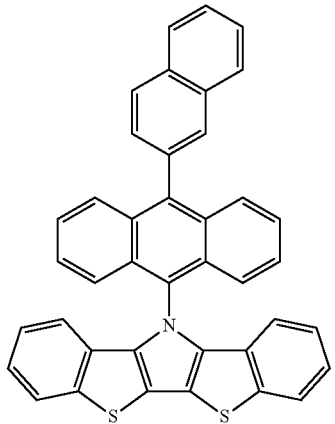
EX10
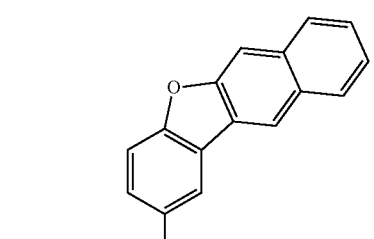
EX11
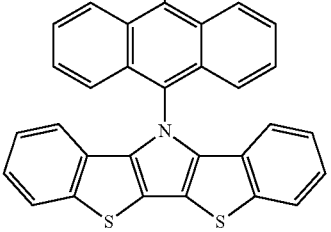
EX12
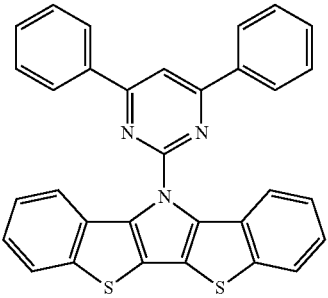

-continued
EX13
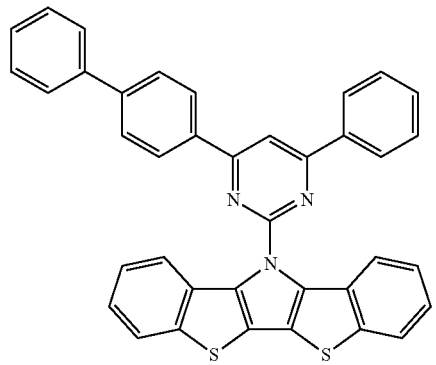
EX14
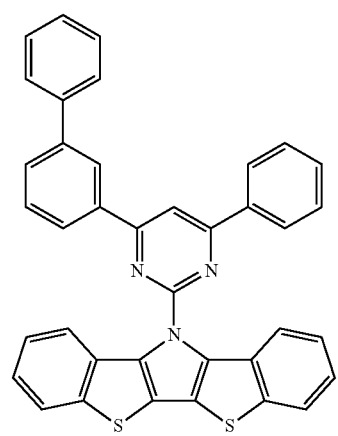
EX15
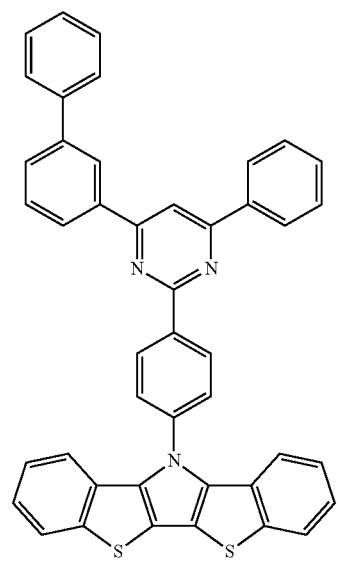
-continued
EX16
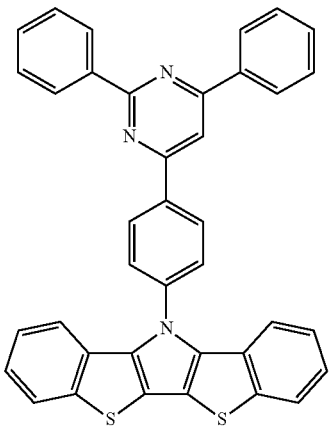
EX17
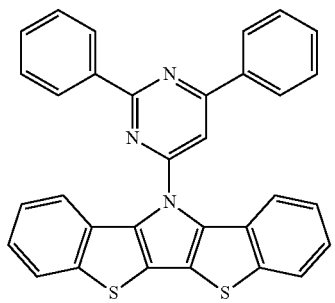
EX18
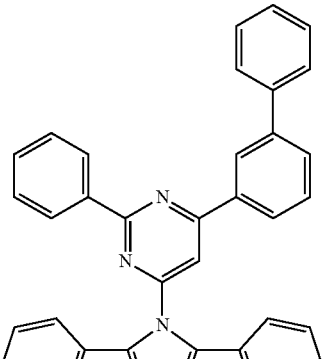
EX19
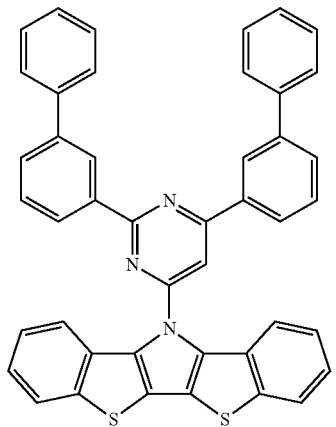

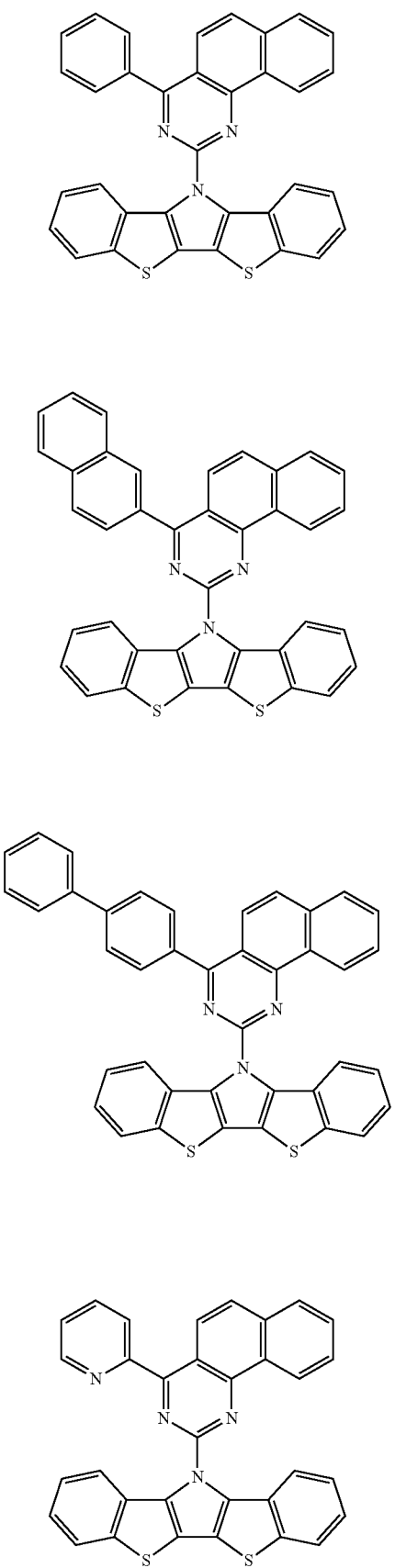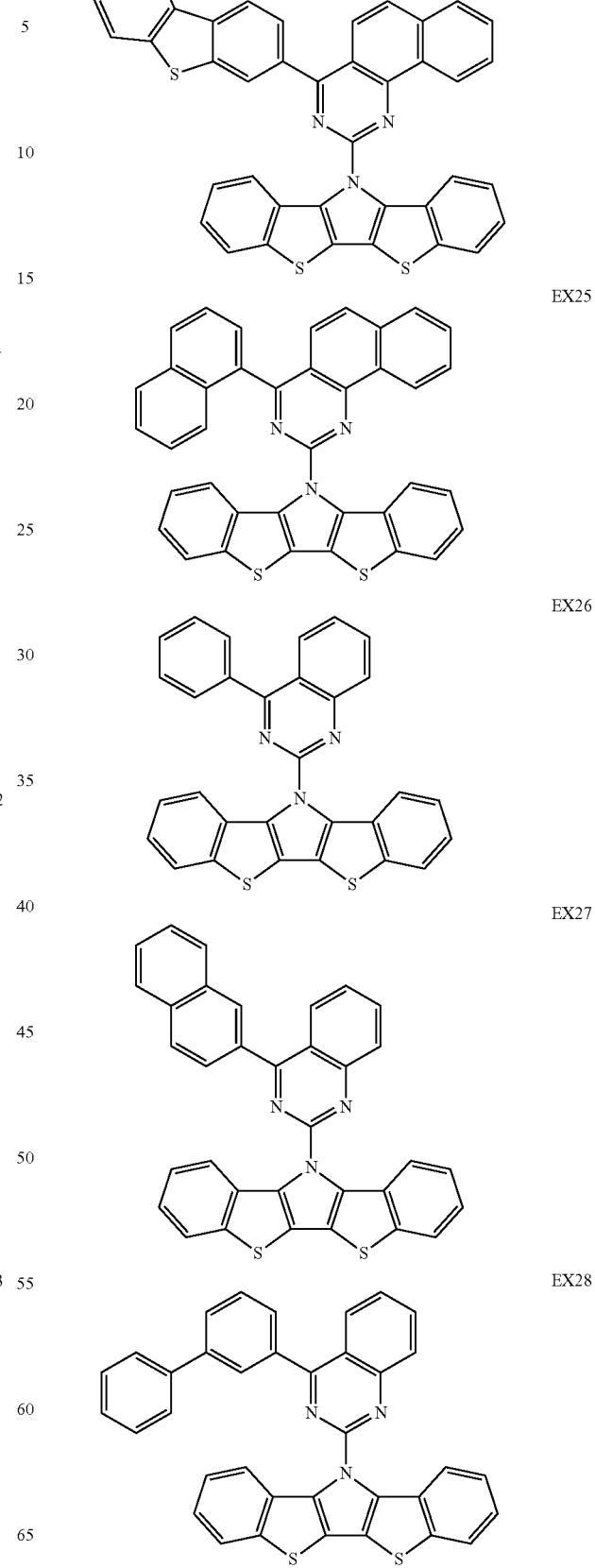

-continued
EX29
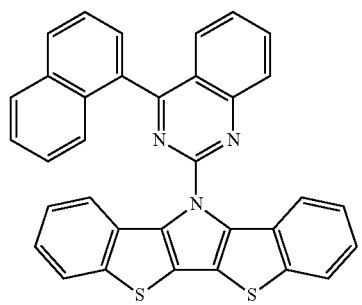
EX30
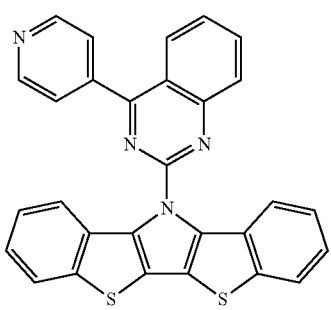
EX31
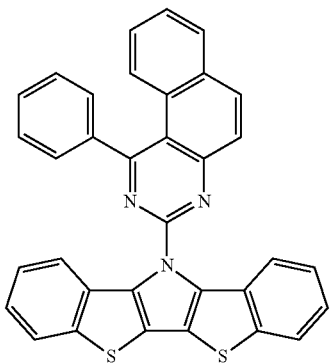
EX32
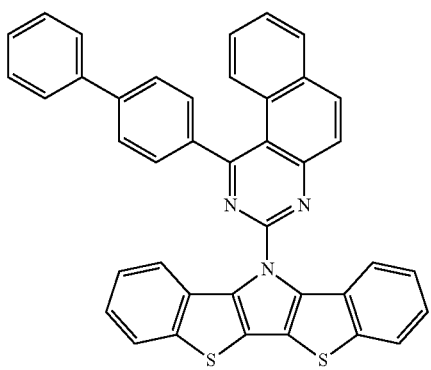
-continued
EX33
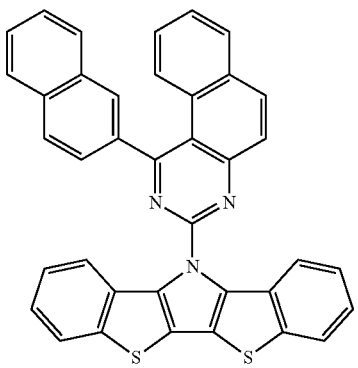
EX34
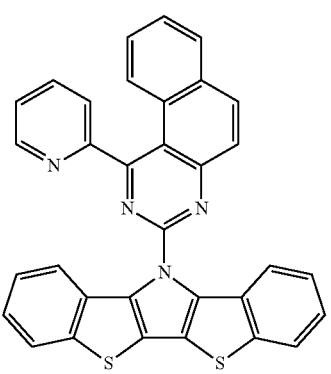
EX35
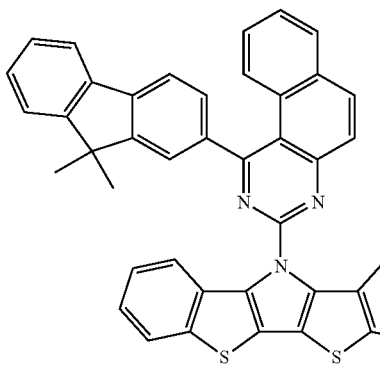
EX36
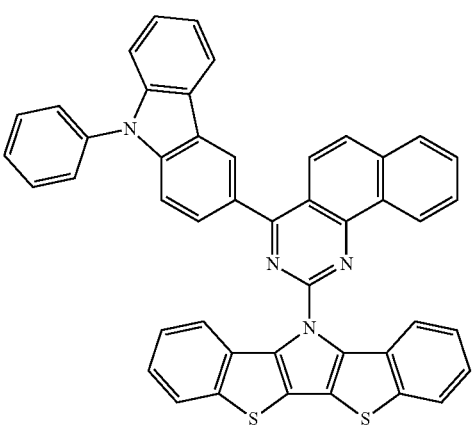

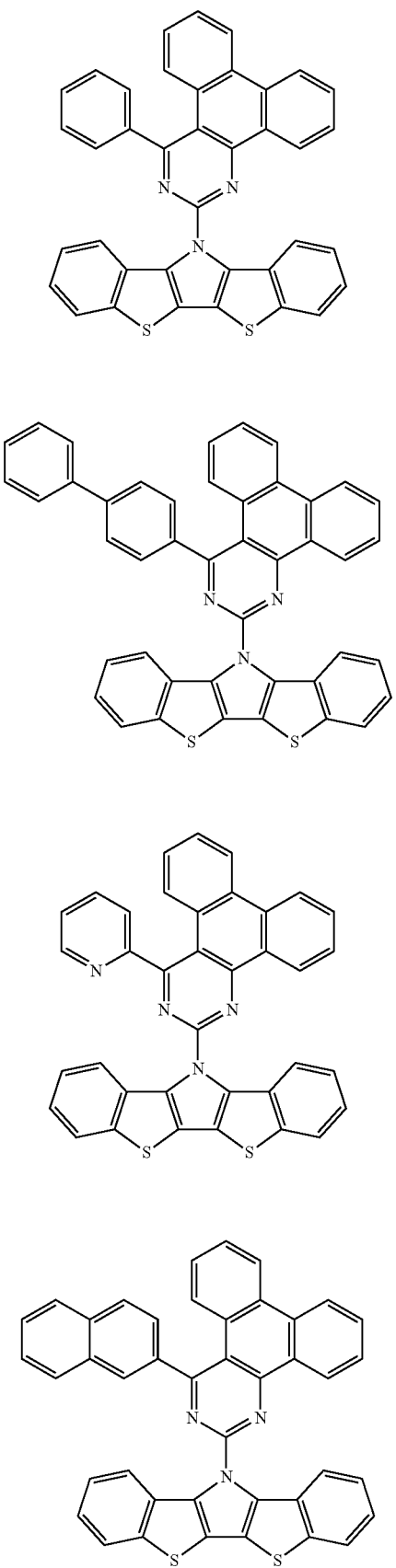
EX37
EX38
EX39
EX40
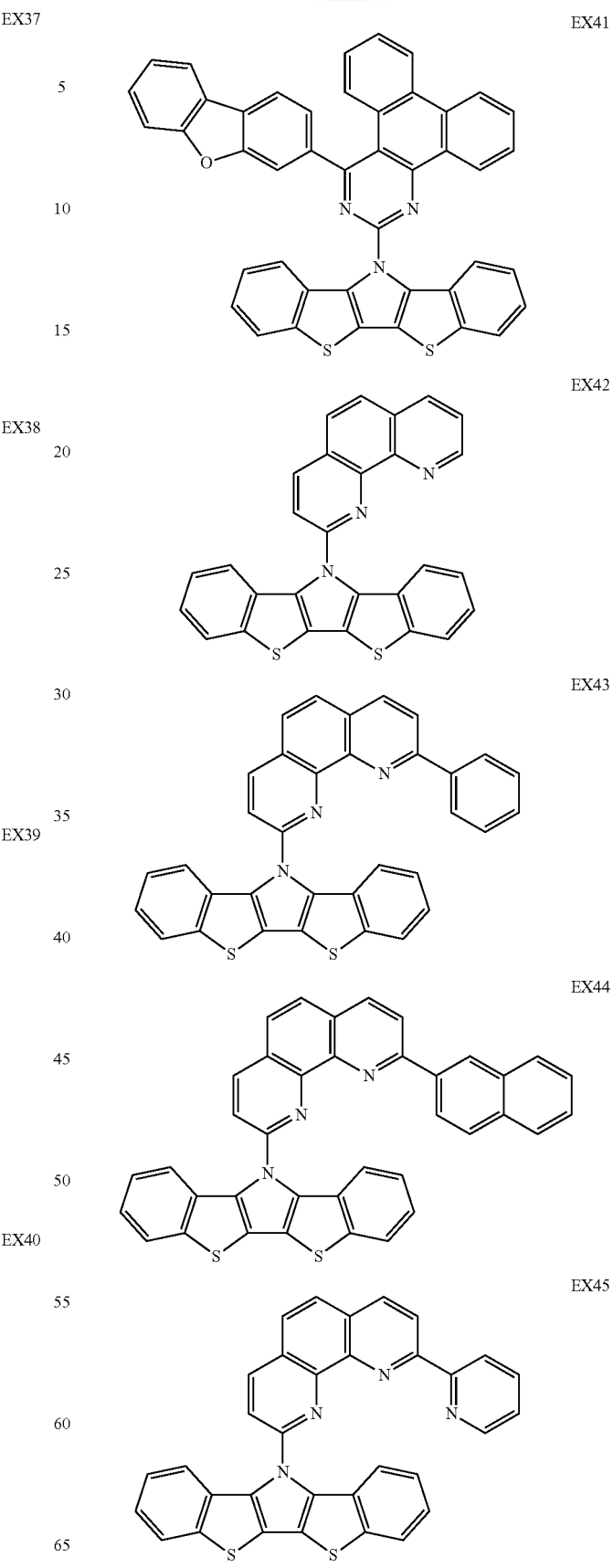
EX41
EX42
EX43
EX44
EX45

EX46
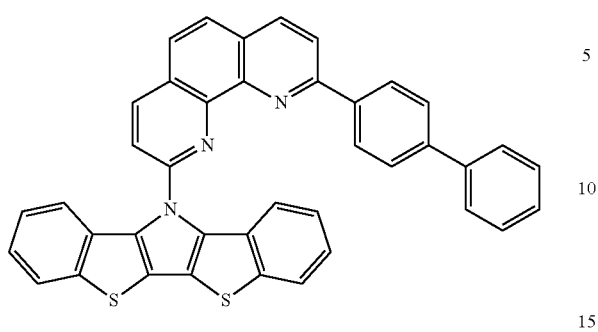
EX47
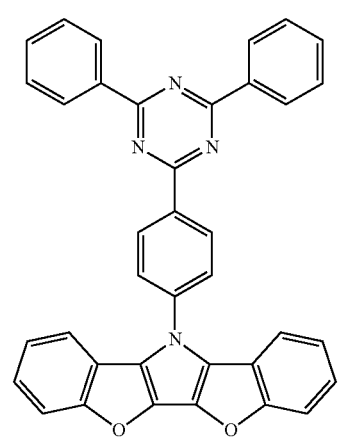
EX48
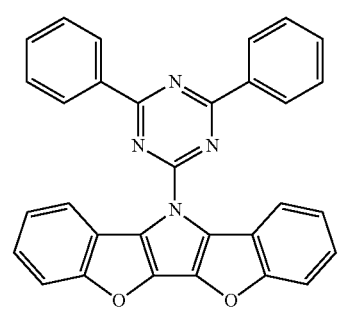
EX49
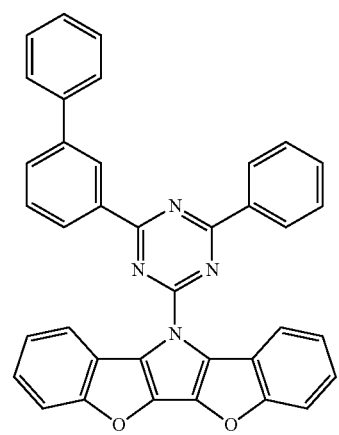
EX50
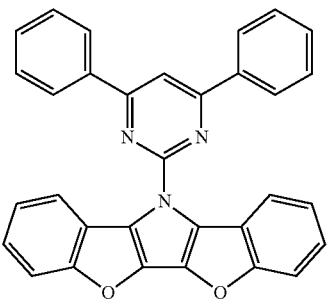
EX51
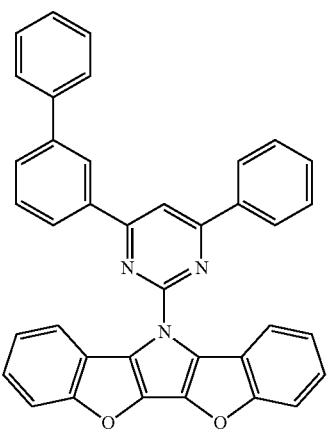
EX52
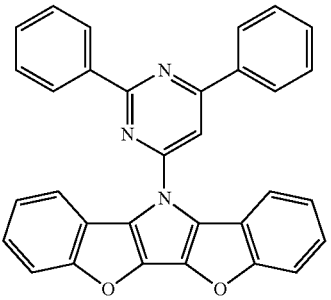
EX53
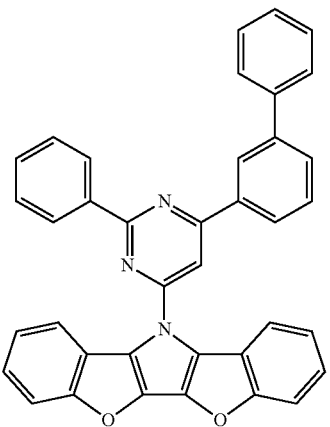

-continued
EX54
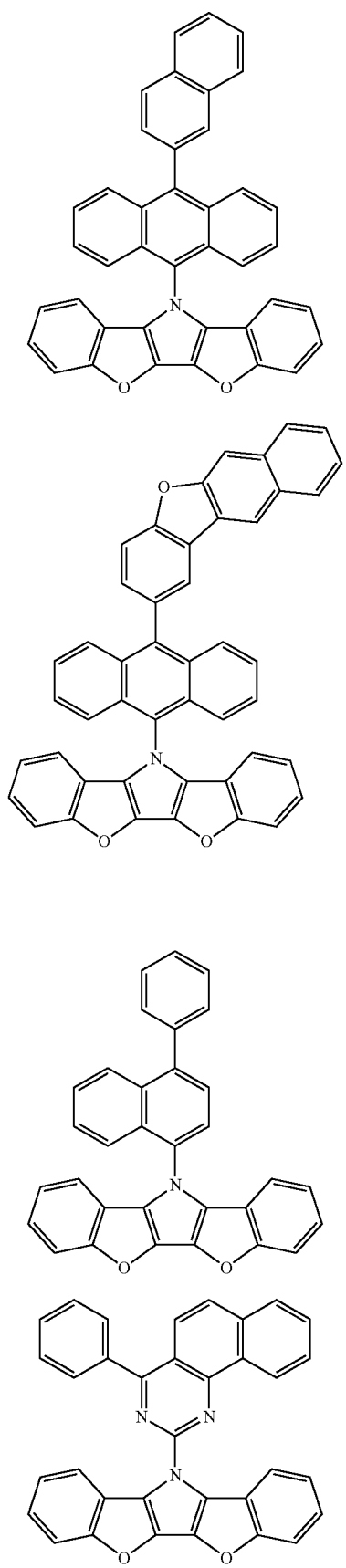
EX55
EX56
EX57
-continued
EX58
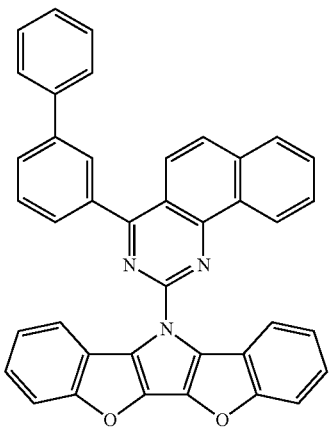
EX59
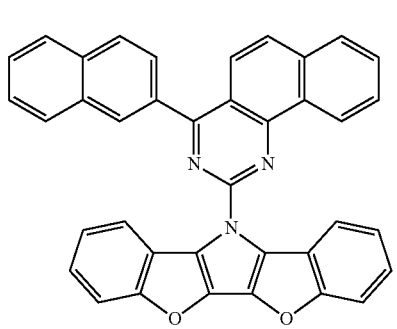
EX60
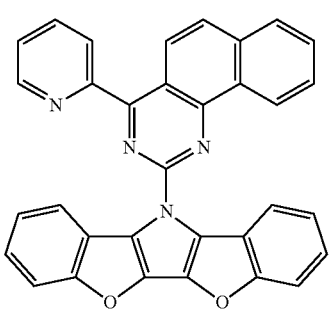
EX61
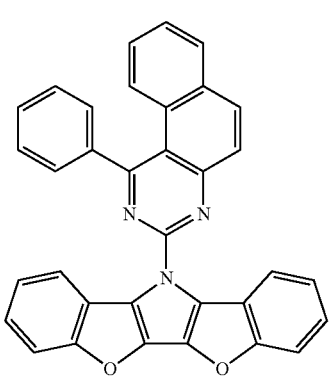

EX62
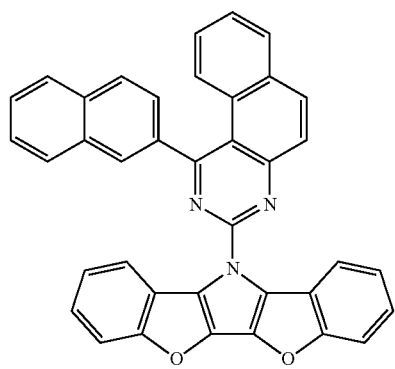
EX63
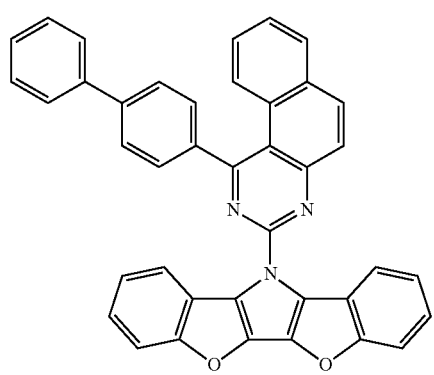
EX64
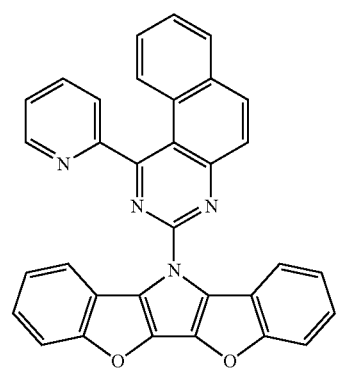
EX65
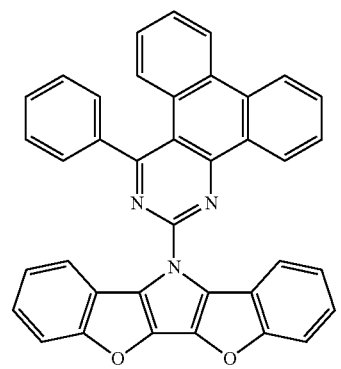
EX66
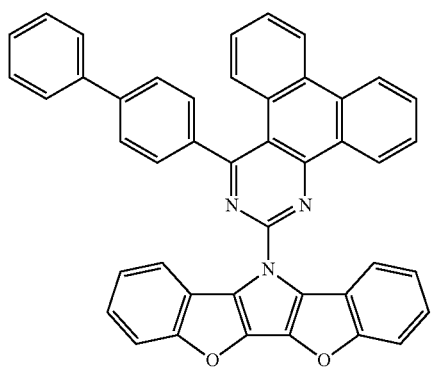
EX67
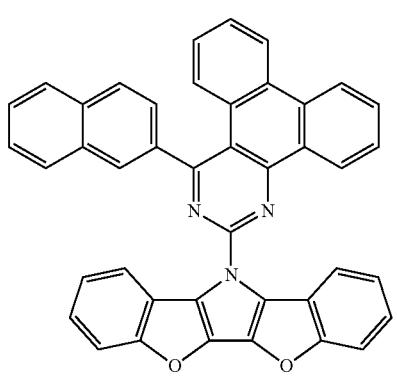
EX68
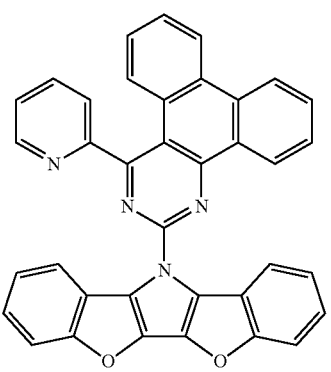
EX69
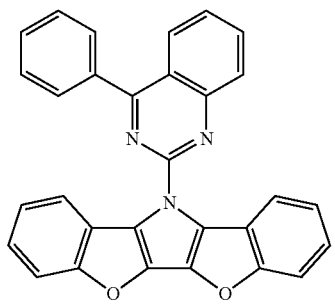

-continued
EX70
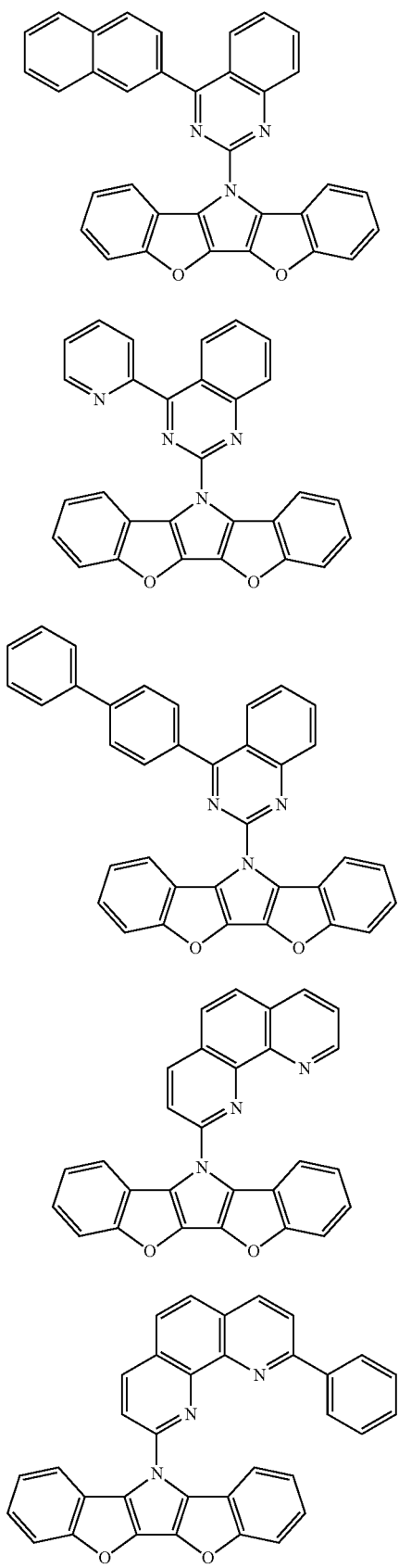
EX71
EX72
EX73
EX74
-continued
EX75
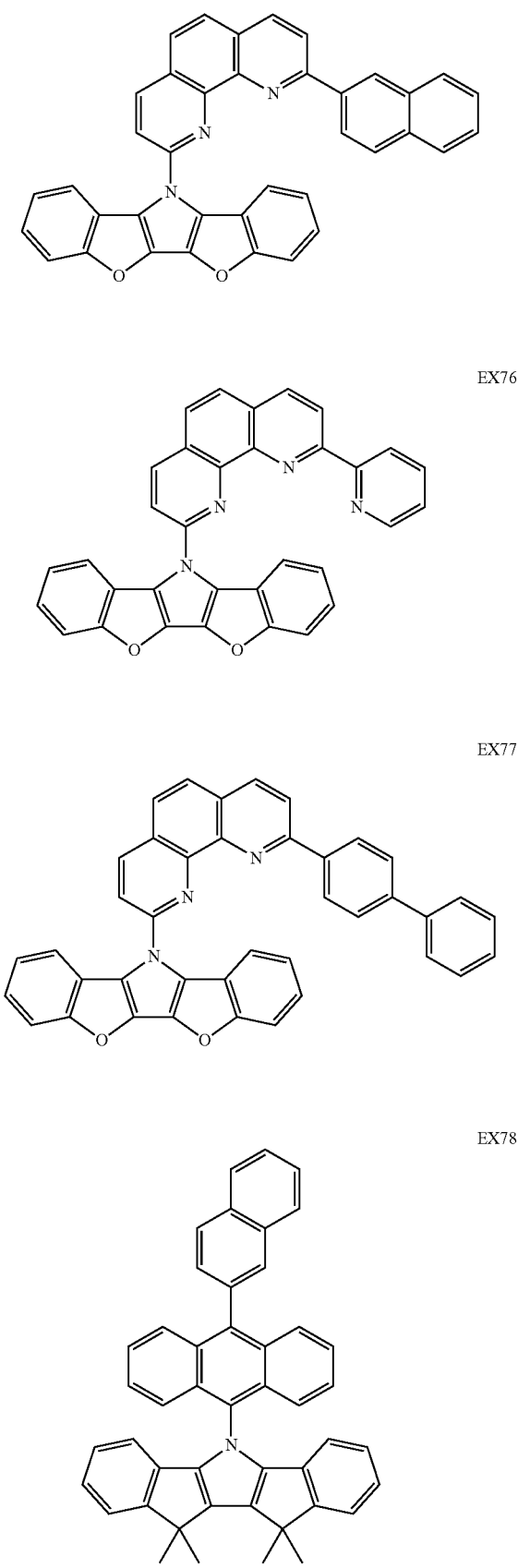
EX76
EX77
EX78

EX79
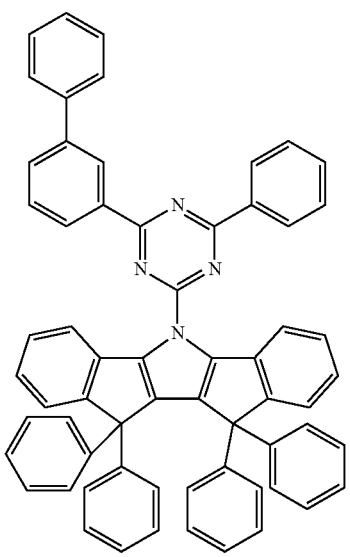
EX80
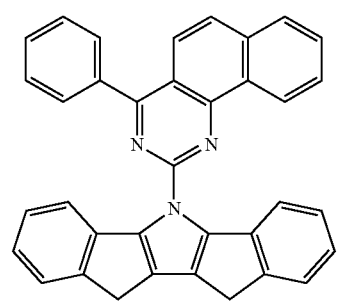
EX81
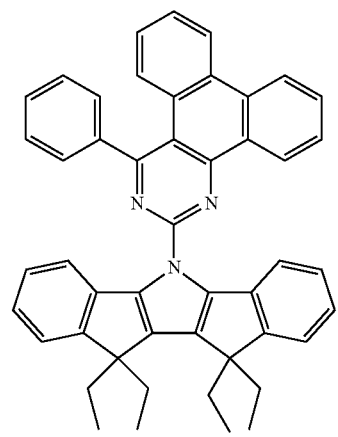
EX82
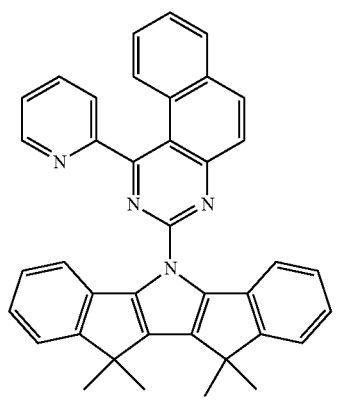
EX83
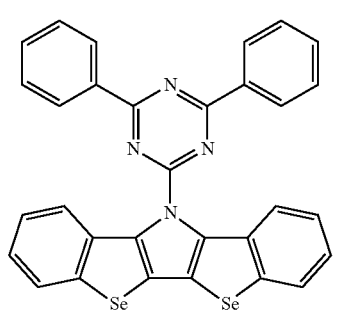
EX84
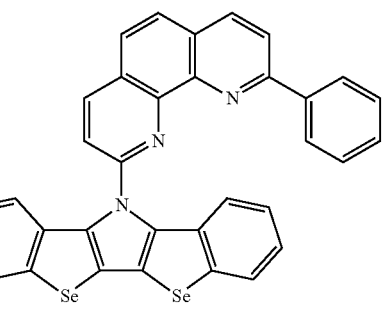
EX85
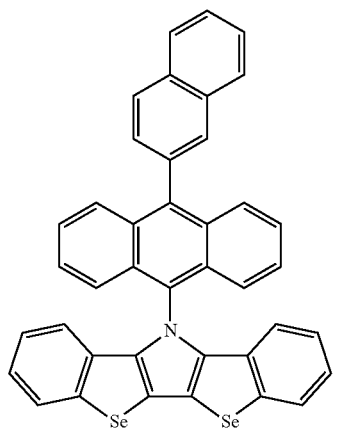

-continued
EX86
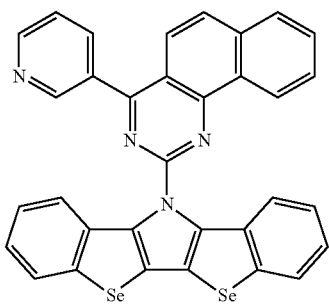
EX87
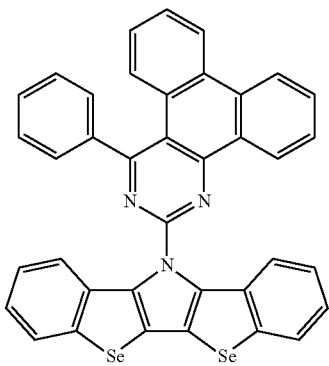
EX88
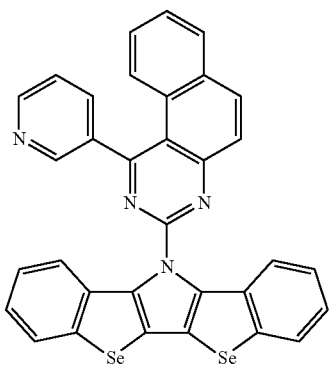
EX89
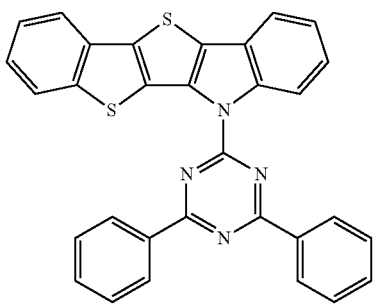
-continued
EX90
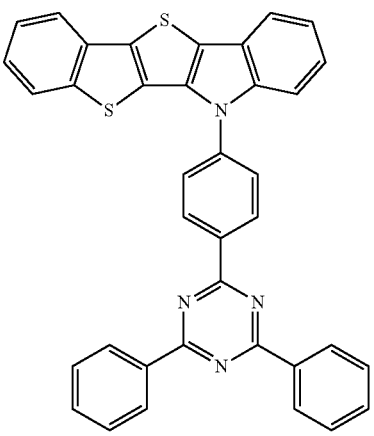
EX91
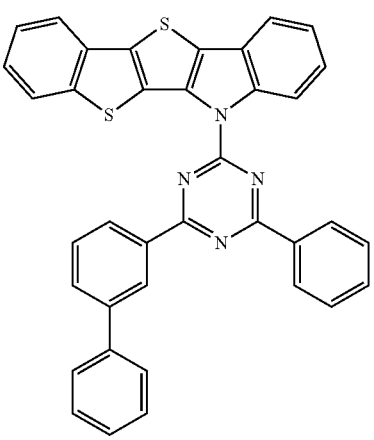
EX92
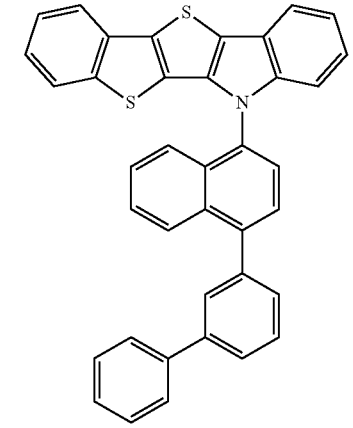

EX93
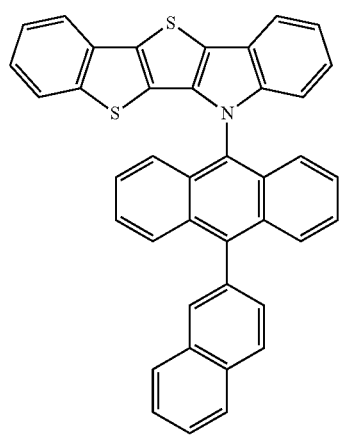
EX94
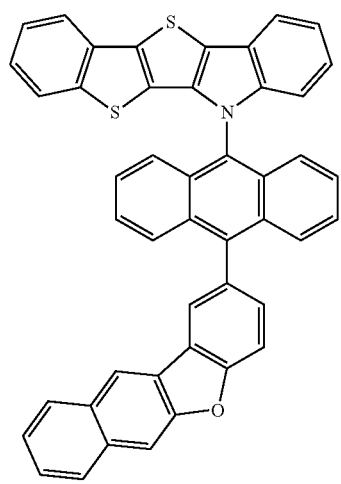
EX95
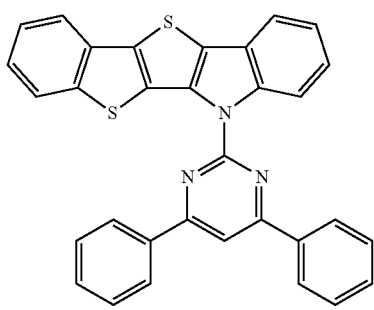
EX96
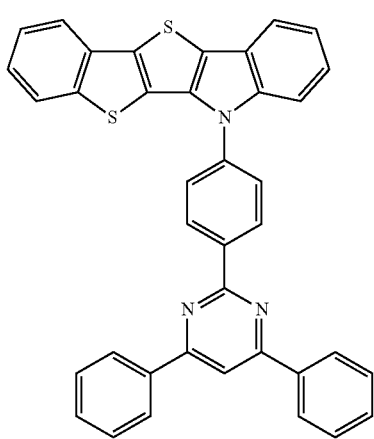
EX97
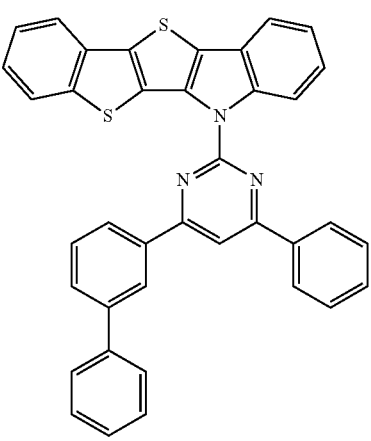
EX98
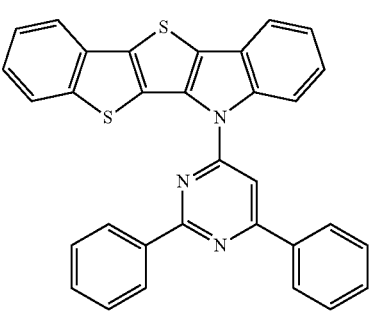
EX99
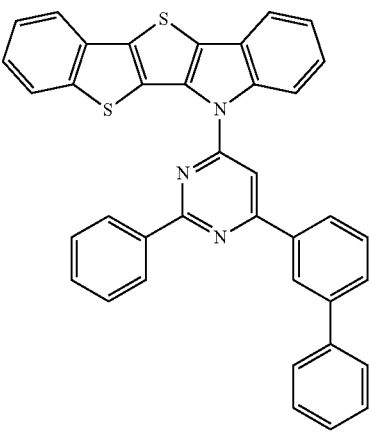
EX100
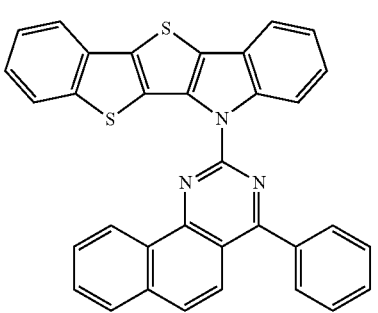

EX101 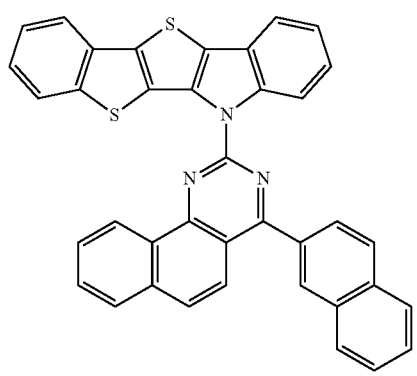
EX102 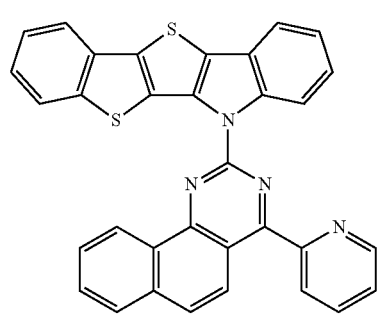
EX103 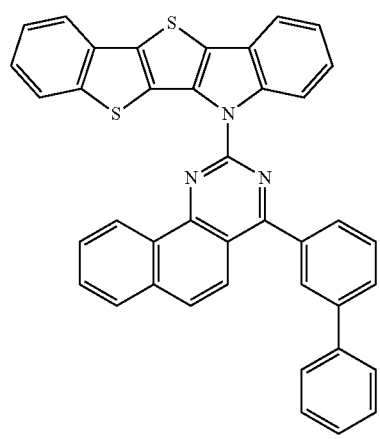
EX104 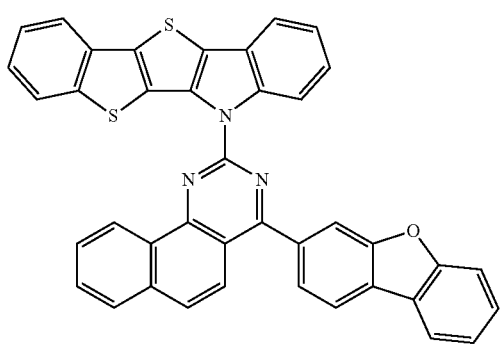
EX105 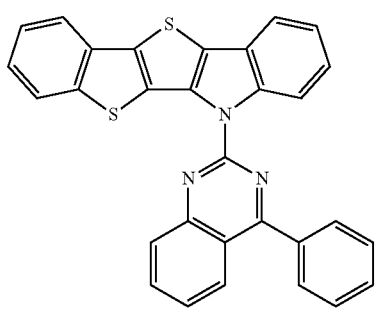
EX106 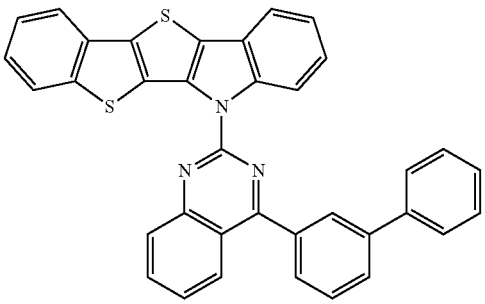
EX107 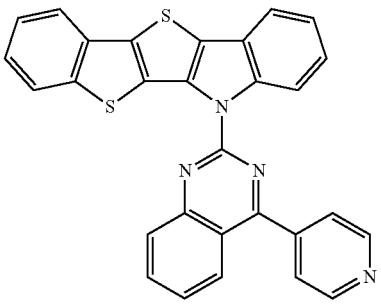
EX108 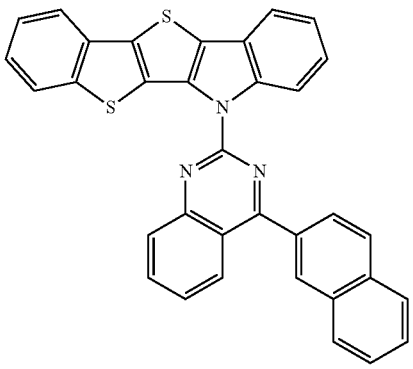

EX109
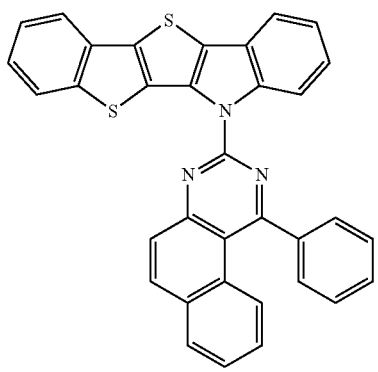
EX110
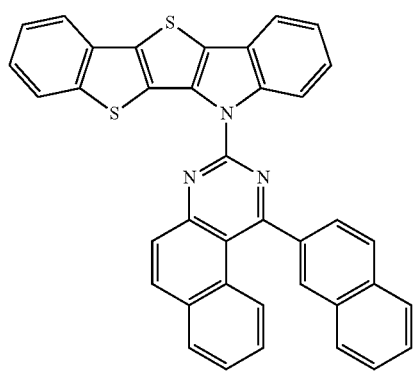
EX111
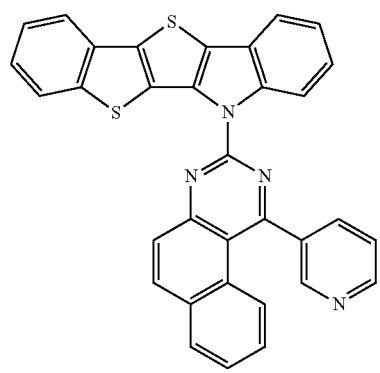
EX112
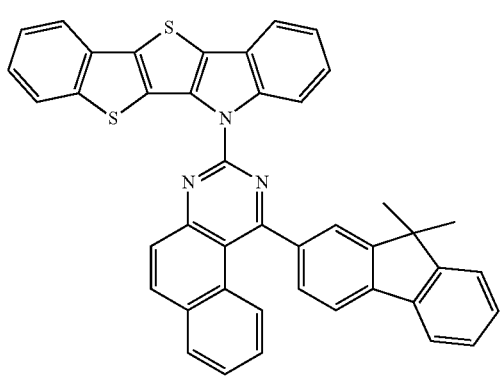
EX113
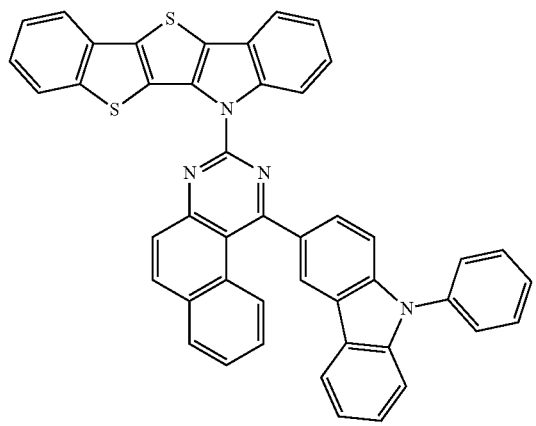
EX114
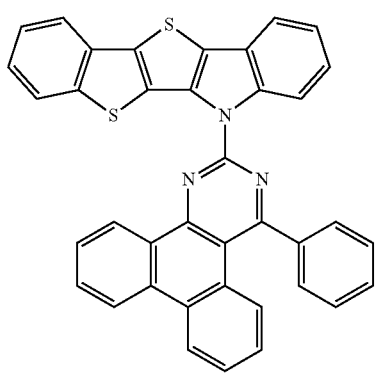
EX115
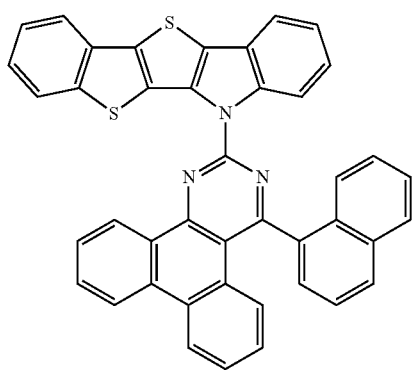
EX116
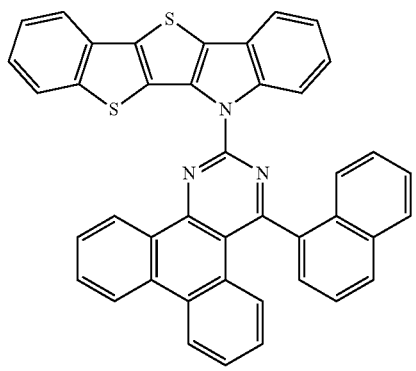

-continued
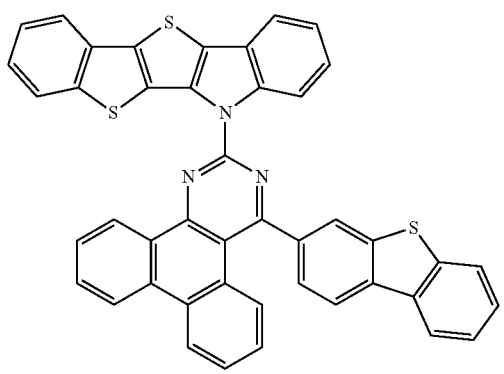
EX117
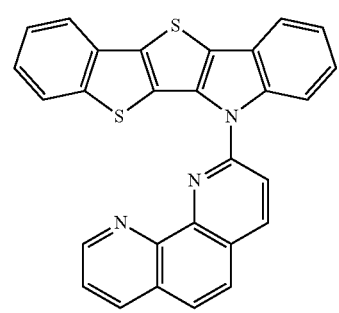
EX118
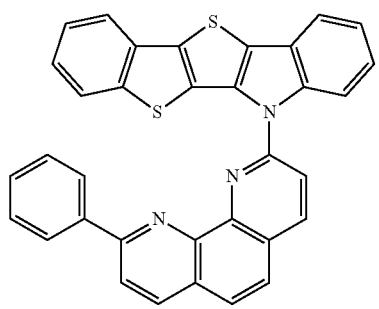
EX119
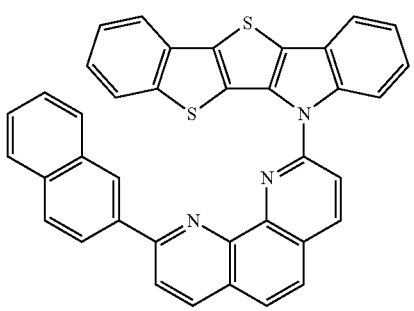
EX120
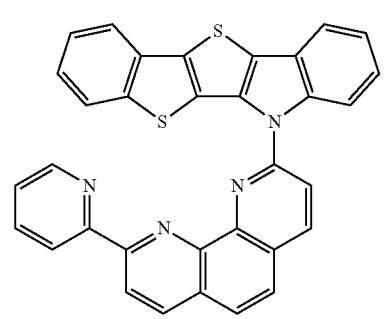
EX121
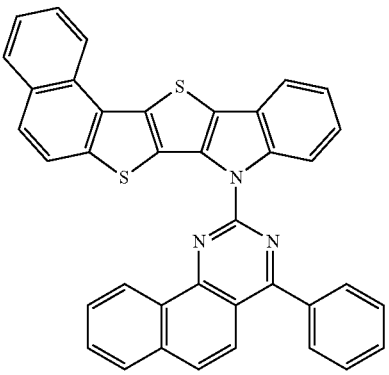
EX122
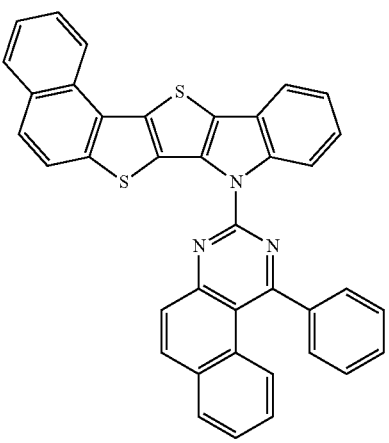
EX123
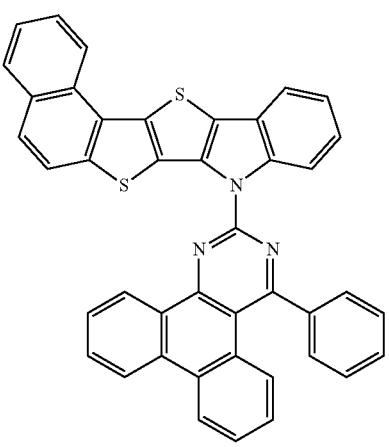
EX124
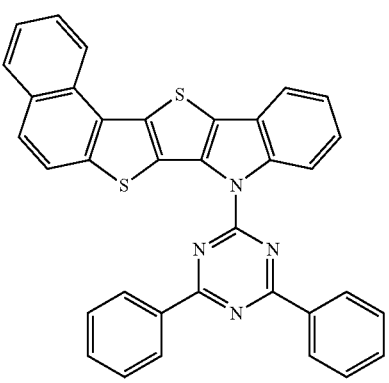
EX125

EX126
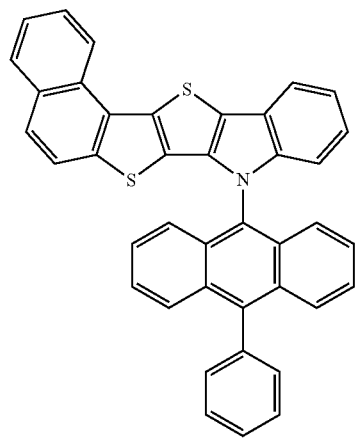
EX127
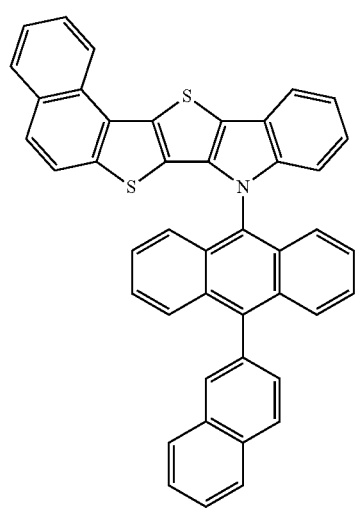
EX128
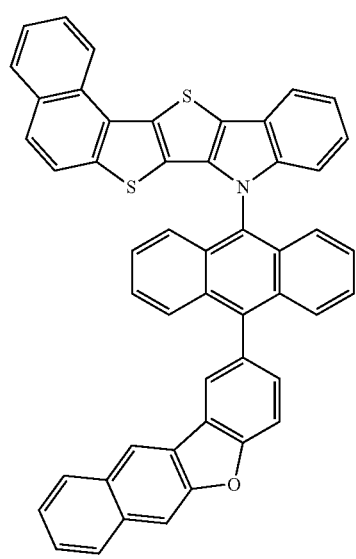
EX129
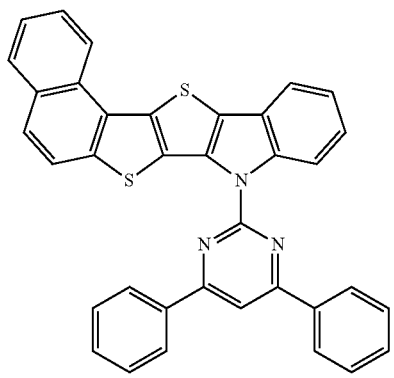
EX130
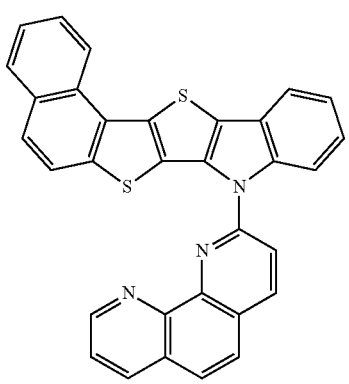
EX131
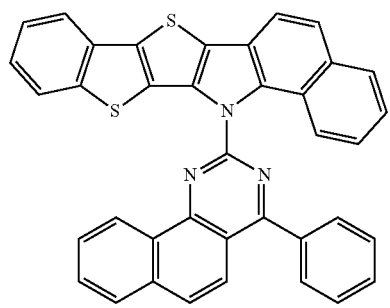
EX132
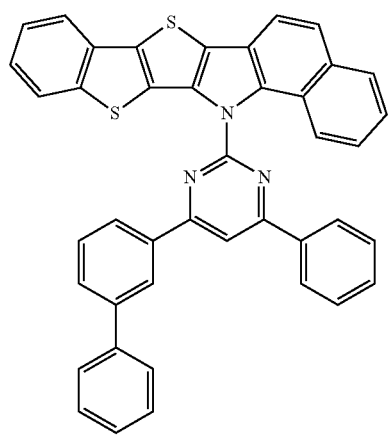

EX133
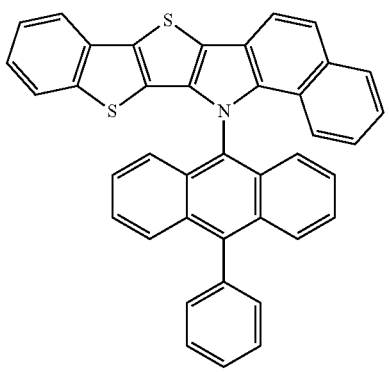
EX134
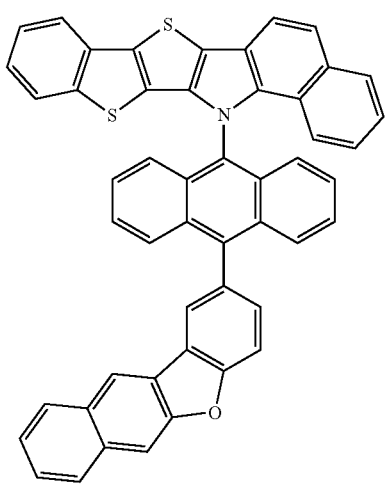
EX135
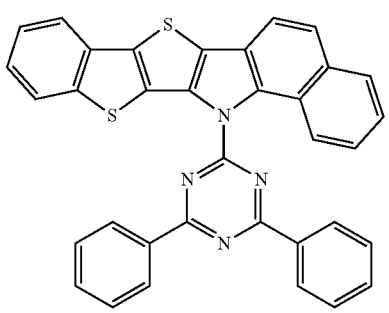
EX136
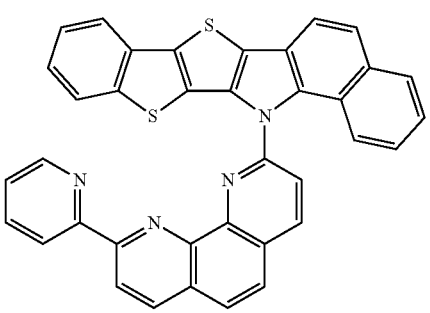
EX137
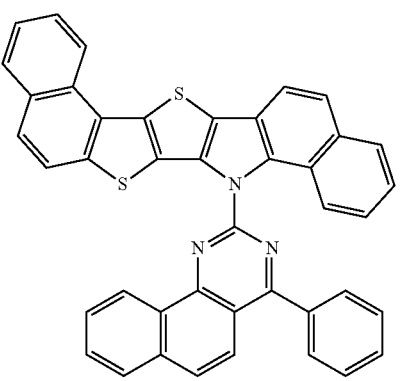
EX138
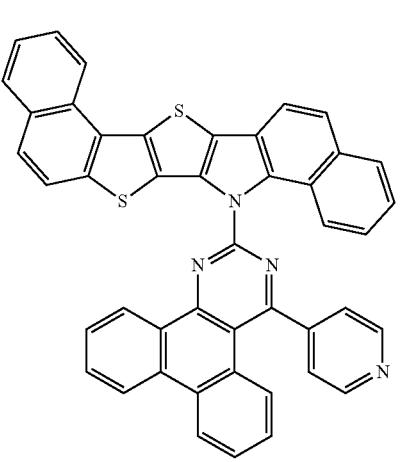
EX139
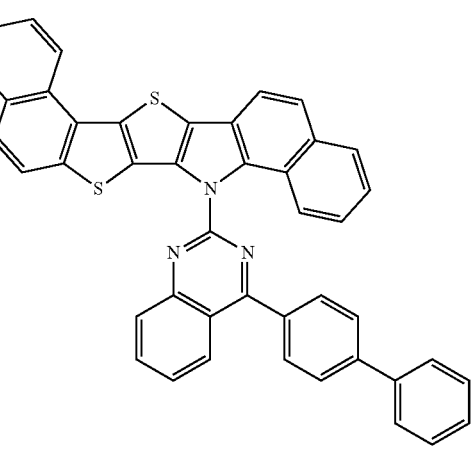

EX140
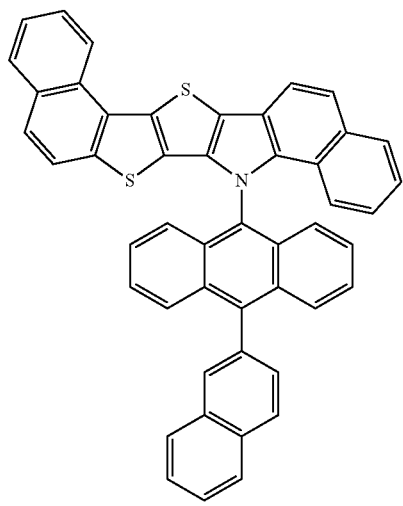
EX141
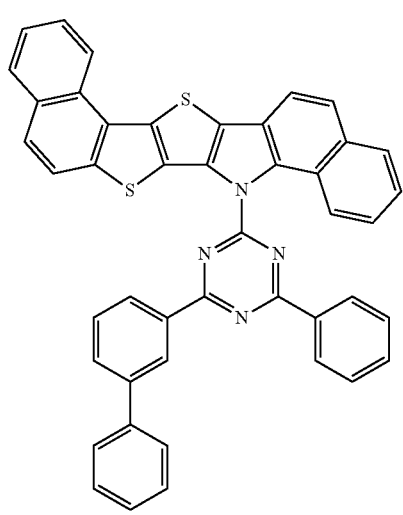
EX142
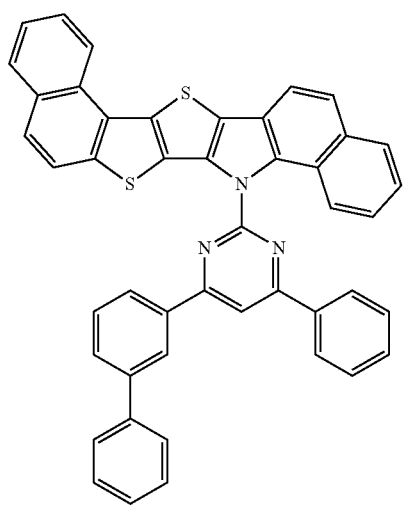
EX143
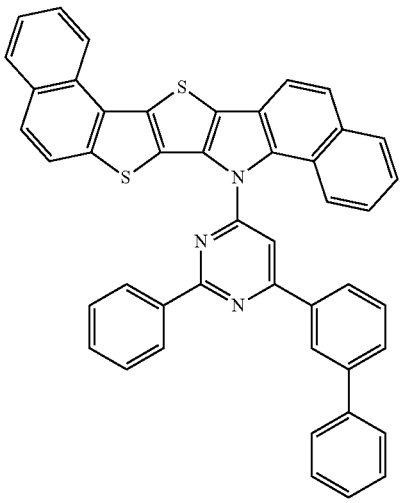
EX144
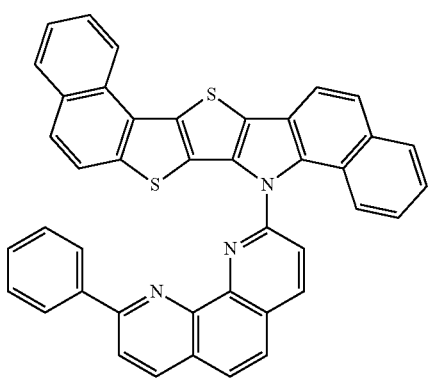
EX145
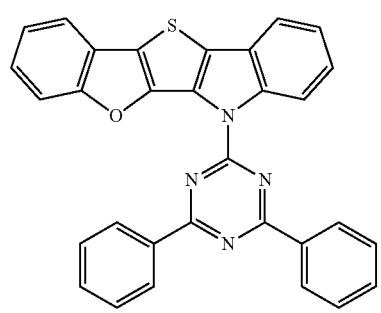
EX146
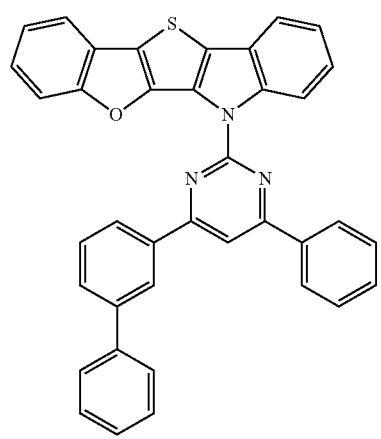

EX147
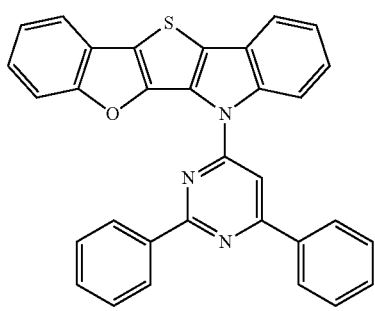
EX148
EX149
EX150
EX151
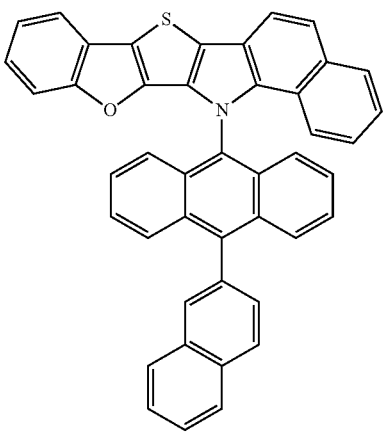
EX152
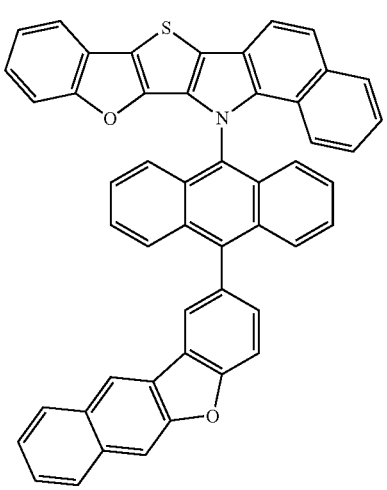
EX156
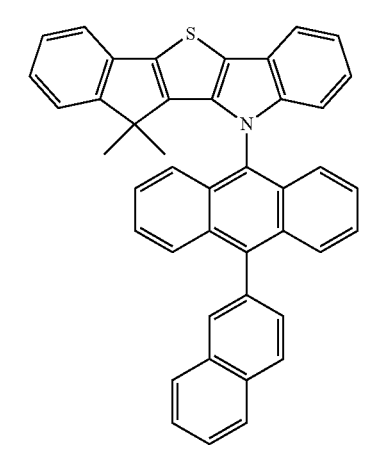
EX157
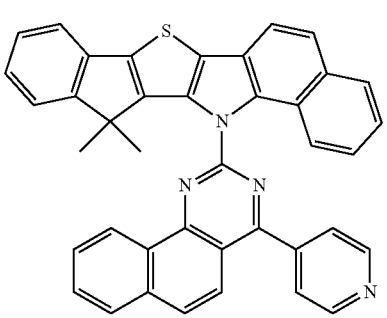

EX158 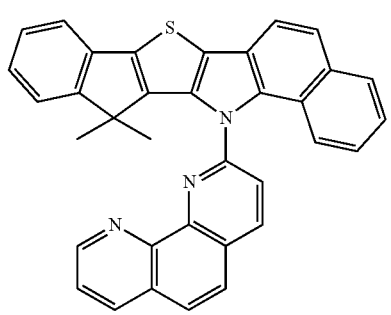
EX159 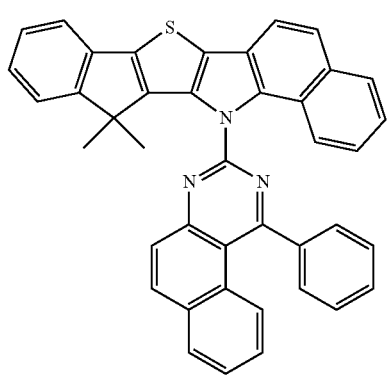
EX160 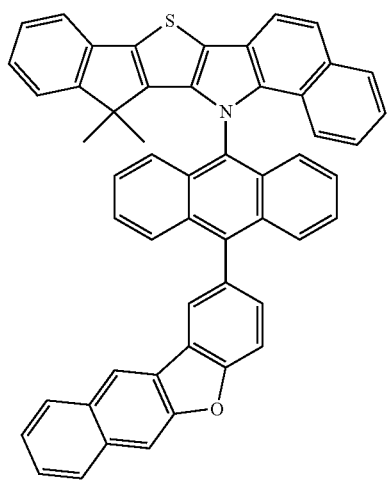
EX161 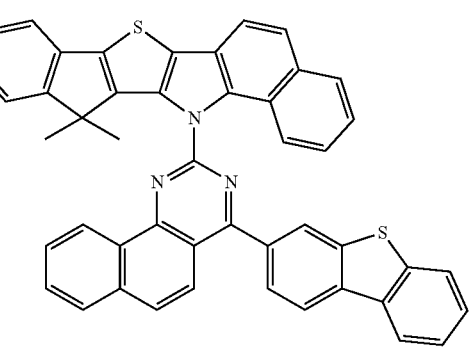
EX162 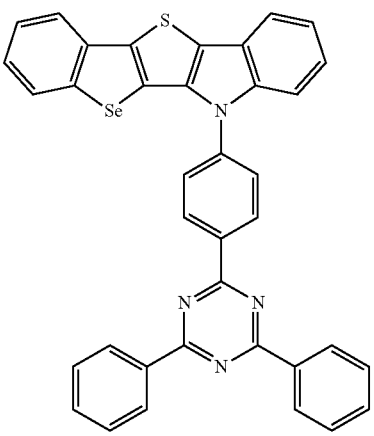
EX163 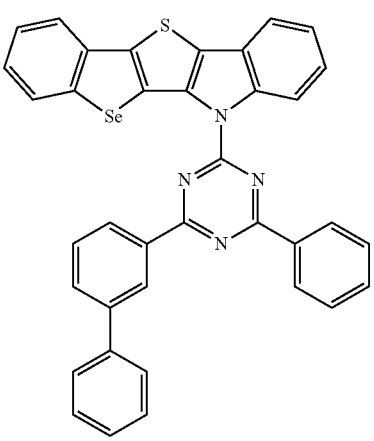
EX164 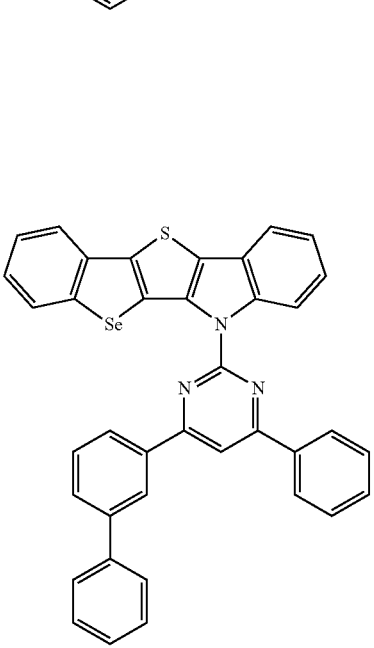

EX165

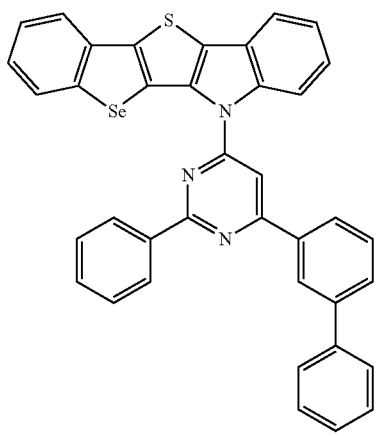

EX166

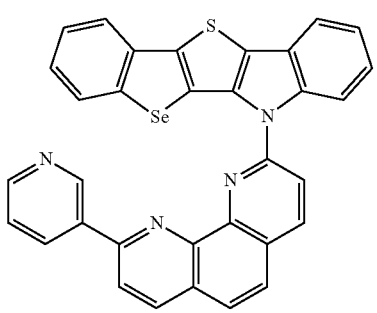

EX167

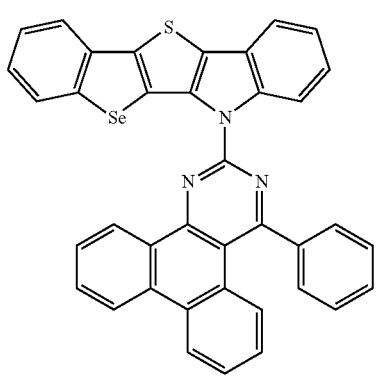

EX168

EX169

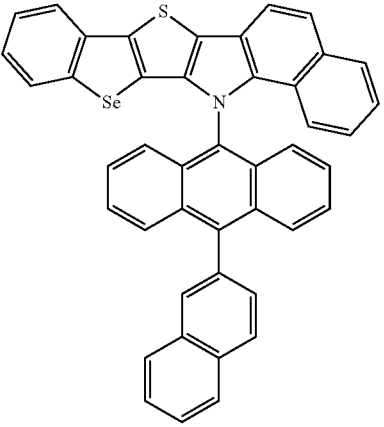

EX170

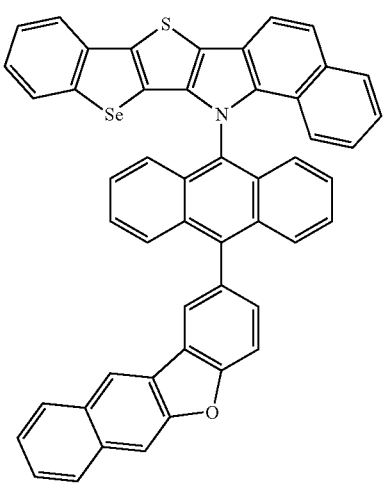

and

EX171

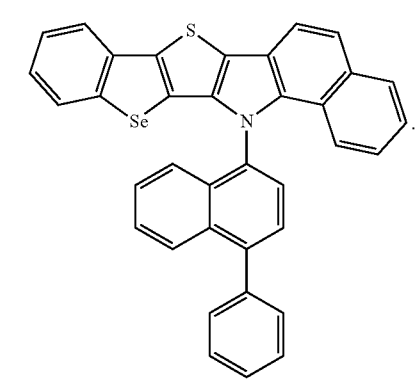

2. An organic electroluminescence device comprising an anode, a cathode and one or more organic layers formed between the anode and the cathode, wherein at least one of the organic layers comprises the heteroacene according to claim 1.

3. The organic electroluminescence device according to claim 2, wherein the organic layers comprise an emissive layer having a host, and wherein the heteroacene is comprised as the host.

4. The organic electroluminescence device according to claim 3, wherein the host is a fluorescent host.

5. The organic electroluminescence device according to claim 3, wherein the host is a phosphorescent host.

6. The organic electroluminescence device according to claim 2, wherein the organic layers comprise an electron transport layer, and wherein the heteroacene of claim 1 is comprised as the electron transport layer.

7. The organic electroluminescence device according to claim 2, wherein the organic layers comprise a hole blocking layer, and wherein the heteroacene of claim 1 is comprised as the hole blocking layer.

8. The organic electroluminescent device according to claim 2, wherein the organic electroluminescence device is a lighting panel.

9. The organic electroluminescent device according to claim 2, wherein the organic electroluminescence device is a backlight panel.

\* \* \* \* \*